United States Patent
Walker

(10) Patent No.: US 10,501,764 B2
(45) Date of Patent: *Dec. 10, 2019

(54) BIOSYNTHESIS OF PACLITAXEL INTERMEDIATE

(71) Applicant: Board of Trustees of Michigan State University, East Lansing, MI (US)

(72) Inventor: Kevin Walker, Holt, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/671,882

(22) Filed: Aug. 8, 2017

(65) Prior Publication Data

US 2017/0342451 A1 Nov. 30, 2017

Related U.S. Application Data

(63) Continuation of application No. 14/408,515, filed as application No. PCT/US2012/042951 on Jun. 18, 2012, now Pat. No. 9,732,365.

(51) Int. Cl.
*C12P 17/02* (2006.01)
*C12N 9/90* (2006.01)

(52) U.S. Cl.
CPC ............... *C12P 17/02* (2013.01); *C12N 9/90* (2013.01); *C12Y 501/01011* (2013.01)

(58) Field of Classification Search
None
See application file for complete search history.

(56) References Cited

U.S. PATENT DOCUMENTS

| | | | |
|---|---|---|---|
| 3,907,989 | A | 9/1975 | Shimojima et al. |
| 5,380,751 | A | 1/1995 | Chen et al. |
| 7,273,755 | B2 | 9/2007 | Steele et al. |
| 9,732,365 | B2 | 8/2017 | Walker |
| 2004/0005562 | A9 | 1/2004 | Croteau et al. |
| 2010/0048422 | A1 | 2/2010 | Walsh et al. |
| 2015/0284751 | A1 | 10/2015 | Walker |

FOREIGN PATENT DOCUMENTS

WO WO-2013191678 A1 12/2013

OTHER PUBLICATIONS

"U.S. Appl. No. 14/408,515, Non Final Office Action dated Aug. 15, 2016", 15 pgs.
"U.S. Appl. No. 14/408,515, Notice of Allowance dated Apr. 4, 2017", 23 pgs.
"U.S. Appl. No. 14/408,515, Response filed July 19, 2016 to Restriction Requirement dated May 20, 2016", 18 pgs.
"U.S. Appl. No. 14/408,515, Restriction Requirement dated May 20, 2016", 7 pgs.
"U.S. Appl. No. 14/408,515, Response filed Dec. 15, 2016 to Non Final Office Action dated Aug. 15, 2016", 40 pgs.
"GenBank X13237", [Online] Retrieved From Internet: <http://www.ncbi.nlm.nih.gov/nuccore/X13237>, (Apr. 18, 2005)
"International Application Serial No. PCT/US2012/042951, International Preliminary Report on Patentability dated Dec. 31, 2014", 9 pgs.
"International Application Serial No. PCT/US2012/042951, International Search Report dated Dec. 13, 2012", 6 pgs.
"International Application Serial No. PCT/US2012/042951, Invitation to Pay Add'l Fees and Partial Search Report dated Oct. 1, 2012", 2 pgs.
"International Application Serial No. PCT/US2012/042951, Written Opinion dated Dec. 13, 2012", 7 pgs.
"UniProKB P09095", [Online] Retrieved From Internet: <http://www.ncbi.nlm.nih.gov/protein/P09095>, (Nov. 29, 2012).
Jennewein, et al., "", Natl. Acad . Sci. 101 (24), (2004), 9149-9154.
Linne, Uwe, et al., "Aminoacyl-coenzyme A synthesis catalyzed by adenylation domains", (Mar. 2007), 905-910.
Mootz, H D, et al., "The Tyrocidine Biosynthesis Operon of Bacillus brevis: Complete Nucleotide Sequence and Biochemical Characterization of Functional Internal Adenylation Domains.", 6843-6850.
Villier, et al., "", ChemBioChem 10 (4), (2009), 671-682.
Watts, Kevin T, et al., "Current and Emerging Approaches for Natural Product Biosynthesis in Microbial Cells", (2005), 927-940.

*Primary Examiner* — Paul J Holland
(74) *Attorney, Agent, or Firm* — Schwegman Lundberg & Woessner, P.A.

(57) ABSTRACT

The invention relates to methods of making compounds useful for production of paclitaxel and analogs or derivatives thereof.

23 Claims, 26 Drawing Sheets
Specification includes a Sequence Listing.

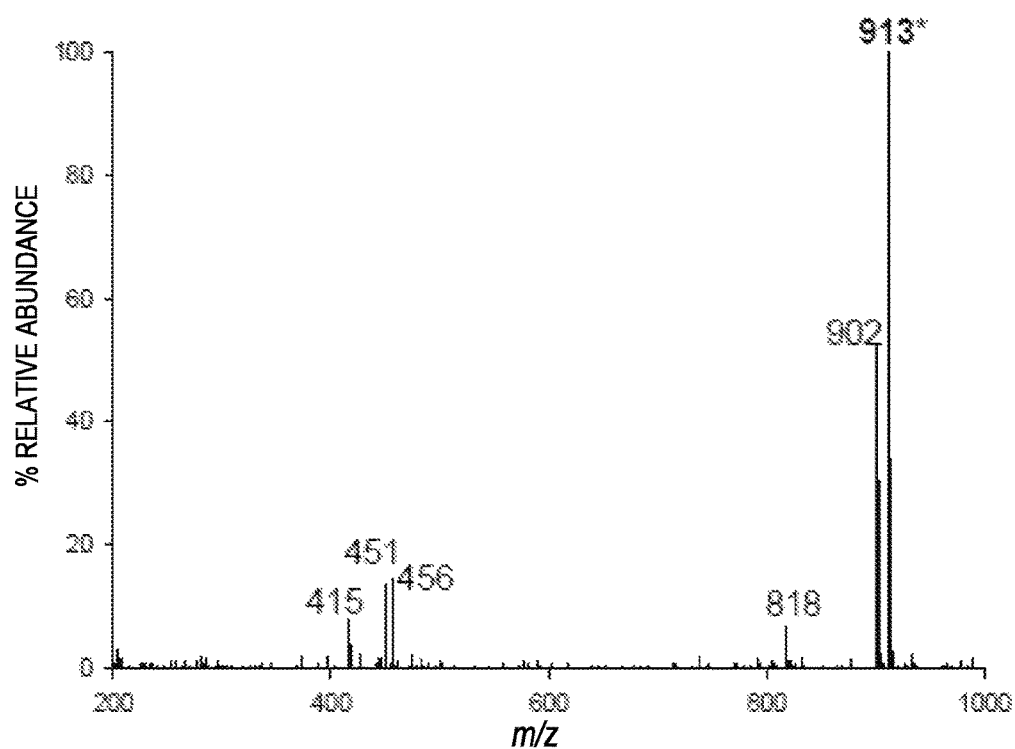
FIG. 2A1
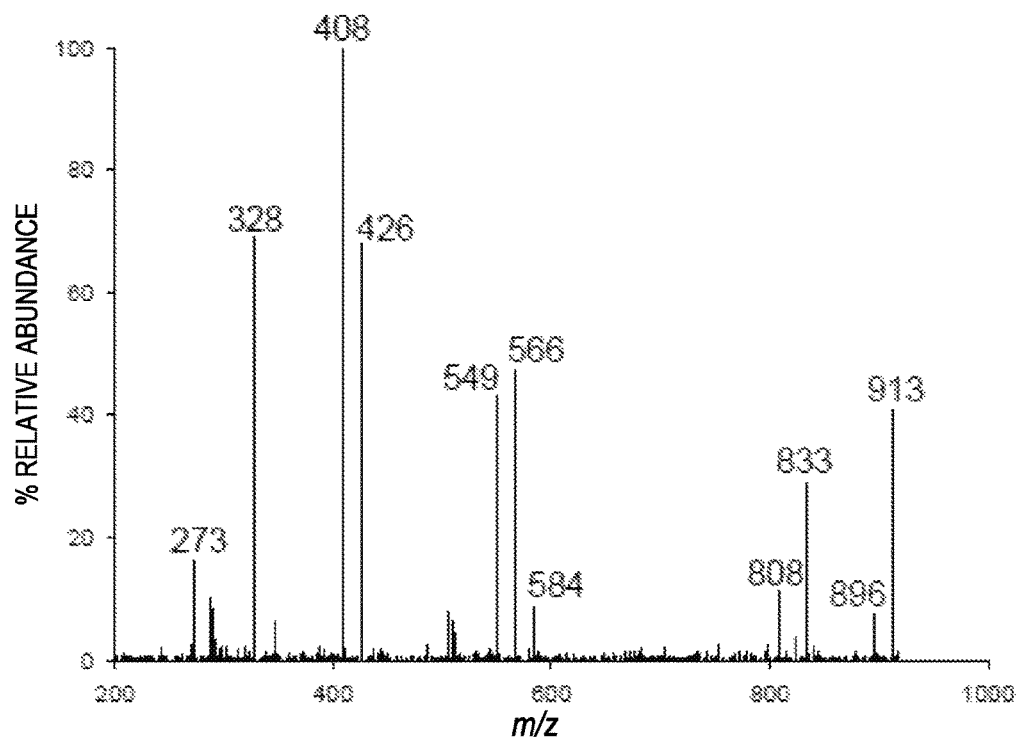
FIG. 2A2

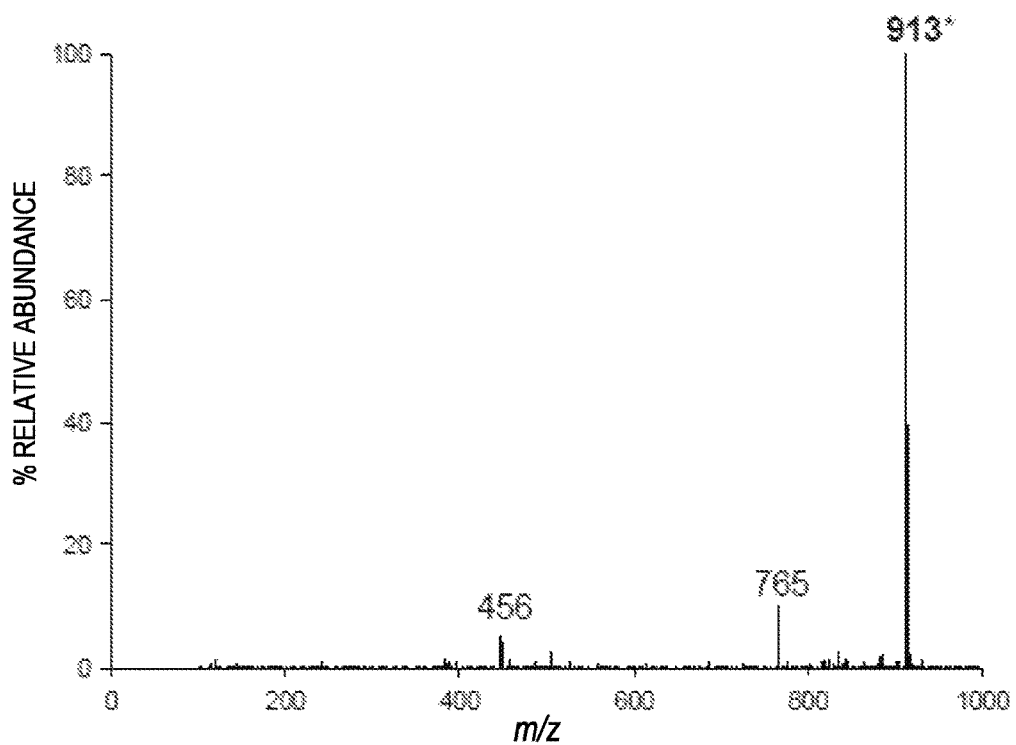
FIG. 2B1
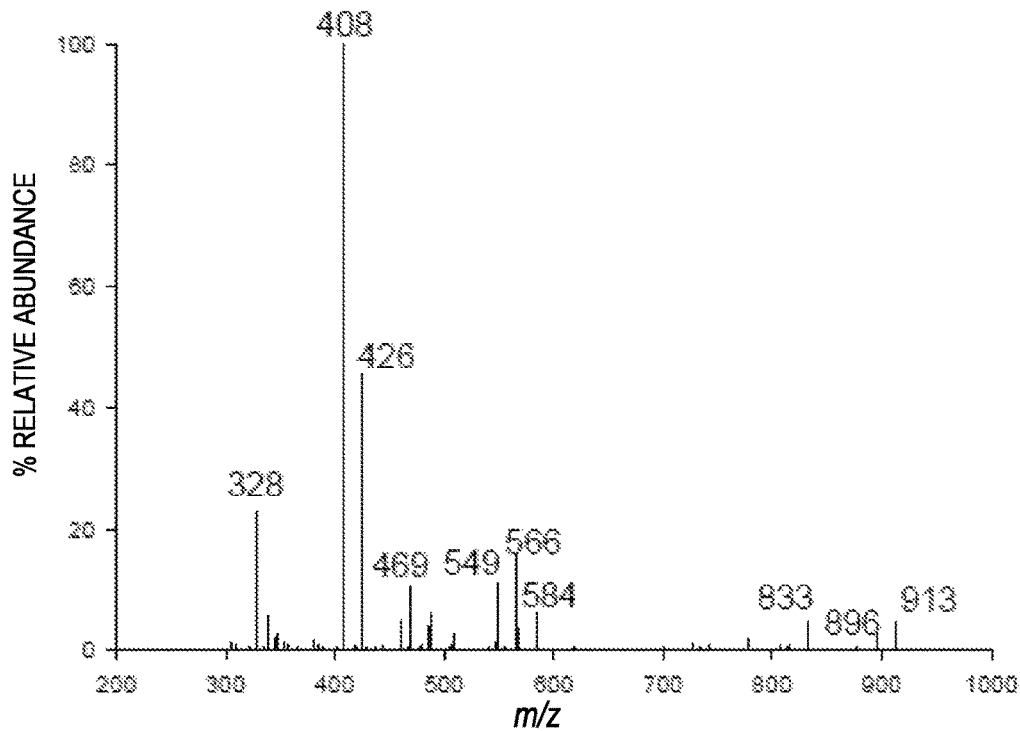
FIG. 2B2

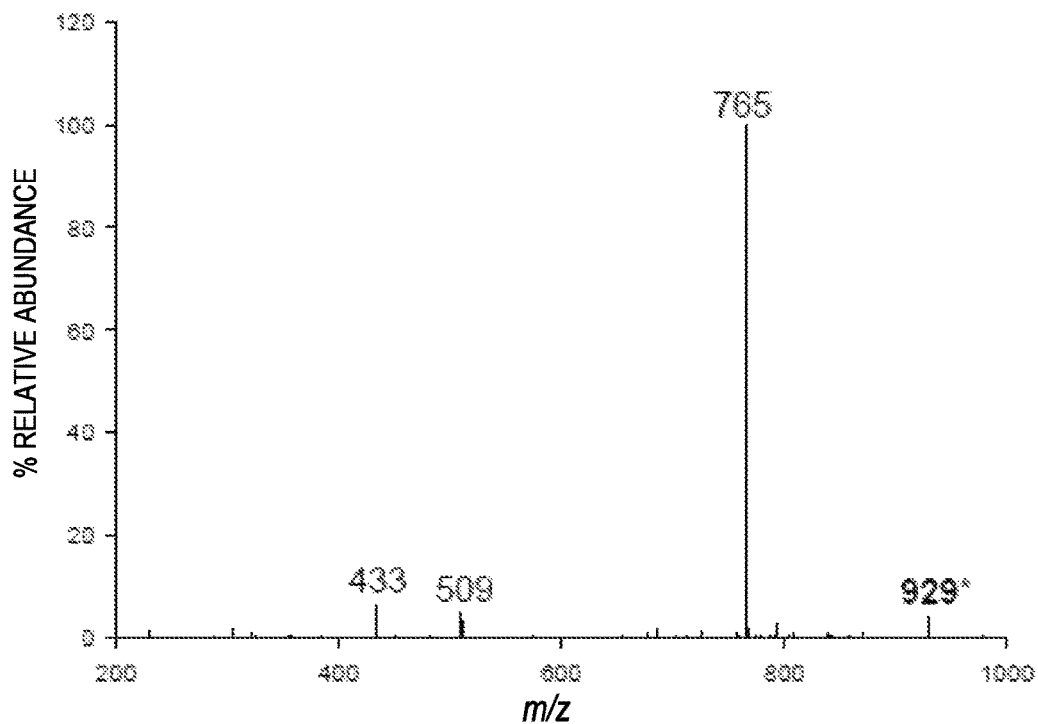
FIG. 2C1
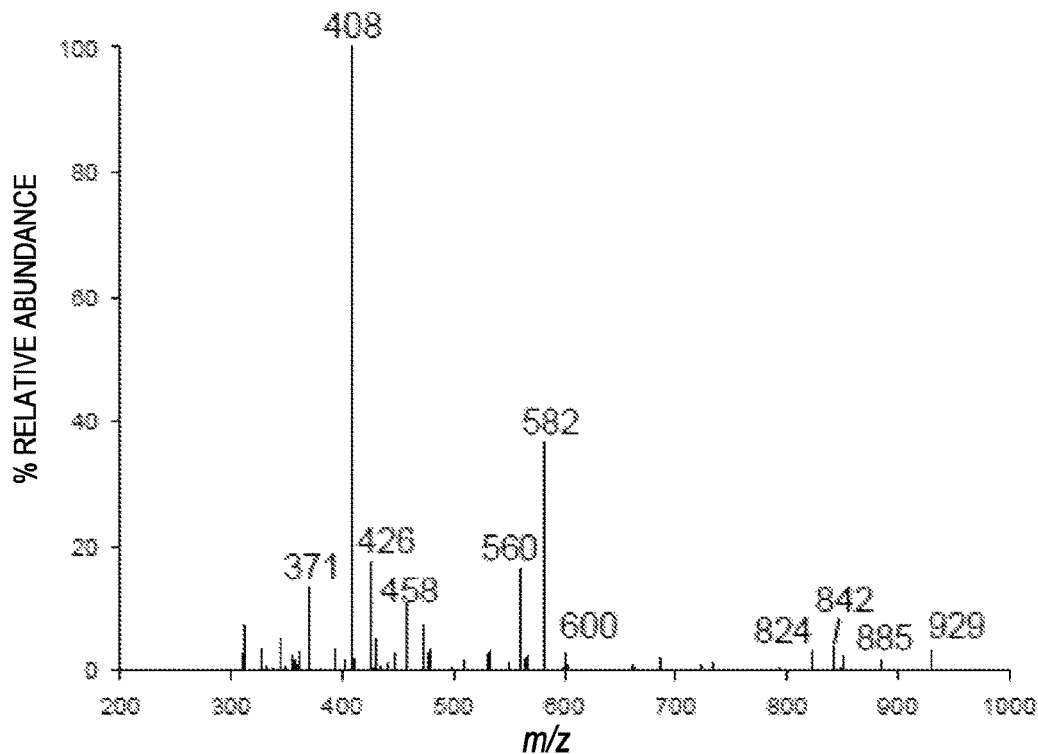
FIG. 2C2

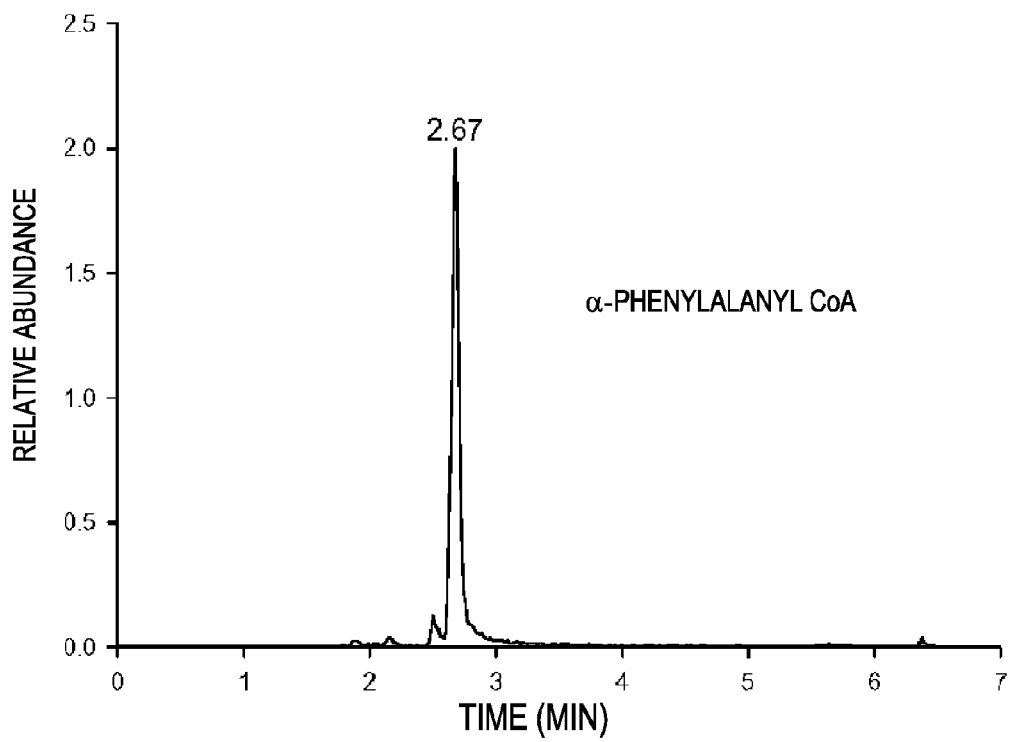
FIG. 3A1
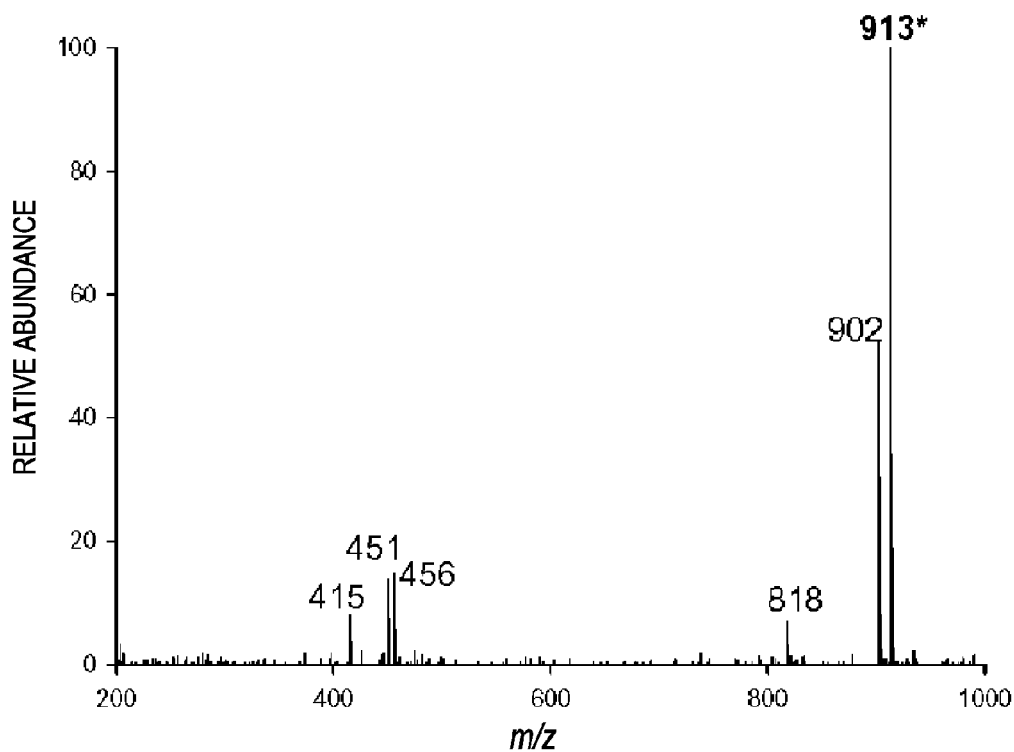
FIG. 3A2

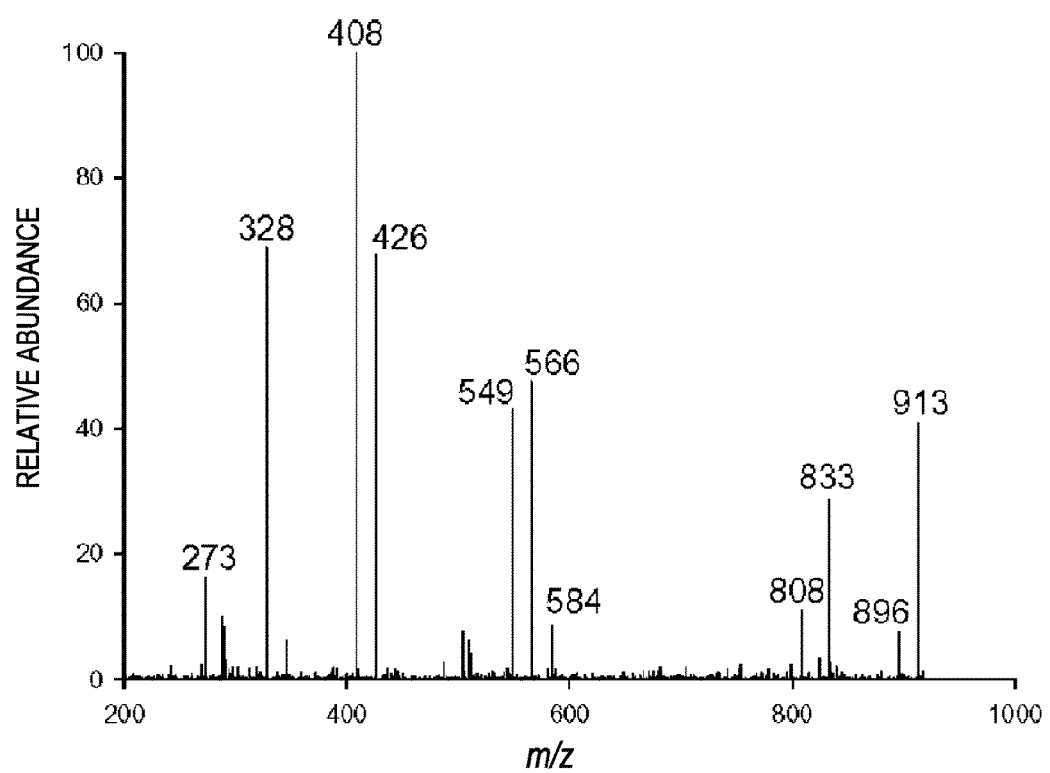
FIG. 3A3

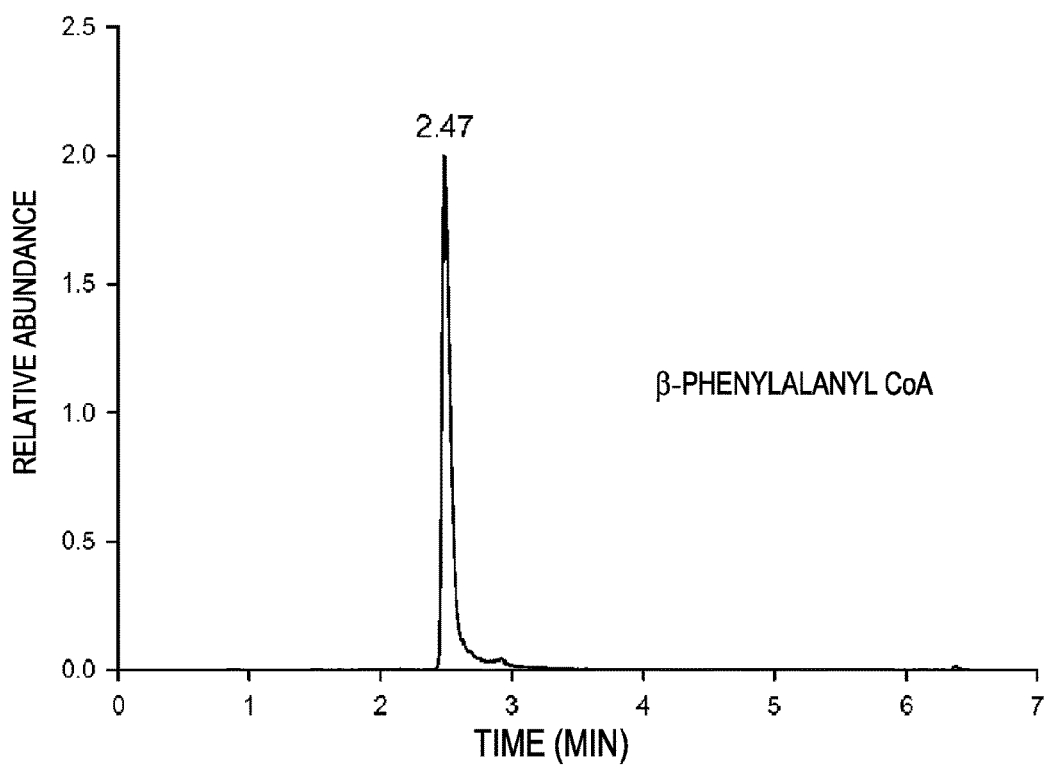
FIG. 3B1
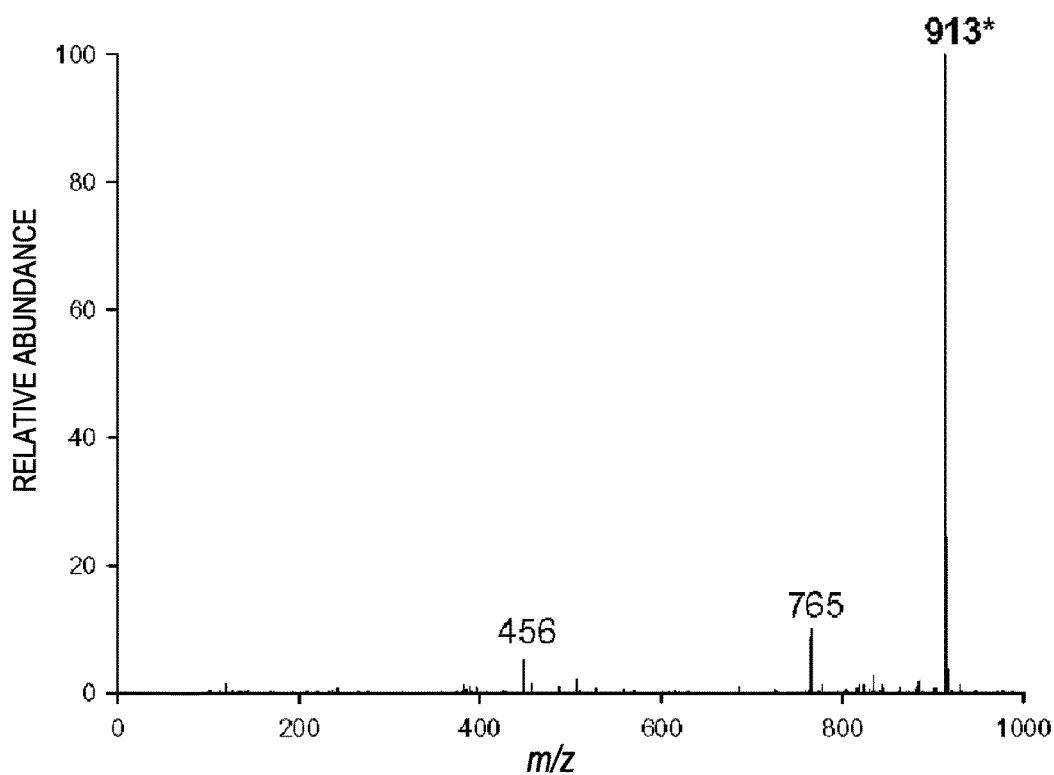
FIG. 3B2

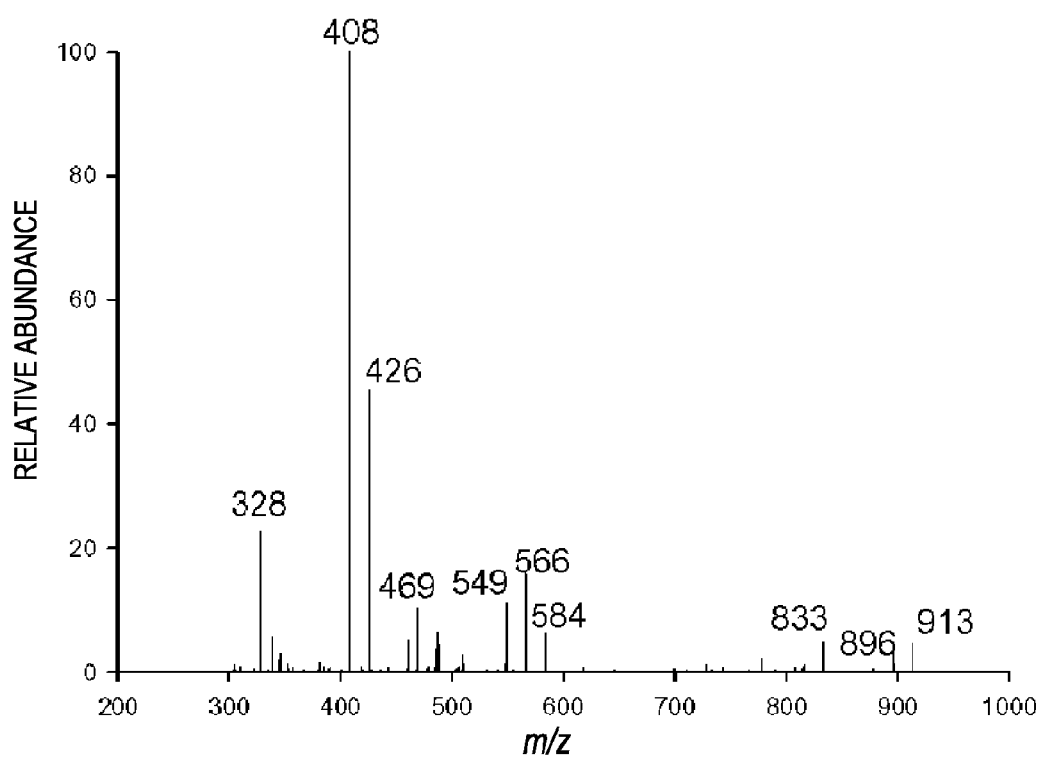
FIG. 3B3

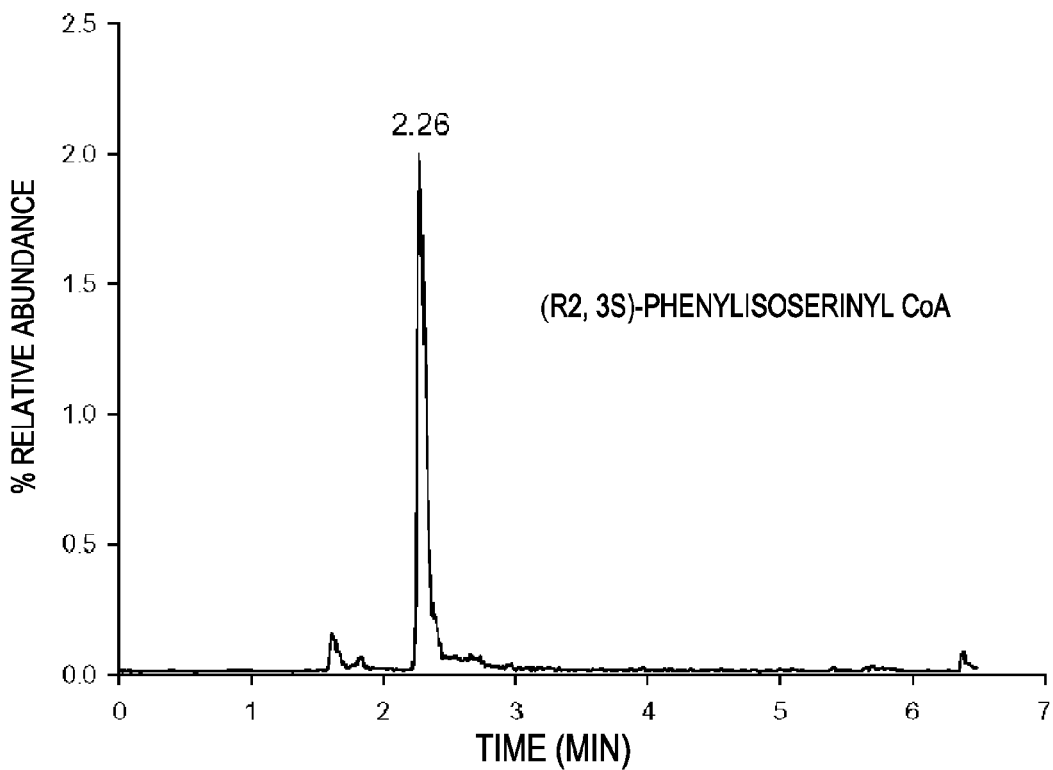
FIG. 3C1
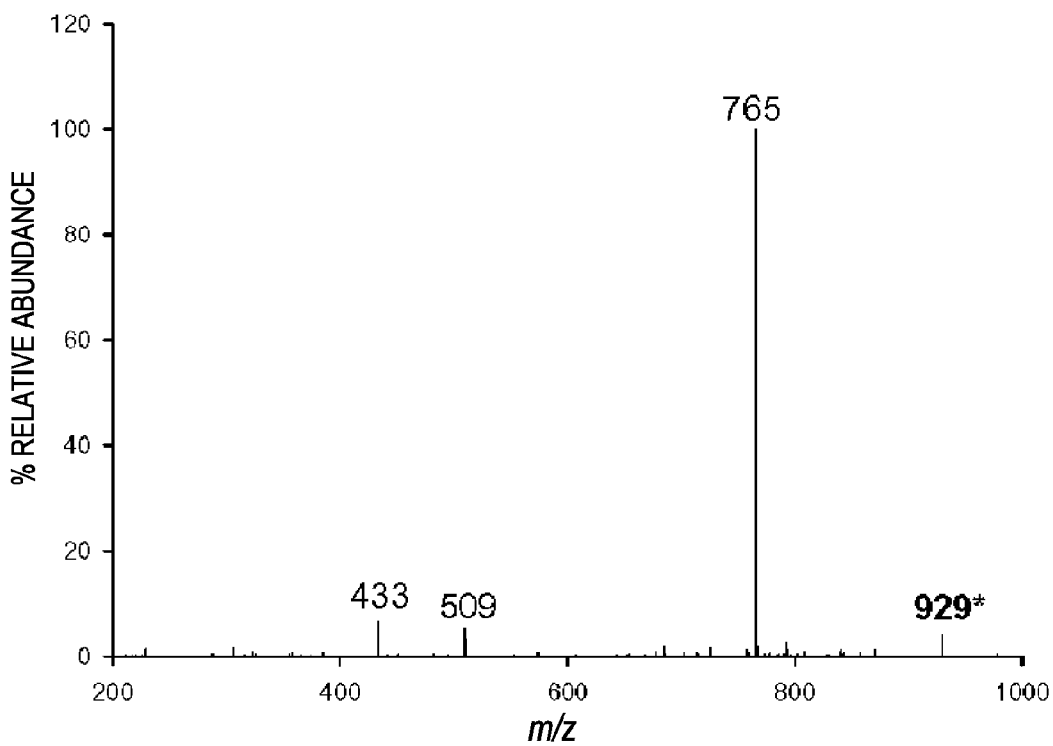
FIG. 3C2

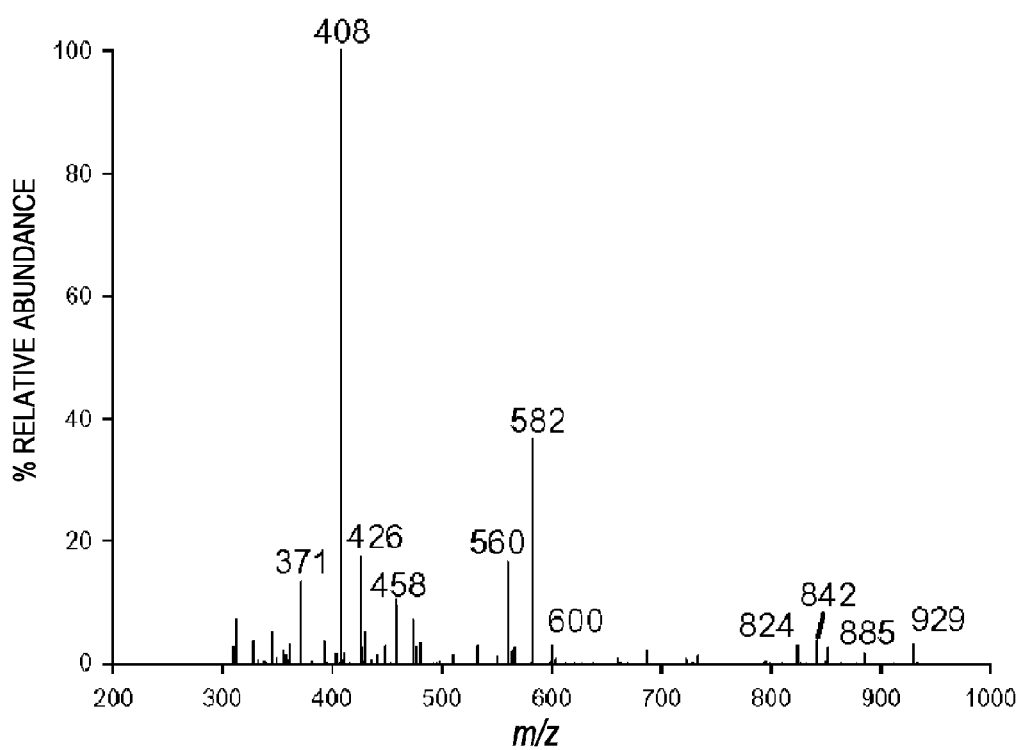
FIG. 3C3

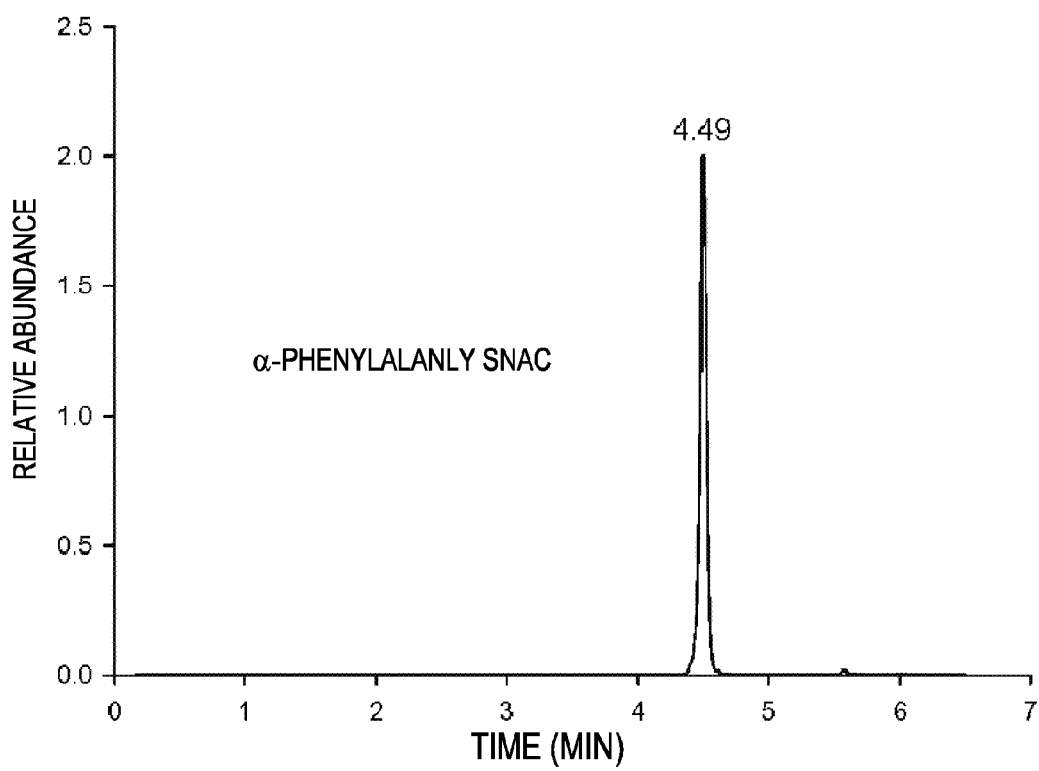
FIG. 6A1
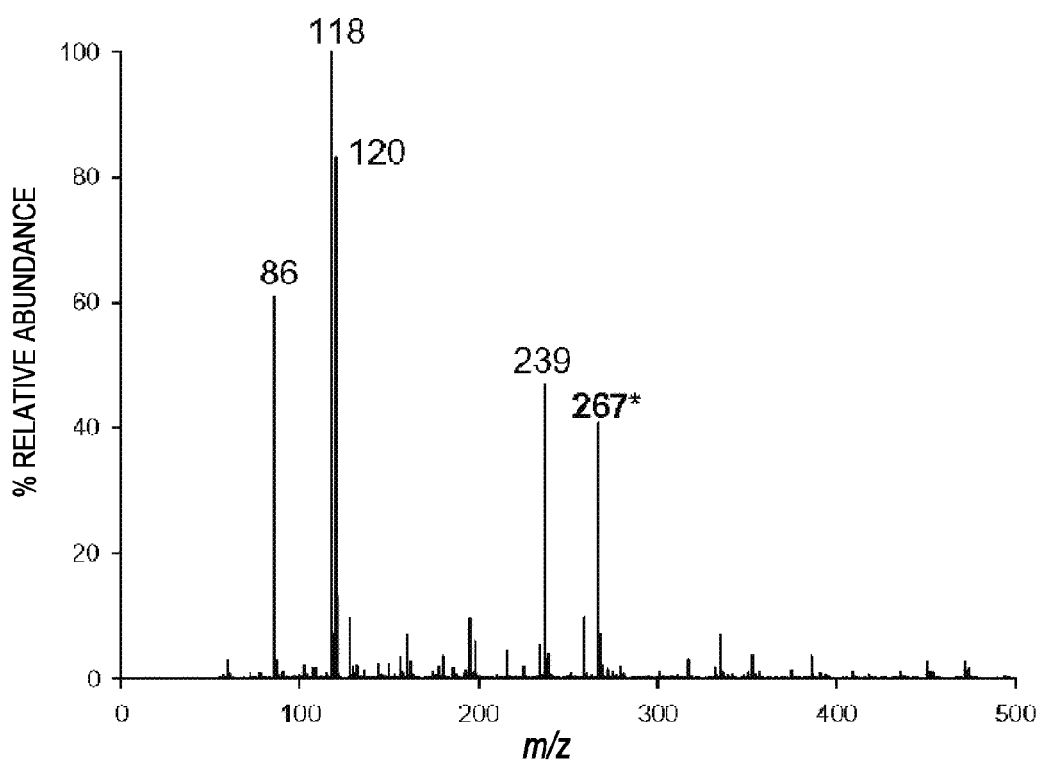
FIG. 6A2

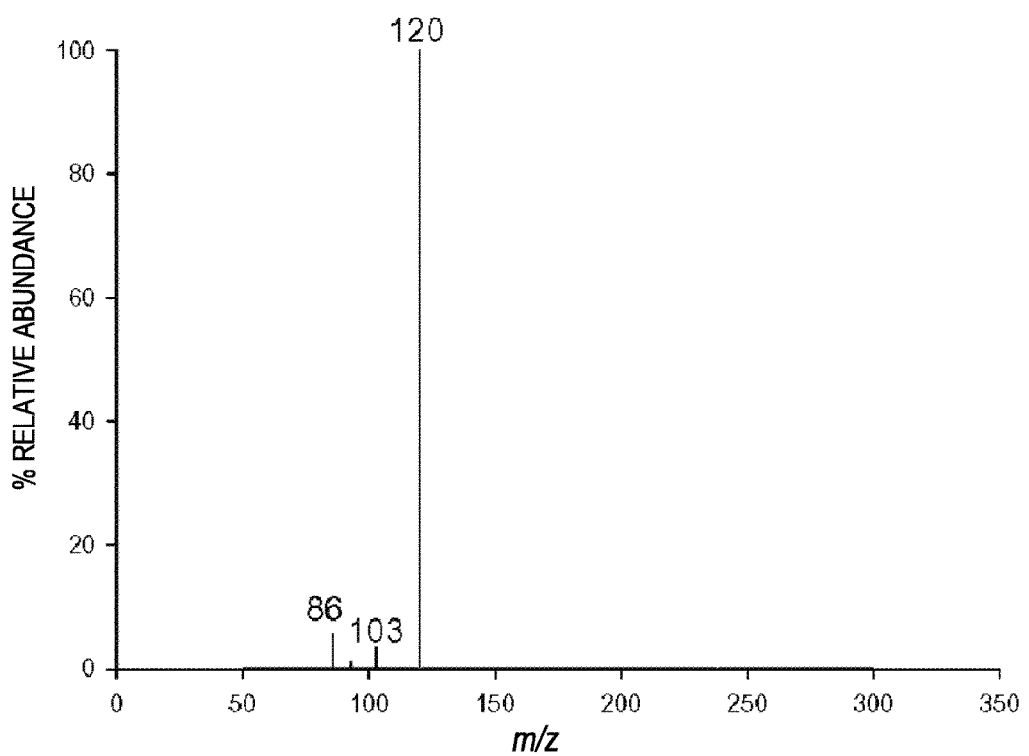
FIG. 6A3

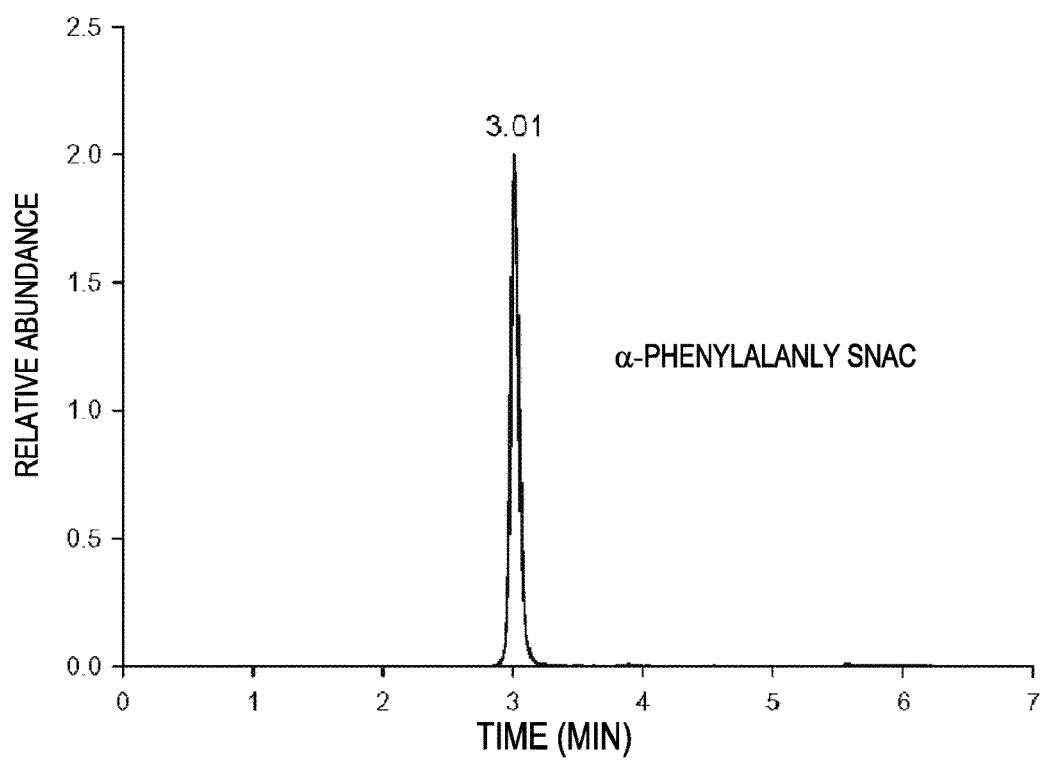
*FIG. 6B1*
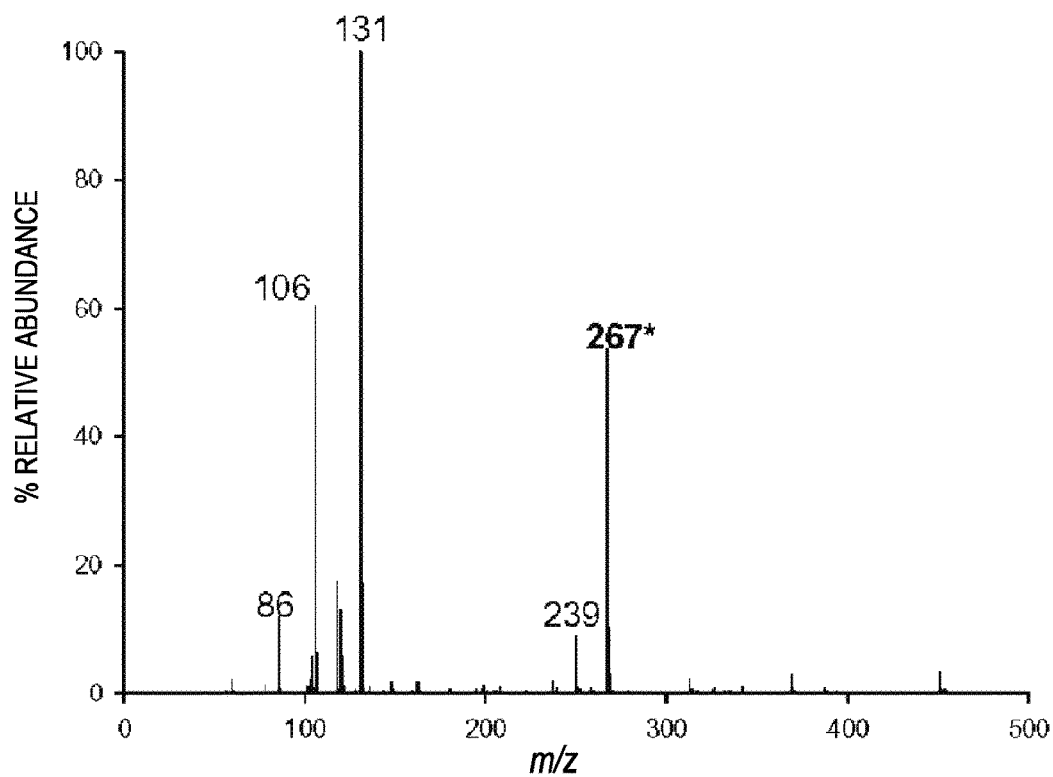
*FIG. 6B2*

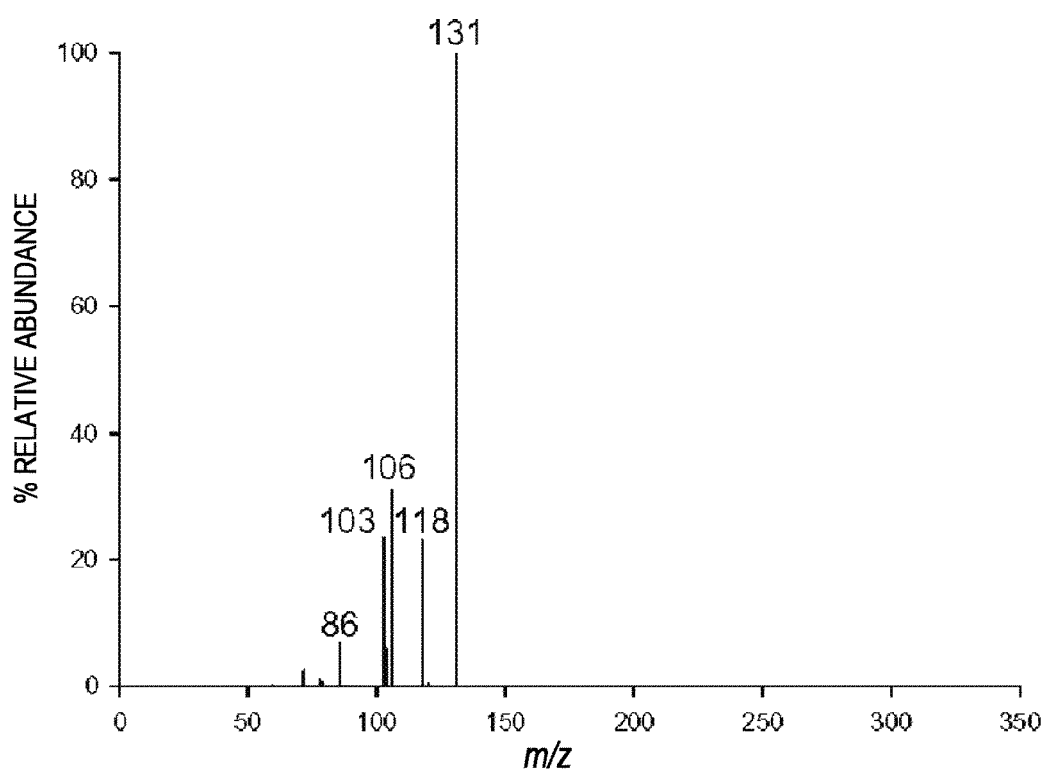
FIG. 6B3

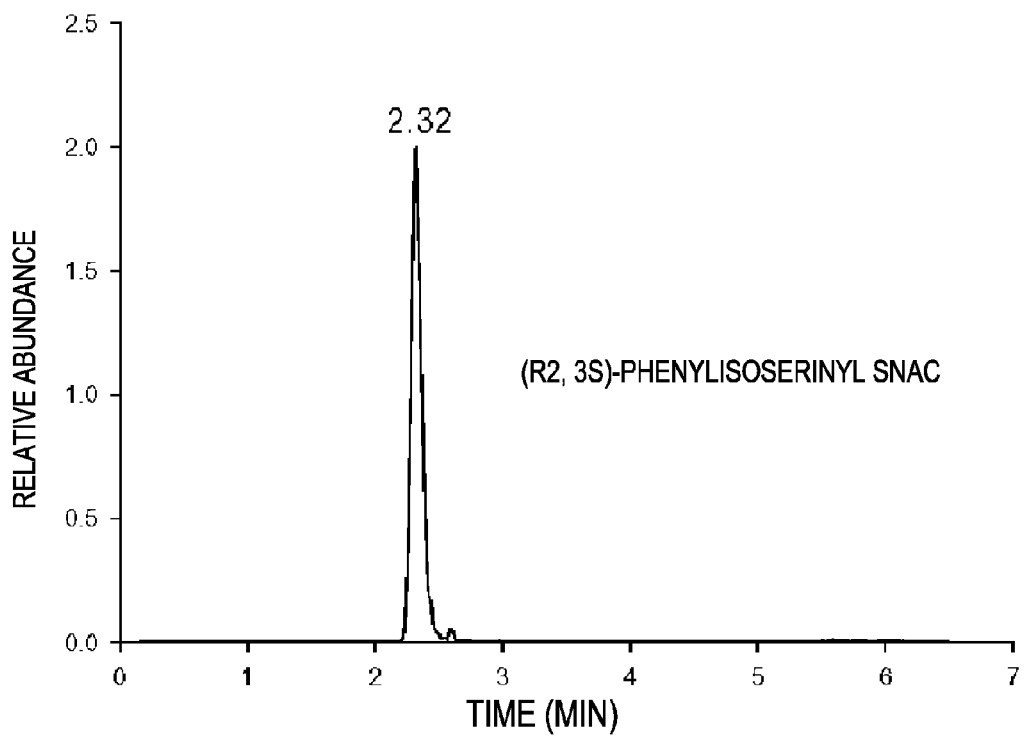
FIG. 6C1
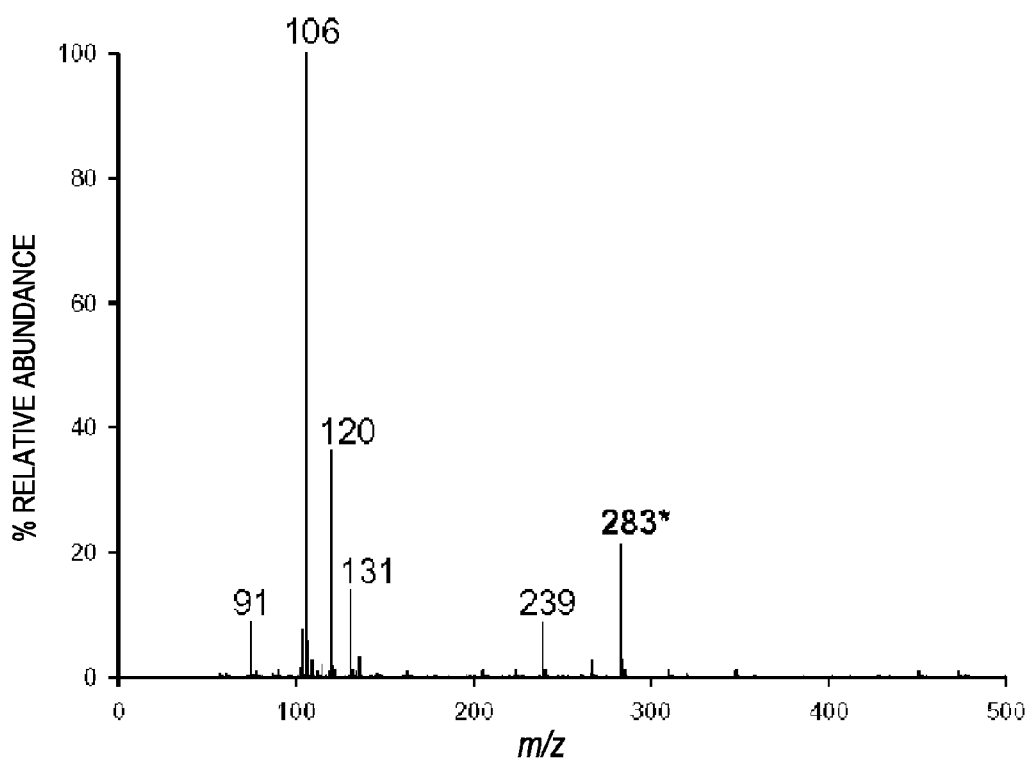
FIG. 6C2

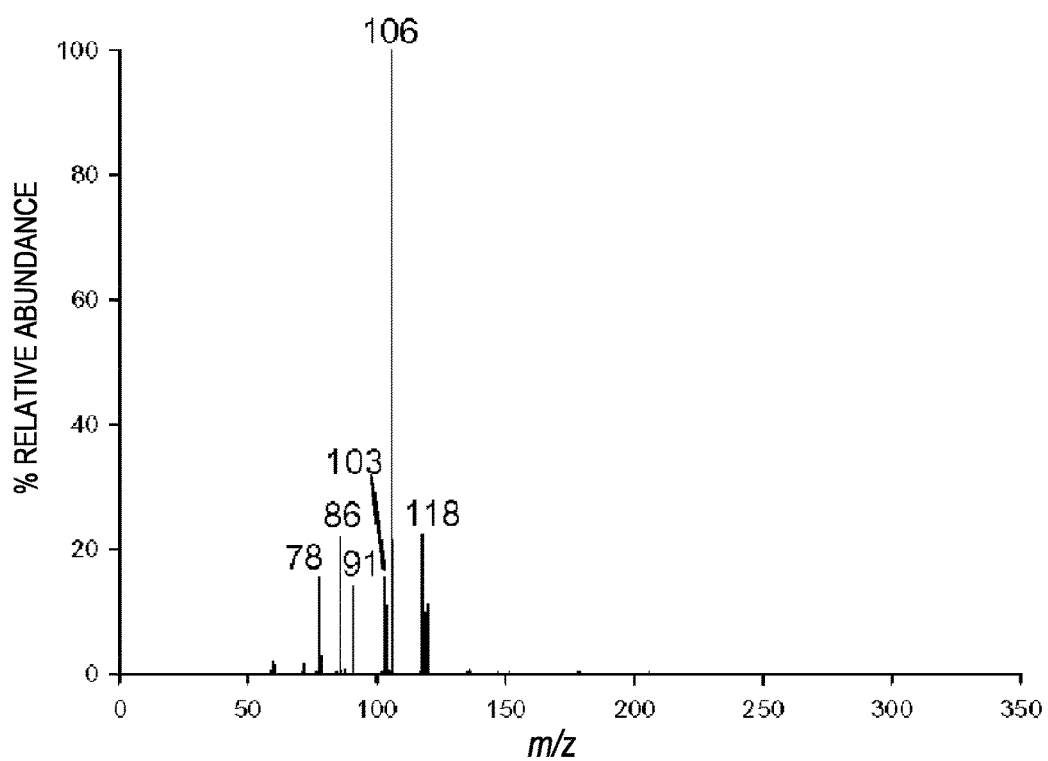
FIG. 6C3

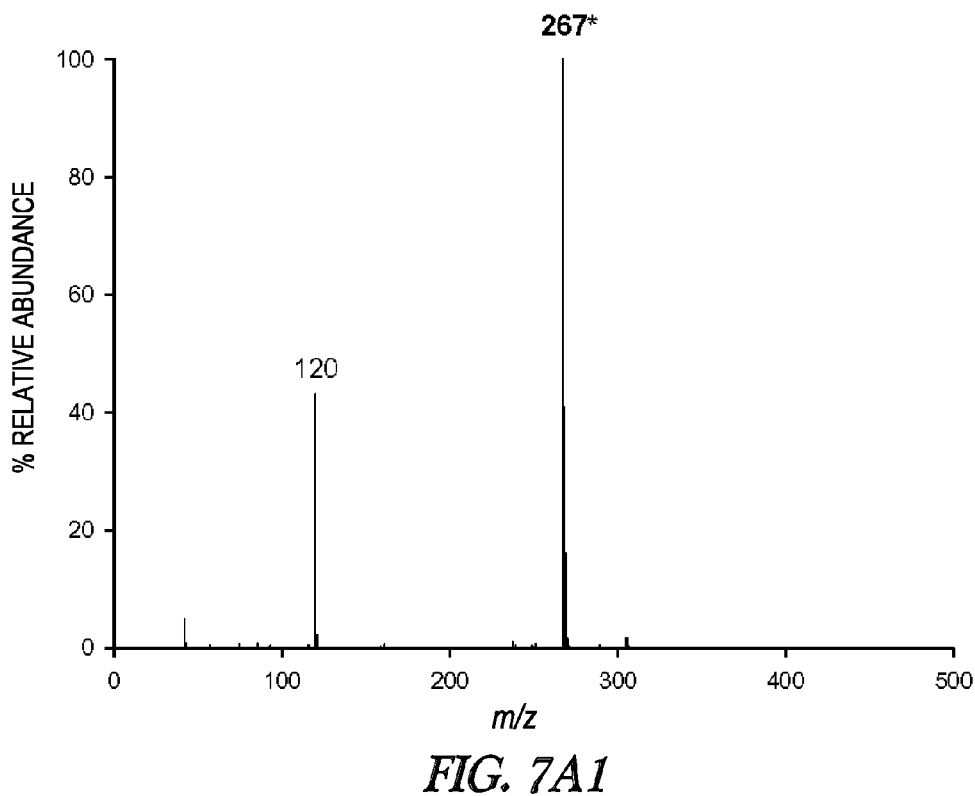
*FIG. 7A1*
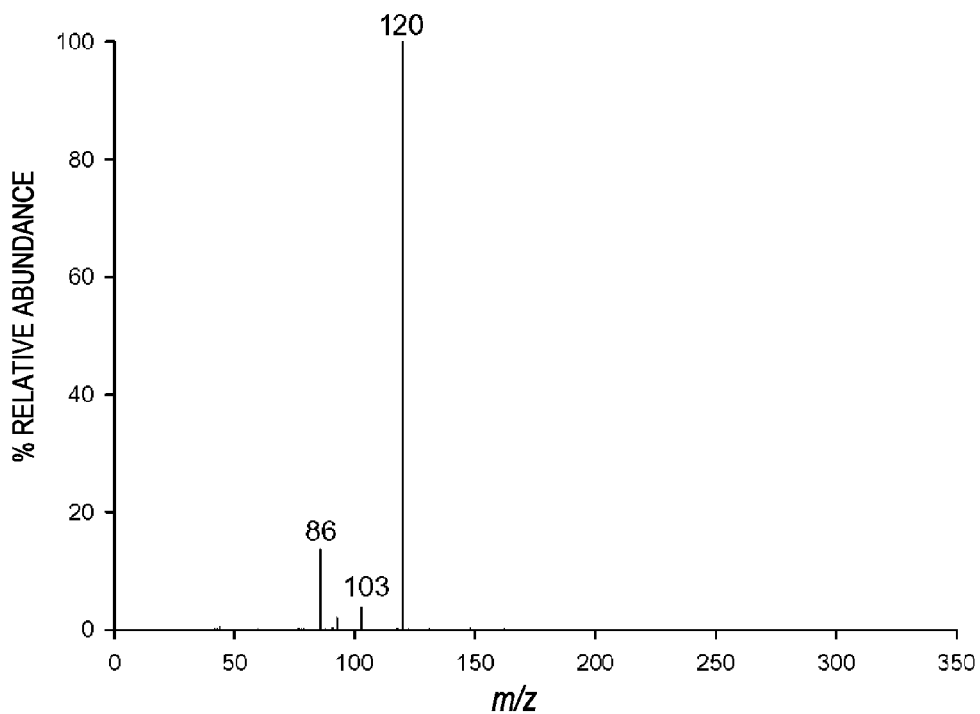
*FIG. 7A2*

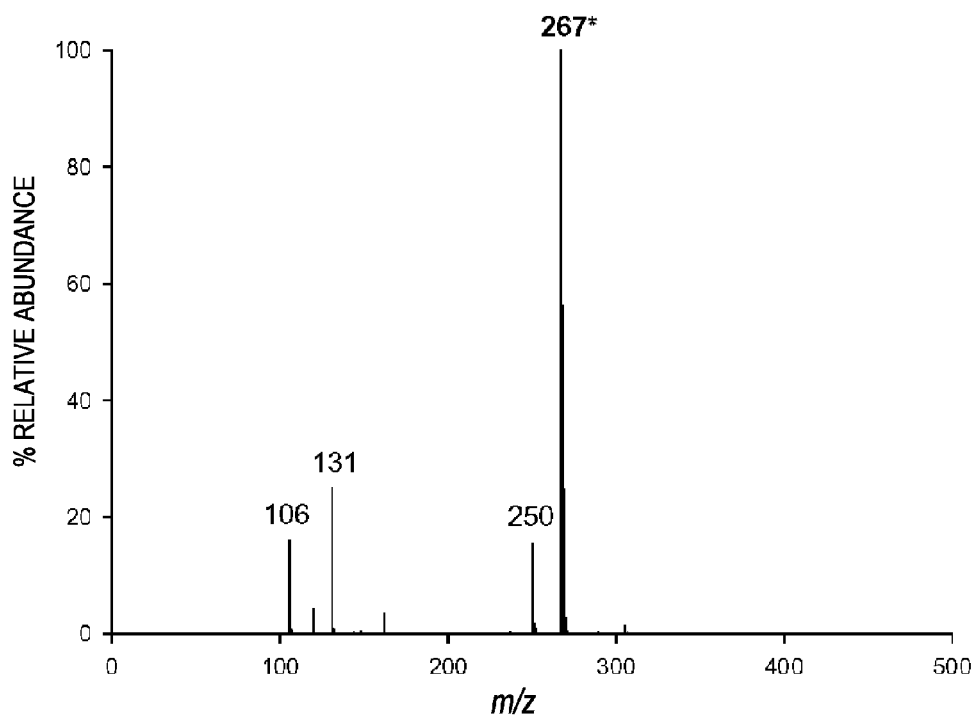
FIG. 7B1
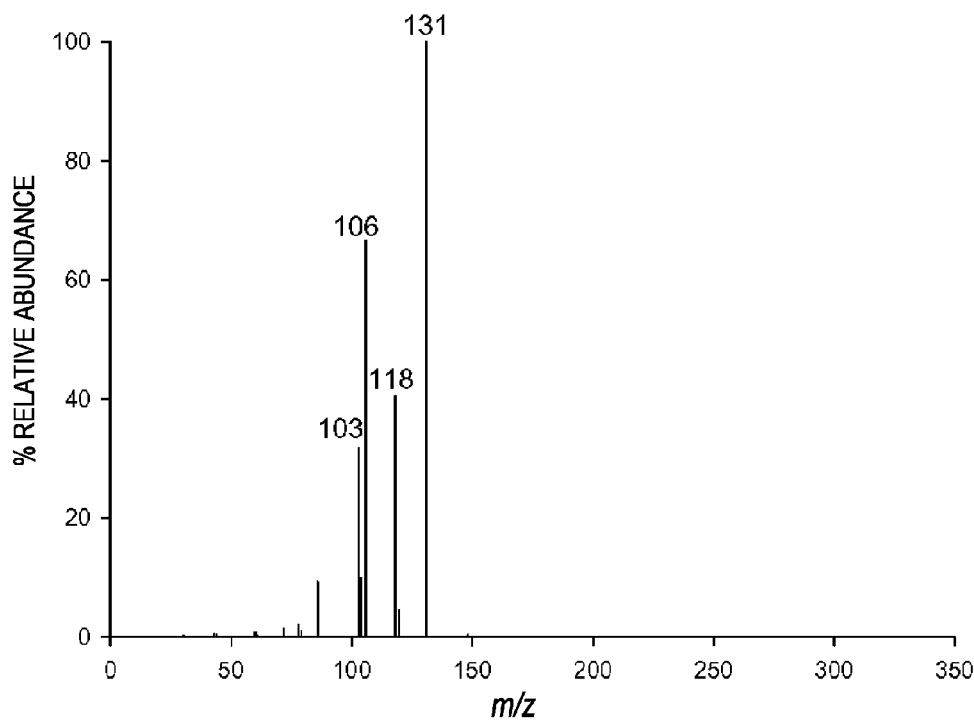
FIG. 7B2

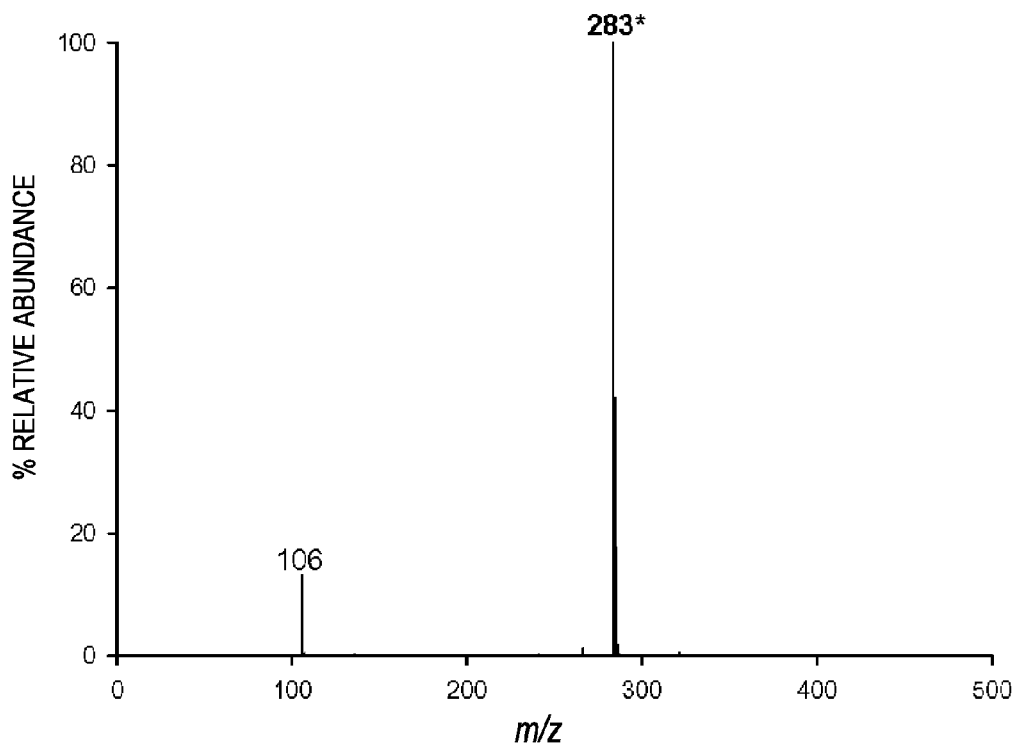
FIG. 7C1
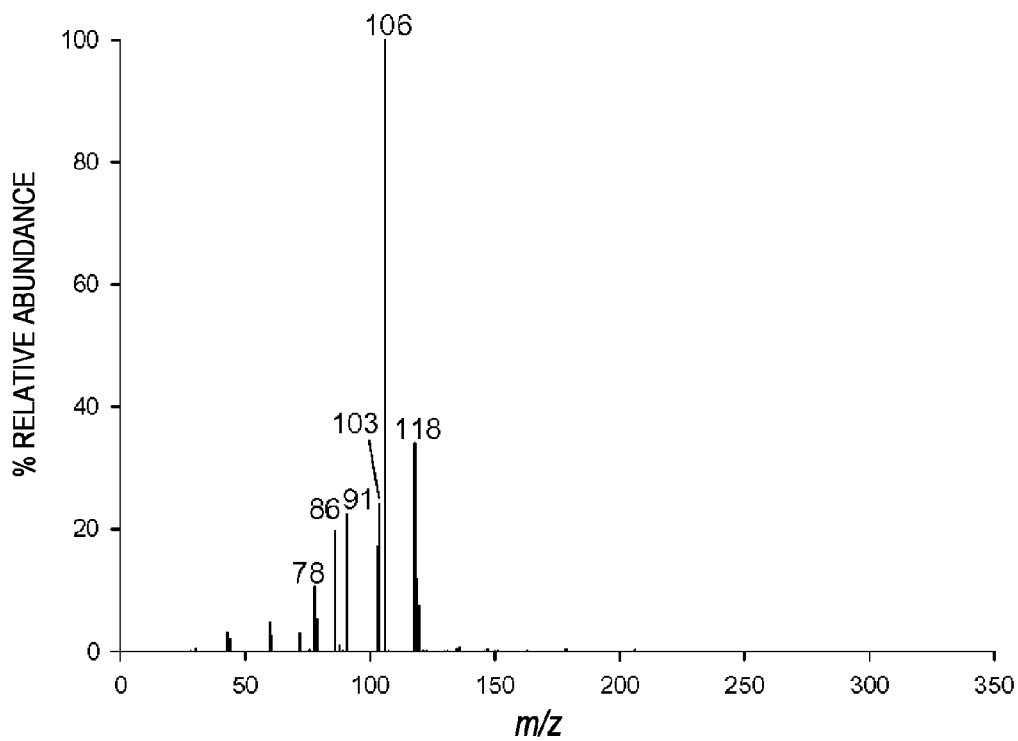
FIG. 7C2

SEQUENCE LISTING

<160> NUMBER OF SEQ ID NOS: 9

<210> SEQ ID NO 1
<211> LENGTH: 1092
<212> TYPE: PRT
<213> ORGANISM: Bacillus brevis

<400> SEQUENCE: 1

```
Met Val Ala Asn Gln Ala Asn Leu Ile Asp Asn Lys Arg Glu Leu Glu
1               5                   10                  15

Gln His Ala Leu Val Pro Tyr Ala Gln Gly Lys Ser Ile His Gln Leu
            20                  25                  30

Phe Glu Glu Gln Ala Glu Ala Phe Pro Asp Arg Val Ala Ile Val Phe
        35                  40                  45

Glu Asn Arg Arg Leu Ser Tyr Gln Glu Leu Asn Arg Lys Ala Asn Gln
    50                  55                  60

Leu Ala Arg Ala Leu Leu Glu Lys Gly Val Gln Thr Asp Ser Ile Val
65                  70                  75                  80

Gly Val Met Met Glu Lys Ser Ile Glu Asn Val Ile Ala Ile Leu Ala
                85                  90                  95

Val Leu Lys Ala Gly Gly Ala Tyr Val Pro Ile Asp Ile Glu Tyr Pro
            100                 105                 110

Arg Asp Arg Ile Gln Tyr Ile Leu Gln Asp Ser Gln Thr Lys Ile Val
        115                 120                 125

Leu Thr Gln Lys Ser Val Ser Gln Leu Val His Asp Val Gly Tyr Ser
    130                 135                 140

Gly Glu Val Val Val Leu Asp Glu Glu Gln Leu Asp Ala Arg Glu Thr
145                 150                 155                 160

Ala Asn Leu His Gln Pro Ser Lys Pro Thr Asp Leu Ala Tyr Val Ile
                165                 170                 175

Tyr Thr Ser Gly Thr Thr Gly Lys Pro Lys Gly Thr Met Leu Glu His
            180                 185                 190

Lys Gly Ile Ala Asn Leu Gln Ser Phe Phe Gln Asn Ser Phe Gly Val
        195                 200                 205
```

-continued

```
Thr Glu Gln Asp Arg Ile Gly Leu Phe Ala Ser Met Ser Phe Asp Ala
        210                 215                 220
Ser Val Trp Glu Met Phe Met Ala Leu Leu Ser Gly Ala Ser Leu Tyr
225                 230                 235                 240
Ile Leu Ser Lys Gln Thr Ile His Asp Phe Ala Ala Phe Glu His Tyr
                245                 250                 255
Leu Ser Glu Asn Glu Leu Thr Ile Ile Thr Leu Pro Pro Thr Tyr Leu
            260                 265                 270
Thr His Leu Thr Pro Glu Arg Ile Thr Ser Leu Arg Ile Met Ile Thr
        275                 280                 285
Ala Gly Ser Ala Ser Ala Pro Leu Val Asn Lys Trp Lys Asp Lys
290                 295                 300
Leu Arg Tyr Ile Asn Ala Tyr Gly Pro Thr Glu Thr Ser Ile Cys Ala
305                 310                 315                 320
Thr Ile Trp Glu Ala Pro Ser Asn Gln Leu Ser Val Gln Ser Val Pro
                325                 330                 335
Ile Gly Lys Pro Ile Gln Asn Thr His Ile Tyr Ile Val Asn Glu Asp
            340                 345                 350
Leu Gln Leu Leu Pro Thr Gly Ser Glu Gly Glu Leu Cys Ile Gly Gly
        355                 360                 365
Val Gly Leu Ala Arg Gly Tyr Trp Asn Arg Pro Asp Leu Thr Ala Glu
370                 375                 380
Lys Phe Val Asp Asn Pro Phe Val Pro Gly Glu Lys Met Tyr Arg Thr
385                 390                 395                 400
Gly Asp Leu Ala Lys Trp Leu Thr Asp Gly Thr Ile Glu Phe Leu Gly
                405                 410                 415
Arg Ile Asp His Gln Val Lys Ile Arg Gly His Arg Ile Glu Leu Gly
            420                 425                 430
Glu Ile Glu Ser Val Leu Leu Ala His Glu His Ile Thr Glu Ala Val
        435                 440                 445
Val Ile Ala Arg Glu Asp Gln His Ala Gly Gln Tyr Leu Cys Ala Tyr
450                 455                 460
Tyr Ile Ser Gln Gln Glu Ala Thr Pro Ala Gln Leu Arg Asp Tyr Ala
465                 470                 475                 480
Ala Gln Lys Leu Pro Ala Tyr Met Leu Pro Ser Tyr Phe Val Lys Leu
                485                 490                 495
Asp Lys Met Pro Leu Thr Pro Asn Asp Lys Ile Asp Arg Lys Ala Leu
            500                 505                 510
Pro Glu Pro Asp Leu Thr Ala Asn Gln Ser Gln Ala Ala Tyr His Pro
        515                 520                 525
Pro Arg Thr Glu Thr Glu Ser Ile Leu Val Ser Ile Trp Gln Asn Val
530                 535                 540
Leu Gly Ile Glu Lys Ile Gly Ile Arg Asp Asn Phe Tyr Ser Leu Gly
545                 550                 555                 560
Gly Asp Ser Ile Gln Ala Ile Gln Val Val Ala Arg Leu His Ser Tyr
                565                 570                 575
Gln Leu Lys Leu Glu Thr Lys Asp Leu Leu Asn Tyr Pro Thr Ile Glu
            580                 585                 590
Gln Val Ala Leu Phe Val Lys Ser Thr Thr Arg Lys Ser Asp Gln Gly
        595                 600                 605
Ile Ile Ala Gly Asn Val Pro Leu Thr Pro Ile Gln Lys Trp Phe Phe
610                 615                 620
```

-continued

```
Gly Lys Asn Phe Thr Asn Thr Gly His Trp Asn Gln Ser Ser Val Leu
625                 630                 635                 640

Tyr Arg Pro Glu Gly Phe Asp Pro Lys Val Ile Gln Ser Val Met Asp
            645                 650                 655

Lys Ile Ile Glu His His Asp Ala Leu Arg Met Val Tyr Gln His Glu
        660                 665                 670

Asn Gly Asn Val Val Gln His Asn Arg Gly Leu Gly Gly Gln Leu Tyr
    675                 680                 685

Asp Phe Phe Ser Tyr Asn Leu Thr Ala Gln Pro Asp Val Gln Gln Ala
690                 695                 700

Ile Glu Ala Glu Thr Gln Arg Leu His Ser Ser Met Asn Leu Gln Glu
705                 710                 715                 720

Gly Pro Leu Val Lys Val Ala Leu Phe Gln Thr Leu His Gly Asp His
            725                 730                 735

Leu Phe Leu Ala Ile His His Leu Val Val Asp Gly Ile Ser Trp Arg
        740                 745                 750

Ile Leu Phe Glu Asp Leu Ala Thr Gly Tyr Ala Gln Ala Leu Ala Gly
    755                 760                 765

Gln Ala Ile Ser Leu Pro Glu Lys Thr Asp Ser Phe Gln Ser Trp Ser
770                 775                 780

Gln Trp Leu Gln Glu Tyr Ala Asn Glu Ala Asp Leu Leu Ser Glu Ile
785                 790                 795                 800

Pro Tyr Trp Glu Ser Leu Glu Ser Gln Ala Lys Asn Val Ser Leu Pro
            805                 810                 815

Lys Asp Tyr Glu Val Thr Asp Cys Lys Gln Lys Ser Val Arg Asn Met
        820                 825                 830

Arg Ile Arg Leu His Pro Glu Glu Thr Glu Gln Leu Leu Lys His Ala
    835                 840                 845

Asn Gln Ala Tyr Gln Thr Glu Ile Asn Asp Leu Leu Leu Ala Ala Leu
850                 855                 860

Gly Leu Ala Phe Ala Glu Trp Ser Lys Leu Ala Gln Ile Val Ile His
865                 870                 875                 880

Leu Glu Gly His Gly Arg Glu Asp Ile Ile Glu Gln Ala Asn Val Ala
            885                 890                 895

Arg Thr Val Gly Trp Phe Thr Ser Gln Tyr Pro Val Leu Leu Asp Leu
        900                 905                 910

Lys Gln Thr Ala Pro Leu Ser Asp Tyr Ile Lys Leu Thr Lys Glu Asn
    915                 920                 925

Met Arg Lys Ile Pro Arg Lys Gly Ile Gly Tyr Asp Ile Leu Lys His
930                 935                 940

Val Thr Leu Pro Glu Asn Arg Gly Ser Leu Ser Phe Arg Val Gln Pro
945                 950                 955                 960

Glu Val Thr Phe Asn Tyr Leu Gly Gln Phe Asp Ala Asp Met Arg Thr
            965                 970                 975

Glu Leu Phe Thr Arg Ser Pro Tyr Ser Gly Asn Thr Leu Gly Ala
        980                 985                 990

Asp Gly Lys Asn Asn Leu Ser Pro Glu Ser Glu Val Tyr Thr Ala Leu
    995                 1000                1005

Asn Ile Thr Gly Leu Ile Glu Gly Gly Glu Leu Val Leu Thr Phe Ser
1010                1015                1020

Tyr Ser Ser Glu Gln Tyr Arg Glu Glu Ser Ile Gln Gln Leu Ser Gln
1025                1030                1035                1040

Ser Tyr Gln Lys His Leu Leu Ala Ile Ile Ala His Cys Thr Glu Lys
```

```
                    1045                1050                1055
Lys Glu Val Glu Arg Thr Pro Ser Asp Phe Ser Val Lys Gly Leu Gln
            1060                1065                1070

Met Glu Glu Met Asp Asp Ile Phe Glu Leu Leu Ala Asn Thr Leu Arg
            1075                1080                1085

Gly Ser Arg Ser
        1090

<210> SEQ ID NO 2
<211> LENGTH: 3303
<212> TYPE: DNA
<213> ORGANISM: Bacillus brevis

<400> SEQUENCE: 2
atggtagcaa atcaggccaa tctcatcgac aacaagcggg aactggagca gcatgcgcta      60
gttccatatg cacagggcaa gtcgatccat caattgttcg aggaacaagc agaggctttt     120
ccagaccgcg ttgccatcgt ttttgaaaac aggcggcttt cgtatcagga gttgaacagg     180
aaagccaatc aactggcaag agccttgctc gaaaaagggg tgcaaacaga cagcatcgtc     240
ggtgtgatga tggagaagtc catcgaaaat gtcatcgcga ttctggccgt tcttaaagca     300
ggcggagcct atgtgcccat cgacatcgaa tatccccgcg atcgcatcca atatattttg     360
caggatagtc aaacgaaaat cgtgcttacc caaaaaagcg tcagccagct cgtgcatgac     420
gtcgggtaca gcggagaggt agttgtactc gacgaagaac agttggacgc tcgcgagact     480
gccaatctgc accagcccag caagcctacg gatcttgcct atgtcattta cacctcaggc     540
acgacaggca agccaaaagg caccatgctt gaacataaag gcatcgccaa tttgcaatcc     600
tttttccaaa attcgtttgg cgtcaccgag caagacagga tcgggctttt tgccagcatg     660
tcgttcgacg catccgtttg ggaaatgttc atggctttgc tgtctggcgc cagcctgtac     720
atcctttcca acagacgat ccatgatttc gctgcatttg aacactattt gagtgaaaat     780
gaattgacca tcatcacact gccgccgact tatttgactc acctcacccc agagcgcatc     840
acctcgctac gcatcatgat tacggcagga tcagcttcct ccgcacccct ggtaaacaaa     900
tggaaagaca aactcaggta cataaatgca tacgcccga cggaaacgag catttgcgcg     960
acgatctggg aagccccgtc caatcagctc tccgtgcaat cggttccgat cggcaaaccg    1020
attcaaaata cacatattta tcgtcaatg aagacttgc agctactgcc gactggcagc    1080
gaaggcgaat gtgcatcgg cggagtcggc ttggcaagag ctattggaa tcggcccgac    1140 ttgaccgcag aaaaattcgt agacaatccg ttcgtaccag cgaaaaaat gtaccgcaca    1200 ggtgacttgg ccaaatggct gacggatgga acgatcgagt ttctcggcag aatcgaccat    1260
caggtgaaaa tcagaggtca tcgcatcgag cttggcgaaa tcgagtctgt tttgttggca    1320
catgaacaca tcacagaggc cgtggtcatt gccagagagg atcaacacgc gggacagtat    1380
ttgtgcgcct attatatttc gcaacaagaa gcaactcctg cgcagctcag agactacgcc    1440
gcccagaagc ttccggctta catgctgcca tcttatttcg tcaagctgga caaaatgccg    1500
cttacgccaa atgacaagat cgaccgcaaa gcgttgcccg agcctgatct tacggcaaac    1560
caaagccagg ctgcctacca tcctccgaga accgagacga atcgattct cgtctccatc    1620 tggcaaaacg ttttgggaat tgaaaagatc gggattcgcg ataatttta ctcgctcggc    1680 ggagattcga tccaagcgat ccaggtcgtg gctcgtctgc attcctatca attgaagcta    1740
gagacgaaag acttgctgaa ttacccgacg atcgagcagg ttgctctttt tgtcaagagc    1800
```

```
acgacgagaa aaagcgatca gggcatcatc gctggaaacg taccgcttac acccattcag    1860
aagtggtttt tcgggaaaaa ctttacgaat acaggccatt ggaaccaatc gtctgtgctc    1920
tatcgcccgg aaggctttga tcctaaagtc atccaaagtg tcatggacaa aatcatcgaa    1980
caccacgacg cgctccgcat ggtctatcag cacgaaaacg gaaatgtcgt tcagcacaac    2040
cgcggcttgg gtggacaatt atacgatttc ttctcttata atctgaccgc gcaaccagac    2100
gtccagcagg cgatcgaagc agagacgcaa cgtctgcaca gcagcatgaa tttgcaggaa    2160
ggacctctgg tgaaggttgc cttatttcag acgttacatg gcgatcattt gtttctcgca    2220
attcatcatt tggtcgtgga tggcatttcc tggcgcattt tgtttgaaga tttggcaacc    2280
ggatacgcgc aggcacttgc agggcaagcg atcagtctgc ccgaaaaaac ggattctttt    2340
caaagctggt cacaatggtt gcaagaatat gcgaacgagg cggatttgct gagcgagatt    2400
ccgtactggg agagtctcga atcgcaagca aaaaatgtgt ccctgccgaa agactatgaa    2460
gtgaccgact gcaaacaaaa gagcgtgcga acatgcggat acggctgcac cccggaagag    2520
accgagcagt tgttgaagca cgccaatcag gcctatcaaa cggaaatcaa cgatctgttg    2580
ttggcggcgc tcggcttggc ttttgcggag tggagcaagc ttgcgcaaat cgtcattcat    2640
ttggaggggc acgggcgcga ggacatcatc gaacaggcaa acgtggccag aacggtcgga    2700
tggtttacgt cgcaatatcc ggtattgctc gacttgaagc aaaccgctcc cttgtccgac    2760
tatatcaagc tcaccaaaga gaatatgcgg aagattcctc gtaaagggat cggttacgac    2820
atcttgaagc atgtgacact tccagaaaat cgcggttcct tatccttccg cgtgcagccg    2880
gaagtgacgt caactactt gggacagttt gatgcggaca tgagaacgga actgtttacc    2940
cgctcaccct acagcggcgg caacacgtta ggcgcagatg gcaaaaacaa tctgagtcct    3000
gagtcagagg tgtacaccgc tttgaatata accggattga ttgaaggcgg agagctcgtc    3060
ctcacattct cttacagctc ggagcagtat cgggaagagt ccatccagca attgagccaa    3120
agttatcaaa agcatctgct tgccatcatc gcgcattgca ccgagaaaaa agaagtagag    3180
cgaacgccca gcgatttcag cgtcaaaggt ctccaaatgg aagaaatgga cgatatcttc    3240
gaattgcttg caaatacact gcgcggatcc agatctcatc accatcacca tcactaagct    3300
taa                                                                  3303
```

<210> SEQ ID NO 3
<211> LENGTH: 1098
<212> TYPE: PRT
<213> ORGANISM: Bacillus brevis

<400> SEQUENCE: 3

```
Met Val Ala Asn Gln Ala Asn Leu Ile Asp Asn Lys Arg Glu Leu Glu
1               5                   10                  15

Gln His Ala Leu Val Pro Tyr Ala Gln Gly Lys Ser Ile His Gln Leu
            20                  25                  30

Phe Glu Glu Gln Ala Glu Ala Phe Pro Asp Arg Val Ala Ile Val Phe
        35                  40                  45

Glu Asn Arg Arg Leu Ser Tyr Gln Glu Leu Asn Arg Lys Ala Asn Gln
    50                  55                  60

Leu Ala Arg Ala Leu Leu Glu Lys Gly Val Gln Thr Asp Ser Ile Val
65                  70                  75                  80

Gly Val Met Met Glu Lys Ser Ile Glu Asn Val Ile Ala Ile Leu Ala
                85                  90                  95

Val Leu Lys Ala Gly Gly Ala Tyr Val Pro Ile Asp Ile Glu Tyr Pro
```

-continued

```
                100             105             110
Arg Asp Arg Ile Gln Tyr Ile Leu Gln Asp Ser Gln Thr Lys Ile Val
            115             120             125
Leu Thr Gln Lys Ser Val Ser Gln Leu Val His Asp Val Gly Tyr Ser
        130             135             140
Gly Glu Val Val Val Leu Asp Glu Glu Gln Leu Asp Ala Arg Glu Thr
145             150             155             160
Ala Asn Leu His Gln Pro Ser Lys Pro Thr Asp Leu Ala Tyr Val Ile
            165             170             175
Tyr Thr Ser Gly Thr Thr Gly Lys Pro Lys Gly Thr Met Leu Glu His
        180             185             190
Lys Gly Ile Ala Asn Leu Gln Ser Phe Phe Gln Asn Ser Phe Gly Val
        195             200             205
Thr Glu Gln Asp Arg Ile Gly Leu Phe Ala Ser Met Ser Phe Asp Ala
        210             215             220
Ser Val Trp Glu Met Phe Met Ala Leu Leu Ser Gly Ala Ser Leu Tyr
225             230             235             240
Ile Leu Ser Lys Gln Thr Ile His Asp Phe Ala Ala Phe Glu His Tyr
            245             250             255
Leu Ser Glu Asn Glu Leu Thr Ile Ile Thr Leu Pro Pro Thr Tyr Leu
        260             265             270
Thr His Leu Thr Pro Glu Arg Ile Thr Ser Leu Arg Ile Met Ile Thr
        275             280             285
Ala Gly Ser Ala Ser Ser Ala Pro Leu Val Asn Lys Trp Lys Asp Lys
        290             295             300
Leu Arg Tyr Ile Asn Ala Tyr Gly Pro Thr Glu Thr Ser Ile Cys Ala
305             310             315             320
Thr Ile Trp Glu Ala Pro Ser Asn Gln Leu Ser Val Gln Ser Val Pro
            325             330             335
Ile Gly Lys Pro Ile Gln Asn Thr His Ile Tyr Ile Val Asn Glu Asp
            340             345             350
Leu Gln Leu Leu Pro Thr Gly Ser Glu Gly Glu Leu Cys Ile Gly Gly
        355             360             365
Val Gly Leu Ala Arg Gly Tyr Trp Asn Arg Pro Asp Leu Thr Ala Glu
        370             375             380
Lys Phe Val Asp Asn Pro Phe Val Pro Gly Glu Lys Met Tyr Arg Thr
385             390             395             400
Gly Asp Leu Ala Lys Trp Leu Thr Asp Gly Thr Ile Glu Phe Leu Gly
            405             410             415
Arg Ile Asp His Gln Val Lys Ile Arg Gly His Arg Ile Glu Leu Gly
            420             425             430
Glu Ile Glu Ser Val Leu Leu Ala His Glu His Ile Thr Glu Ala Val
        435             440             445
Val Ile Ala Arg Glu Asp Gln His Ala Gly Gln Tyr Leu Cys Ala Tyr
        450             455             460
Tyr Ile Ser Gln Gln Glu Ala Thr Pro Ala Gln Leu Arg Asp Tyr Ala
465             470             475             480
Ala Gln Lys Leu Pro Ala Tyr Met Leu Pro Ser Tyr Phe Val Lys Leu
            485             490             495
Asp Lys Met Pro Leu Thr Pro Asn Asp Lys Ile Asp Arg Lys Ala Leu
            500             505             510
Pro Glu Pro Asp Leu Thr Ala Asn Gln Ser Gln Ala Ala Tyr His Pro
        515             520             525
```

-continued

Pro Arg Thr Glu Thr Glu Ser Ile Leu Val Ser Ile Trp Gln Asn Val
    530                 535                 540

Leu Gly Ile Glu Lys Ile Gly Ile Arg Asp Asn Phe Tyr Ser Leu Gly
545                 550                 555                 560

Gly Asp Ala Ile Gln Ala Ile Gln Val Val Ala Arg Leu His Ser Tyr
                565                 570                 575

Gln Leu Lys Leu Glu Thr Lys Asp Leu Leu Asn Tyr Pro Thr Ile Glu
            580                 585                 590

Gln Val Ala Leu Phe Val Lys Ser Thr Thr Arg Lys Ser Asp Gln Gly
        595                 600                 605

Ile Ile Ala Gly Asn Val Pro Leu Thr Pro Ile Gln Lys Trp Phe Phe
    610                 615                 620

Gly Lys Asn Phe Thr Asn Thr Gly His Trp Asn Gln Ser Ser Val Leu
625                 630                 635                 640

Tyr Arg Pro Glu Gly Phe Asp Pro Lys Val Ile Gln Ser Val Met Asp
                645                 650                 655

Lys Ile Ile Glu His His Asp Ala Leu Arg Met Val Tyr Gln His Glu
            660                 665                 670

Asn Gly Asn Val Val Gln His Asn Arg Gly Leu Gly Gly Gln Leu Tyr
        675                 680                 685

Asp Phe Phe Ser Tyr Asn Leu Thr Ala Gln Pro Asp Val Gln Gln Ala
    690                 695                 700

Ile Glu Ala Glu Thr Gln Arg Leu His Ser Ser Met Asn Leu Gln Glu
705                 710                 715                 720

Gly Pro Leu Val Lys Val Ala Leu Phe Gln Thr Leu His Gly Asp His
                725                 730                 735

Leu Phe Leu Ala Ile His His Leu Val Val Asp Gly Ile Ser Trp Arg
            740                 745                 750

Ile Leu Phe Glu Asp Leu Ala Thr Gly Tyr Ala Gln Ala Leu Ala Gly
        755                 760                 765

Gln Ala Ile Ser Leu Pro Glu Lys Thr Asp Ser Phe Gln Ser Trp Ser
    770                 775                 780

Gln Trp Leu Gln Glu Tyr Ala Asn Glu Ala Asp Leu Leu Ser Glu Ile
785                 790                 795                 800

Pro Tyr Trp Glu Ser Leu Glu Ser Gln Ala Lys Asn Val Ser Leu Pro
                805                 810                 815

Lys Asp Tyr Glu Val Thr Asp Cys Lys Gln Lys Ser Val Arg Asn Met
            820                 825                 830

Arg Ile Arg Leu His Pro Glu Thr Glu Gln Leu Leu Lys His Ala
        835                 840                 845

Asn Gln Ala Tyr Gln Thr Glu Ile Asn Asp Leu Leu Leu Ala Ala Leu
    850                 855                 860

Gly Leu Ala Phe Ala Glu Trp Ser Lys Leu Ala Gln Ile Val Ile His
865                 870                 875                 880

Leu Glu Gly His Gly Arg Glu Asp Ile Ile Glu Gln Ala Asn Val Ala
                885                 890                 895

Arg Thr Val Gly Trp Phe Thr Ser Gln Tyr Pro Val Leu Leu Asp Leu
            900                 905                 910

Lys Gln Thr Ala Pro Leu Ser Asp Tyr Ile Lys Leu Thr Lys Glu Asn
        915                 920                 925

Met Arg Lys Ile Pro Arg Lys Gly Ile Gly Tyr Asp Ile Leu Lys His
    930                 935                 940

```
Val Thr Leu Pro Glu Asn Arg Gly Ser Leu Ser Phe Arg Val Gln Pro
945                 950                 955                 960

Glu Val Thr Phe Asn Tyr Leu Gly Gln Phe Asp Ala Asp Met Arg Thr
            965                 970                 975

Glu Leu Phe Thr Arg Ser Pro Tyr Ser Gly Gly Asn Thr Leu Gly Ala
                980                 985                 990

Asp Gly Lys Asn Asn Leu Ser Pro Glu Ser Glu Val Tyr Thr Ala Leu
            995                 1000                1005

Asn Ile Thr Gly Leu Ile Glu Gly Gly Glu Leu Val Leu Thr Phe Ser
    1010                1015                1020

Tyr Ser Ser Glu Gln Tyr Arg Glu Glu Ser Ile Gln Gln Leu Ser Gln
1025                1030                1035                1040

Ser Tyr Gln Lys His Leu Leu Ala Ile Ile Ala His Cys Thr Glu Lys
            1045                1050                1055

Lys Glu Val Glu Arg Thr Pro Ser Asp Phe Ser Val Lys Gly Leu Gln
            1060                1065                1070

Met Glu Glu Met Asp Asp Ile Phe Glu Leu Leu Ala Asn Thr Leu Arg
        1075                1080                1085

Gly Ser Arg Ser His His His His His His
    1090                1095
```

<210> SEQ ID NO 4
<211> LENGTH: 3303
<212> TYPE: DNA
<213> ORGANISM: Bacillus brevis

<400> SEQUENCE: 4

```
atggtagcaa atcaggccaa tctcatcgac aacaagcggg aactggagca gcatgcgcta      60
gttccatatg cacagggcaa gtcgatccat caattgttcg aggaacaagc agaggctttt     120
ccagaccgcg ttgccatcgt ttttgaaaac aggcggcttt cgtatcagga gttgaacagg     180
aaagccaatc aactggcaag agccttgctc gaaaaagggg tgcaaacaga cagcatcgtc     240
ggtgtgatga tggagaagtc catcgaaaat gtcatcgcga ttctggccgt tcttaaagca     300
ggcggagcct atgtgcccat cgacatcgaa tatccccgcg atcgcatcca atatattttg     360
caggatagtc aaacgaaaat cgtgcttacc caaaaaagcg tcagccagct cgtgcatgac     420
gtcgggtaca gcgagagagt agttgtactc gacgaagaac agttggacgc tcgcgagact     480
gccaatctgc accagcccag caagcctacg gatcttgcct atgtcattta cacctcaggc     540
acgacaggca agccaaaagg caccatgctt gaacataaag gcatcgccaa tttgcaatcc     600
tttttccaaa attcgtttgg cgtcaccgag caagacagga tcgggctttt tgccagcatg     660
tcgttcgacg catccgtttg ggaaatgttc atggctttgc tgtctggcgc cagcctgtac     720
atccttttcca acagacgat ccatgatttc gctgcatttg aacactattt gagtgaaaat     780
gaattgacca tcatcacact gccgccgact tatttgactc acctcacccc agagcgcatc     840
acctcgctac gcatcatgat tacggcagga tcagcttcct ccgcacccct tggtaaacaa     900
tggaaagaca aactcaggta cataaatgca tacgcccga cggaaacgag catttgcgcg     960
acgatctggg aagccccgtc caatcagctc tccgtgcaat cggttccgat cggcaaaccg    1020
attcaaaata cacatattta tatcgtcaat gaagacttgc agctactgcc gactggcagc    1080
gaaggcgaat gtgcatcgg cggagtcggc ttggcaagag ctattggaa tcggcccgac    1140
ttgaccgcga aaaattcgt agacaatccg ttcgtaccag cgaaaaaat gtaccgcaca    1200
ggtgacttgg ccaaatggct gacggatgga acgatcgagt ttctcggcag aatcgaccat    1260
```

```
caggtgaaaa tcagaggtca tcgcatcgag cttggcgaaa tcgagtctgt tttgttggca   1320
catgaacaca tcacagaggc cgtggtcatt gccagagagg atcaacacgc gggacagtat   1380
ttgtgcgcct attatatttc gcaacaagaa gcaactcctg cgcagctcag agactacgcc   1440
gcccagaagc ttccggctta catgctgcca tcttatttcg tcaagctgga caaaatgccg   1500
cttacgccaa atgacaagat cgaccgcaaa gcgttgcccg agcctgatct tacggcaaac   1560
caaagccagg ctgcctacca tcctccgaga accgagacag aatcgattct cgtctccatc   1620
tggcaaaacg ttttgggaat tgaaaagatc gggattcgcg ataatttta ctcgctcggc    1680 ggagatgcga tccaagcgat ccaggtcgtg gctcgtctgc attcctatca attgaagcta   1740
gagacgaaag acttgctgaa ttacccgacg atcgagcagg ttgctctttt tgtcaagagc   1800
acgacgagaa aaagcgatca gggcatcatc gctggaaacg taccgcttac acccattcag   1860
aagtggtttt tcgggaaaaa ctttacgaat acaggccatt ggaaccaatc gtctgtgctc   1920
tatcgcccgg aaggctttga tcctaaagtc atccaaagtg tcatggacaa aatcatcgaa   1980
caccacgacg cgctccgcat ggtctatcag cacgaaaacg gaaatgtcgt tcagcacaac   2040
cgcggcttgg gtggacaatt atacgatttc ttctcttata atctgaccgc gcaaccagac   2100
gtccagcagg cgatcgaagc agagacgcaa cgtctgcaca gcagcatgaa tttgcaggaa   2160
ggacctctgg tgaaggttgc cttatttcag acgttacatg gcgatcattt gtttctcgca   2220
attcatcatt tggtcgtgga tggcattttcc tggcgcattt tgtttgaaga tttggcaacc   2280
ggatacgcgc aggcacttgc agggcaagcg atcagtctgc ccgaaaaaac ggattctttt   2340
caaagctggt cacaatggtt gcaagaatat gcgaacgagg cggatttgct gagcgagatt   2400
ccgtactggg agagtctcga atcgcaagca aaaaatgtgt ccctgccgaa agactatgaa   2460
gtgaccgact gcaaacaaaa gagcgtgcga acatgcgga tacggctgca cccggaagag    2520
accgagcagt tgttgaagca cgccaatcag gcctatcaaa cggaaatcaa cgatctgttg   2580
ttggcggcgc tcggcttggc ttttgcggag tggagcaagc ttgcgcaaat cgtcattcat   2640 ttggagggc acgggcgcga ggacatcatc gaacaggcaa acgtggccag aacggtcgga    2700
tggtttacgt cgcaatatcc ggtattgctc gacttgaagc aaaccgctcc cttgtccgac   2760
tatatcaagc tcaccaaaga gaatatgcgc aagattcctc gtaaagggat cggttacgac   2820
atcttgaagc atgtgacact tccagaaaat cgcggttcct tatccttccg cgtgcagccg   2880
gaagtgacgt tcaactactt gggacagttt gatgcggaca tgagaacgga actgtttacc   2940
cgctcaccct acagcggcgg caacacgtta ggcgcagatg gcaaaaacaa tctgagtcct   3000
gagtcagagg tgtacaccgc tttgaatata accggattga ttgaaggcgg agagctcgtc   3060
ctcacattct cttacagctc ggagcagtat cgggaagagt ccatccagca attgagccaa   3120
agttatcaaa agcatctgct tgccatcatc gcgcattgca ccgagaaaaa agaagtagag   3180
cgaacgccca gcgatttcag cgtcaaaggt ctccaaatgg aagaaatgga cgatatcttc   3240
gaattgcttg caaatacact gcgcggatcc agatctcatc accatcacca tcactaagct   3300
taa                                                                 3303
```

<210> SEQ ID NO 5
<211> LENGTH: 1088
<212> TYPE: PRT
<213> ORGANISM: Brevibacillus parabrevis

<400> SEQUENCE: 5

```
Met Leu Ala Asn Gln Ala Asn Leu Ile Asp Asn Lys Arg Glu Leu Glu
1               5                   10                  15

Gln His Ala Leu Val Pro Tyr Ala Gln Gly Lys Ser Ile His Gln Leu
            20                  25                  30

Phe Glu Glu Gln Ala Glu Ala Phe Pro Asp Arg Val Ala Ile Val Phe
        35                  40                  45

Glu Asn Arg Arg Leu Ser Tyr Gln Glu Leu Asn Arg Lys Ala Asn Gln
50                      55                  60

Leu Ala Arg Ala Leu Leu Glu Lys Gly Val Gln Thr Asp Ser Ile Val
65                  70                  75                  80

Gly Val Met Met Glu Lys Ser Ile Glu Asn Val Ile Ala Ile Leu Ala
                85                  90                  95

Val Leu Lys Ala Gly Ala Tyr Val Pro Ile Asp Ile Glu Tyr Pro
            100                 105                 110

Arg Asp Arg Ile Gln Tyr Ile Leu Gln Asp Ser Gln Thr Lys Ile Val
            115                 120                 125

Leu Thr Gln Lys Ser Val Ser Gln Leu Val His Asp Val Gly Tyr Ser
        130                 135                 140

Gly Glu Val Val Leu Asp Glu Gln Leu Asp Ala Arg Glu Thr
145                 150                 155                 160

Ala Asn Leu His Gln Pro Ser Lys Pro Thr Asp Leu Ala Tyr Val Ile
            165                 170                 175

Tyr Thr Ser Gly Thr Thr Gly Lys Pro Lys Gly Thr Met Leu Glu His
            180                 185                 190

Lys Gly Ile Ala Asn Leu Gln Ser Phe Phe Gln Asn Ser Phe Gly Val
        195                 200                 205

Thr Glu Gln Asp Arg Ile Gly Leu Phe Ala Ser Met Ser Phe Asp Ala
210                 215                 220

Ser Val Trp Glu Met Phe Met Ala Leu Leu Ser Gly Ala Ser Leu Tyr
225                 230                 235                 240

Ile Leu Ser Lys Gln Thr Ile His Asp Phe Ala Ala Phe Glu His Tyr
            245                 250                 255

Leu Ser Glu Asn Glu Leu Thr Ile Ile Thr Leu Pro Pro Thr Tyr Leu
        260                 265                 270

Thr His Leu Thr Pro Glu Arg Ile Thr Ser Leu Arg Ile Met Ile Thr
        275                 280                 285

Ala Gly Ser Ala Ser Ser Ala Pro Leu Val Asn Lys Trp Lys Asp Lys
        290                 295                 300

Leu Arg Tyr Ile Asn Ala Tyr Gly Pro Thr Glu Thr Ser Ile Cys Ala
305                 310                 315                 320

Thr Ile Trp Glu Ala Pro Ser Asn Gln Leu Ser Val Gln Ser Val Pro
            325                 330                 335

Ile Gly Lys Pro Ile Gln Asn Thr His Ile Tyr Ile Val Asn Glu Asp
            340                 345                 350

Leu Gln Leu Leu Pro Thr Gly Ser Glu Gly Glu Leu Cys Ile Gly Gly
        355                 360                 365

Val Gly Leu Ala Arg Gly Tyr Trp Asn Arg Pro Asp Leu Thr Ala Glu
        370                 375                 380

Lys Phe Val Asp Asn Pro Phe Val Pro Gly Glu Lys Met Tyr Arg Thr
385                 390                 395                 400

Gly Asp Leu Ala Lys Trp Leu Thr Asp Gly Thr Ile Glu Phe Leu Gly
            405                 410                 415

Arg Ile Asp His Gln Val Lys Ile Arg Gly His Arg Ile Glu Leu Gly
```

```
                420             425             430
Glu Ile Glu Ser Val Leu Leu Ala His Glu His Ile Thr Glu Ala Val
            435             440             445
Val Ile Ala Arg Glu Asp Gln His Ala Gly Gln Tyr Leu Cys Ala Tyr
        450             455             460
Tyr Ile Ser Gln Gln Glu Ala Thr Pro Ala Gln Leu Arg Asp Tyr Ala
465             470             475             480
Ala Gln Lys Leu Pro Ala Tyr Met Leu Pro Ser Tyr Phe Val Lys Leu
            485             490             495
Asp Lys Met Pro Leu Thr Pro Asn Asp Lys Ile Asp Arg Lys Ala Leu
        500             505             510
Pro Glu Pro Asp Leu Thr Ala Asn Gln Ser Gln Ala Ala Tyr His Pro
    515             520             525
Pro Arg Thr Glu Thr Glu Ser Ile Leu Val Ser Ile Trp Gln Asn Val
    530             535             540
Leu Gly Ile Glu Lys Ile Gly Ile Arg Asp Asn Phe Tyr Ser Leu Gly
545             550             555             560
Gly Asp Ser Ile Gln Ala Ile Gln Val Val Ala Arg Leu His Ser Tyr
            565             570             575
Gln Leu Lys Leu Glu Thr Lys Asp Leu Leu Asn Tyr Pro Thr Ile Glu
        580             585             590
Gln Val Ala Leu Phe Val Lys Ser Thr Thr Arg Lys Ser Asp Gln Gly
    595             600             605
Ile Ile Ala Gly Asn Val Pro Leu Thr Pro Ile Gln Lys Trp Phe Phe
    610             615             620
Gly Lys Asn Phe Thr Asn Thr Gly His Trp Asn Gln Ser Ser Val Leu
625             630             635             640
Tyr Arg Pro Glu Gly Phe Asp Pro Lys Val Ile Gln Ser Val Met Asp
            645             650             655
Lys Ile Ile Glu His His Asp Ala Leu Arg Met Val Tyr Gln His Glu
        660             665             670
Asn Gly Asn Val Val Gln His Asn Arg Gly Leu Gly Gly Gln Leu Tyr
    675             680             685
Asp Phe Phe Ser Tyr Asn Leu Thr Ala Gln Pro Asp Val Gln Gln Ala
    690             695             700
Ile Glu Ala Glu Thr Gln Arg Leu His Ser Ser Met Asn Leu Gln Glu
705             710             715             720
Gly Pro Leu Val Lys Val Ala Leu Phe Gln Thr Leu His Gly Asp His
            725             730             735
Leu Phe Leu Ala Ile His His Leu Val Val Asp Gly Ile Ser Trp Arg
        740             745             750
Ile Leu Phe Glu Asp Leu Ala Thr Gly Tyr Ala Gln Ala Leu Ala Gly
    755             760             765
Gln Ala Ile Ser Leu Pro Glu Lys Thr Asp Ser Phe Gln Ser Trp Ser
    770             775             780
Gln Trp Leu Gln Glu Tyr Ala Asn Glu Ala Asp Leu Leu Ser Glu Ile
785             790             795             800
Pro Tyr Trp Glu Ser Leu Glu Ser Gln Ala Lys Asn Val Ser Leu Pro
            805             810             815
Lys Asp Tyr Glu Val Thr Asp Cys Lys Gln Lys Ser Val Arg Asn Met
        820             825             830
Arg Ile Arg Leu His Pro Glu Glu Thr Glu Gln Leu Leu Lys His Ala
    835             840             845
```

-continued

Asn Gln Ala Tyr Gln Thr Glu Ile Asn Asp Leu Leu Leu Ala Ala Leu
        850                 855                 860

Gly Leu Ala Phe Ala Glu Trp Ser Lys Leu Ala Gln Ile Val Ile His
865                 870                 875                 880

Leu Glu Gly His Gly Arg Glu Asp Ile Ile Glu Gln Ala Asn Val Ala
                885                 890                 895

Arg Thr Val Gly Trp Phe Thr Ser Gln Tyr Pro Val Leu Leu Asp Leu
        900                 905                 910

Lys Gln Thr Ala Pro Leu Ser Asp Tyr Ile Lys Leu Thr Lys Glu Asn
        915                 920                 925

Met Arg Lys Ile Pro Arg Lys Gly Ile Gly Tyr Asp Ile Leu Lys His
        930                 935                 940

Val Thr Leu Pro Glu Asn Arg Gly Ser Leu Ser Phe Arg Val Gln Pro
945                 950                 955                 960

Glu Val Thr Phe Asn Tyr Leu Gly Gln Phe Asp Ala Asp Met Arg Thr
                965                 970                 975

Glu Leu Phe Thr Arg Ser Pro Tyr Ser Gly Asn Thr Leu Gly Ala
        980                 985                 990

Asp Gly Lys Asn Asn Leu Ser Pro Glu Ser Glu Val Tyr Thr Ala Leu
        995                 1000                1005

Asn Ile Thr Gly Leu Ile Glu Gly Gly Glu Leu Val Leu Thr Phe Ser
        1010                1015                1020

Tyr Ser Ser Glu Gln Tyr Arg Glu Glu Ser Ile Gln Gln Leu Ser Gln
1025                1030                1035                1040

Ser Tyr Gln Lys His Leu Leu Ala Ile Ile Ala His Cys Thr Glu Lys
                1045                1050                1055

Lys Glu Val Glu Arg Thr Pro Ser Asp Phe Ser Val Lys Gly Leu Gln
                1060                1065                1070

Met Glu Glu Met Asp Asp Ile Phe Glu Leu Leu Ala Asn Thr Leu Arg
                1075                1080                1085

<210> SEQ ID NO 6
<211> LENGTH: 1087
<212> TYPE: PRT
<213> ORGANISM: Brevibacillus parabrevis

<400> SEQUENCE: 6

Met Leu Ala Asn Gln Ala Asn Leu Ile Asp Asn Lys Arg Glu Leu Glu
1               5                   10                  15

Gln His Ala Leu Val Pro Tyr Ala Gln Gly Lys Ser Ile His Gln Leu
            20                  25                  30

Phe Glu Glu Gln Ala Glu Ala Phe Pro Asp Arg Val Ala Ile Val Phe
        35                  40                  45

Glu Asn Arg Arg Leu Ser Tyr Gln Glu Leu Asn Arg Lys Ala Asn Gln
    50                  55                  60

Leu Ala Arg Ala Leu Leu Glu Lys Gly Val Gln Thr Asp Ser Ile Val
65                  70                  75                  80

Gly Val Met Met Glu Lys Ser Ile Glu Asn Val Ile Ala Ile Leu Ala
                85                  90                  95

Val Leu Lys Ala Gly Gly Ala Tyr Val Pro Ile Asp Ile Glu Tyr Pro
            100                 105                 110

Arg Asp Arg Ile Gln Tyr Ile Leu Gln Asp Ser Gln Thr Lys Ile Val
        115                 120                 125

Leu Thr Gln Lys Ser Val Ser Gln Leu Val His Asp Val Gly Tyr Ser

```
                130             135             140
Gly Glu Val Val Leu Asp Glu Glu Gln Leu Asp Ala Arg Glu Thr
145                 150                 155                 160

Ala Asn Leu His Gln Pro Ser Lys Pro Thr Asp Leu Ala Tyr Val Ile
                165                 170                 175

Tyr Thr Ser Gly Thr Thr Gly Lys Pro Lys Gly Thr Met Leu Glu His
            180                 185                 190

Lys Gly Ile Ala Ile Cys Asn Pro Phe Ser Lys Ile Arg Leu Ala Ser
                195                 200                 205

Pro Ser Lys Thr Gly Ser Gly Phe Leu Pro Ala Cys Arg Ser Thr His
        210                 215                 220

Pro Phe Gly Lys Cys Ser Trp Leu Cys Cys Leu Ala Pro Arg Val His
225                 230                 235                 240

Pro Ser Lys Gln Thr Ile His Asp Phe Ala Ala Phe Glu His Tyr Leu
                245                 250                 255

Ser Glu Asn Glu Leu Thr Ile Ile Thr Leu Pro Pro Thr Tyr Leu Thr
            260                 265                 270

His Leu Thr Pro Glu Arg Ile Thr Ser Leu Arg Ile Met Ile Thr Ala
        275                 280                 285

Gly Ser Ala Ser Ala Pro Leu Val Asn Lys Trp Lys Asp Lys Leu
290                 295                 300

Arg Tyr Ile Asn Ala Tyr Gly Pro Thr Glu Thr Ser Ile Cys Ala Thr
305                 310                 315                 320

Ile Trp Glu Ala Pro Ser Asn Gln Leu Ser Val Gln Ser Val Pro Ile
                325                 330                 335

Gly Lys Pro Ile Gln Asn Thr His Ile Tyr Ile Val Asn Glu Asp Leu
            340                 345                 350

Gln Leu Leu Pro Thr Ala Asp Glu Gly Glu Leu Cys Ile Gly Gly Val
        355                 360                 365

Gly Leu Ala Arg Gly Tyr Trp Asn Arg Pro Asp Leu Thr Ala Glu Lys
        370                 375                 380

Phe Val Asp Asn Pro Phe Val Pro Gly Glu Lys Met Tyr Arg Thr Gly
385                 390                 395                 400

Asp Leu Ala Lys Trp Leu Thr Asp Gly Thr Ile Glu Phe Leu Gly Arg
                405                 410                 415

Ile Asp His Gln Val Lys Ile Arg Gly His Arg Ile Glu Leu Gly Glu
            420                 425                 430

Ile Glu Ser Val Leu Leu Ala His Glu His Ile Thr Glu Ala Val Val
        435                 440                 445

Ile Ala Arg Glu Asp Gln His Ala Gly Gln Tyr Leu Cys Ala Tyr Tyr
450                 455                 460

Ile Ser Gln Gln Glu Ala Thr Pro Ala Gln Leu Arg Asp Tyr Ala Ala
465                 470                 475                 480

Gln Lys Leu Pro Ala Tyr Met Leu Pro Ser Tyr Phe Val Lys Leu Asp
                485                 490                 495

Lys Met Pro Leu Thr Pro Asn Asp Lys Ile Asp Arg Lys Ala Leu Pro
            500                 505                 510

Glu Pro Asp Leu Thr Ala Asn Gln Ser Gln Ala Ala Tyr His Pro Pro
        515                 520                 525

Arg Thr Glu Thr Glu Ser Ile Leu Val Ser Ile Trp Gln Asn Val Leu
        530                 535                 540

Gly Ile Glu Lys Ile Gly Ile Arg Asp Asn Phe Tyr Ser Leu Gly Gly
545                 550                 555                 560
```

```
Asp Ser Ile Gln Ala Ile Gln Val Val Ala Arg Leu His Ser Tyr Gln
            565                 570                 575

Leu Lys Leu Glu Thr Lys Asp Leu Leu Asn Tyr Pro Thr Ile Glu Gln
            580                 585                 590

Val Ala Leu Phe Val Lys Ser Thr Thr Arg Lys Ser Asp Gln Gly Ile
            595                 600                 605

Ile Ala Gly Asn Val Pro Leu Thr Pro Ile Gln Lys Trp Phe Phe Gly
            610                 615                 620

Lys Asn Phe Thr Asn Thr Gly His Trp Asn Gln Ser Ser Val Leu Tyr
625                 630                 635                 640

Arg Pro Glu Gly Phe Asp Pro Lys Val Ile Gln Ser Val Met Asp Lys
                    645                 650                 655

Ile Ile Glu His His Asp Ala Val Arg Met Val Tyr Gln His Glu Asn
                    660                 665                 670

Gly Asn Val Val Gln His Asn Arg Gly Leu Gly Gly Gln Leu Tyr Asp
                    675                 680                 685

Phe Phe Ser Tyr Asn Leu Thr Ala Gln Pro Asp Val Gln Gln Ala Ile
            690                 695                 700

Glu Ala Glu Thr Gln Arg Leu His Ser Ser Met Asn Leu Gln Glu Gly
705                 710                 715                 720

Pro Leu Val Lys Val Ala Leu Phe Gln Thr Leu His Gly Asp His Phe
                    725                 730                 735

Phe Leu Ala Ile His His Leu Val Val Asp Gly Ile Ser Trp Arg Ile
                    740                 745                 750

Leu Phe Lys Ile Trp Gln Pro Asp Thr Arg Arg His Leu Gln Gly Lys
            755                 760                 765

Arg Ser Val Cys Pro Lys Lys Arg Ile Leu Phe Lys Ala Gly His Asn
770                 775                 780

Gly Cys Lys Asn Asn Ala Asn Glu Ala Asp Leu Leu Ser Glu Ile Pro
785                 790                 795                 800

Tyr Trp Glu Ser Leu Glu Ser Gln Ala Lys Asn Val Ser Leu Pro Lys
                    805                 810                 815

Asp Tyr Glu Val Thr Asp Cys Lys Gln Lys Ser Val Arg Asn Met Arg
                    820                 825                 830

Ile Arg Leu His Pro Glu Glu Thr Glu Gln Leu Leu Lys His Ala Asn
            835                 840                 845

Gln Ala Tyr Gln Thr Glu Ile Asn Asp Leu Leu Leu Ala Ala Leu Gly
            850                 855                 860

Leu Ala Phe Ala Glu Trp Ser Lys Leu Ala Lys Ser Ser Phe Ile Trp
865                 870                 875                 880

Arg Gly Thr Gly Ala Arg Thr Ser Ser Asn Arg Gln Thr Val Ala Arg
                    885                 890                 895

Thr Val Gly Trp Phe Thr Ser Gln Tyr Pro Val Leu Leu Asp Leu Lys
                    900                 905                 910

Gln Thr Ala Pro Leu Ser Asp Tyr Ile Lys Leu Thr Lys Glu Asn Met
            915                 920                 925

Arg Lys Ile Pro Arg Lys Gly Ile Gly Tyr Asp Ile Leu Lys His Val
            930                 935                 940

Thr Leu Pro Glu Asn Arg Gly Ser Leu Ser Phe Arg Val Gln Pro Glu
945                 950                 955                 960

Val Thr Phe Asn Tyr Leu Gly Gln Phe Asp Ala Asp Met Arg Thr Glu
                    965                 970                 975
```

| | | | | | | | | | | | | |
|---|---|---|---|---|---|---|---|---|---|---|---|---|
|Leu|Phe|Thr|Arg|Ser|Pro|Tyr|Ser|Gly|Gly|Asn|Thr|Leu|Gly|Ala|Asp|
| | | |980| | | |985| | | |990| |

Gly Lys Asn Asn Leu Ser Pro Glu Ser Glu Val Tyr Thr Ala Leu Asn
        995              1000             1005

Ile Thr Gly Leu Ile Glu Gly Gly Glu Leu Val Leu Thr Phe Ser Tyr
    1010             1015             1020

Ser Ser Glu Gln Tyr Arg Glu Ser Ile Gln Gln Leu Ser Gln Ser
1025             1030             1035             1040

Tyr Gln Lys His Leu Leu Ala Ile Ile Ala His Cys Thr Glu Lys Lys
            1045             1050             1055

Glu Val Glu Arg Thr Pro Ser Asp Phe Ser Val Lys Gly Leu Gln Met
        1060             1065             1070

Glu Glu Met Asp Asp Ile Phe Glu Leu Leu Ala Asn Thr Leu Arg
        1075             1080             1085

<210> SEQ ID NO 7
<211> LENGTH: 4316
<212> TYPE: DNA
<213> ORGANISM: Brevibacillus brevis

<400> SEQUENCE: 7

```
ctggtggatc gcaaagtaca tgccaaactg ctggtggatt ttccttgaac caaatttcgc      60
tggcagccag catggttcaa acctttctc taaaaagctg cgtcacgtca aaaagaggg       120
ggtaggaatt gtgcctttt atcacatgcc tttttacgaa agtctgcgga ctgatcagga     180
caatagctgc tgatccagat aggcagcaca caggaaaaca gcctctcgtt tttccgtaga     240
agaaaattcc tgttttccca gtataaagca ttatatggct tgtgaacata taaaaatttt     300
aatgttatga aaatatttat cgtcaaaata tagccgtacg ctttccttt ttatagacaa      360
gttgaaaagg aaaaatgttg cagcgccgaa acgagccaat cactggcttc accaagggga     420
aaaacacgtg tgccgcttat tgattacgca agcgggagca ggtttgccaa gcaaaacttg     480
gatttacgta aaaggttgt aaaaaaactt gttgaatttt ttgcaaaata tccctatttt      540
ttaatcgact tccaattttt ctctgctata atgagtttca gcgtcagtaa cctagtgctt     600
tcagcctgtc agccgatcgg ggaacttcct gtgattgttt tcatgcaaat cagttttcct    660
tcgttcgcag cgtaagcagg cgtatccggc agcggaatac cagcacccat tttccgctac    720
agcatgagca aaatatgact ttagtatgaa gggaatttcc cagaaacagg aaatttttctt   780
gttgttaaaa ttacccaaat gatggaaaat gggaaattgg aatggaacgt tgaccttgcc    840
tgtctcttgt tggcaaccat ttcgtcacac ttcatgataa gcagaagtaa ttccattatc    900
ggagggaca tatgttagca aatcaggcca atctcatcga caacaagcgg aactggagc      960
agcatgcgct agttccatat gcacagggca agtcgatcc tcaattgttc gaggaacaag    1020
cagaggcttt tccagaccgc gttgccatcg tttttgaaaa caggcggctt tcgtatcagg    1080
agttgaacag gaaagccaat caactggcaa gagccttgct cgaaaaaggg gtgcaaacag   1140
acagcatcgt cggtgtgatg atggagaagt ccatcgaaaa tgtcatcgcg attctggccg   1200
ttcttaaagc aggcggagcc tatgtgccca tcgacatcga atatcccgc gatcgcatcc    1260
aatatatttt gcaggatagt caaacgaaaa tcgtgcttac ccaaaaaagc gtcagccagc    1320
tcgtgcatga cgtcgggtac agcggagagg tagttgtact cgacgaagaa cagttggacg   1380
ctcgcgagac tgccaatctg caccagccca gcaagcctac ggatcttgcc tatgtcattt    1440
acacctcagg cacgacaggc aagccaaaag gcaccatgct tgaacataaa ggcatcgcaa   1500
```

```
tttgcaatcc ttttttccaaa attcgtttgg cgtcaccgag caagacagga tcgggctttt    1560
tgccagcatg tcgttcgacg catccgtttg ggaaatgttc atggctttgc tgtctggcgc    1620
cacgtgtaca tccttccaaa cagacgatcc atgatttcgc tgcatttgaa cactatttga    1680
gtgaaaatga attgaccatc atcacactgc cgccgactta tttgactcac ctcaccccag    1740
agcgcatcac ctcgctacgc atcatgatta cggcaggatc agcttcctcc gcacccttgg    1800
taaacaaatg gaaagacaaa ctcaggtaca taaatgcata cggcccgacg gaaacgagca    1860
tttgcgcgac gatctgggaa gccccgtcca atcagctctc cgtgcaatcg gttccgatcg    1920
gcaaaccgat tcaaaataca catatttata tcgtcaatga agacttgcag ctactgccga    1980
ctgcggacga aggcgaattg tgcatcggcg gagtcggctt ggcaagaggc tattggaatc    2040
ggcccgactt gaccgcagaa aaattcgtag acaatccgtt cgtaccaggc gaaaaaatgt    2100
accgcacagg tgacttggcc aaatggctga cggatggaac gatcgagttt ctcggcagaa    2160
tcgaccatca ggtgaaaatc agaggtcatc gcatcgagct tggcgaaatc gagtctgttt    2220
tgttggcaca tgaacacatc acagaggccg tggtcattgc cagagaggat caacacgcgg    2280
gacagtattt gtgcgcctat tatatttcgc aacaagaagc aactcctgcg cagctcagag    2340
actacgccgc ccagaagctt ccggcttaca tgctgccatc ttatttcgtc aagctggaca    2400
aaatgccgct tacgccaaat gacaagatcg accgcaaagc gttgcccgag cctgatctta    2460
cggcaaacca aagccaggct gcctaccatc ctccgagaac cgagacagaa tcgattctcg    2520
tctccatctg gcaaaacgtt tgggaattg aaaagatcgg gattcgcgat aattttttact    2580 cgctcggcgg agattcgatc caagcgatcc aggtcgtggc tcgtctgcat tcctatcaat    2640
tgaagctaga gacgaaagac ttgctgaatt acccgacgat cgagcaggtt gctctttttg    2700
tcaagagcac gacgagaaaa agcgatcagg gcatcatcgc tggaaacgta ccgcttacac    2760
ccattcagaa gtggttttc gggaaaaact ttacgaatac aggccattgg aaccaatcgt    2820
ctgtgctcta tcgcccggaa ggctttgatc ctaaagtcat ccaaagtgtc atggacaaaa    2880
tcatcgaaca ccacgacgcc gtccgcatgg tctatcagca cgaaaacgga aatgtcgttc    2940
agcacaaccg cggcttgggt ggacaattat acgatttctt ctcttataat ctgaccgcgc    3000
aaccagacgt ccagcaggcg atcgaagcag agacgcaacg tctgcacagc agcatgaatt    3060
tgcaggaagg acctctggtg aaggttgcct tatttcagac gttacatggc gatcatttct    3120
ttctcgcaat tcatcatttg gtcgtggatg gcatttcctg gcgcattttg tttaagattt    3180
ggcaaccgga tacgcgcagg cacttgcagg gcaagcgatc agtctgcccg aaaaaacgga    3240
ttcttttcaa agctggtcac aatggttgca agaataatgc gaacgaggcg gatttgctga    3300
gcgagattcc gtactgggag agtctcgaat cgcaagcaaa aaatgtgtcc ctgccgaaag    3360
actatgaagt gaccgactgc aaacaaaaga gcgtgcgaaa catgcggata cggctgcacc    3420
cggaagagac cgagcagttg ttgaagcacg ccaatcaggc ctatcaaacg gaaatcaacg    3480
atctgttgtt ggcggcgctc ggcttggctt ttgcggagtg gagcaagctt gcgaaatcgt    3540
cattcatttg gaggggcacg ggcgcgagga catcatcgaa caggcaaacg gtggccagaa    3600
cggtcggatg gttacgtcg caatatccgg tattgctcga cttgaagcaa accgctccct    3660
```

```
tgtccgacta tatcaagctc accaaagaga atatgcggaa gattcctcgt aaagggatcg    3720
gttacgacat cttgaagcat gtgacacttc cagaaaatcg cggttcctta tccttccgcg    3780
tgcagccgga agtgacgttc aactacttgg gacagtttga tgcggacatg agaacggaac   3840
tgtttacccg ctcaccctac agcggcggca acacgttagg cgcagatggc aaaaacaatc    3900
tgagtcctga gtcagaggtg tacaccgctt tgaatataac cggattgatt gaaggcggag    3960
agctcgtcct cacattctct tacagctcgg agcagtatcg ggaagagtcc atccagcaat    4020
tgagccaaag ttatcaaaag catctgcttg ccatcatcgc gcattgcacc gagaaaaaag    4080
aagtagagcg aacgcccagc gatttcagcg tcaaaggtct ccaaatggaa gaaatggacg    4140
atatcttcga attgcttgca aatacactgc gctaaacaga tgttggccac cattttcagg    4200
ggcaactgcg tgctttcatt cccattttta tacatttata acaaataaag atatatccga    4260
ggtgccgtaa tgagtgtatt tagcaaagaa caagttcagg atatgtatgc gttgac        4316

<210> SEQ ID NO 8
<211> LENGTH: 41
<212> TYPE: DNA
<213> ORGANISM: Artificial Sequence
<220> FEATURE:
<223> OTHER INFORMATION: A synthetic primer

<400> SEQUENCE: 8
ttactcgctc ggcggagatg cgatccaagc gatccaggtc g                         41

<210> SEQ ID NO 9
<211> LENGTH: 41
<212> TYPE: DNA
<213> ORGANISM: Artificial Sequence
<220> FEATURE:
<223> OTHER INFORMATION: A synthetic primer

<400> SEQUENCE: 9
cgacctggat cgcttggatc gcatctccgc cgagcgagta a                         41
```

BIOSYNTHESIS OF PACLITAXEL INTERMEDIATE

CROSS REFERENCE TO RELATED APPLICATIONS

This application is a Continuation of U.S. patent application Ser. No. 14/408,515, filed Apr. 20, 2015, issued as U.S. Pat. No. 9,732,365, and which is a U.S. National Stage Application under 35 U.S.C. § 371 of PCT/US2012/042951, filed on Jun. 18, 2012, and published on Dec. 27, 2013 as WO2013/191678, the contents of which are specifically incorporated herein by reference in their entirety.

GOVERNMENT FUNDING

This invention was made with government support under MCB0746432 by the National Science Foundation. The government has certain rights in the invention.

BACKGROUND OF THE INVENTION

Drug shortages in the United States have become an increasing problem. Taxol®, otherwise known by the generic name paclitaxel, is a chemotherapeutic agent used to treat breast cancer, as well as ovarian, lung and colon cancers. Shortages of paclitaxel can limit or curtail treatment options for cancer patients. New, more efficient procedures for making paclitaxel may avoid such drug shortages and ensure a reliable pharmaceutical supply chain.

Paclitaxel has been produced by semisynthetic and plant cell fermentation (PCF) techniques. The semisynthetic method of making paclitaxel (shown below) requires over seventeen synthetic steps and involves use of voluminous organic solvents during the production process.

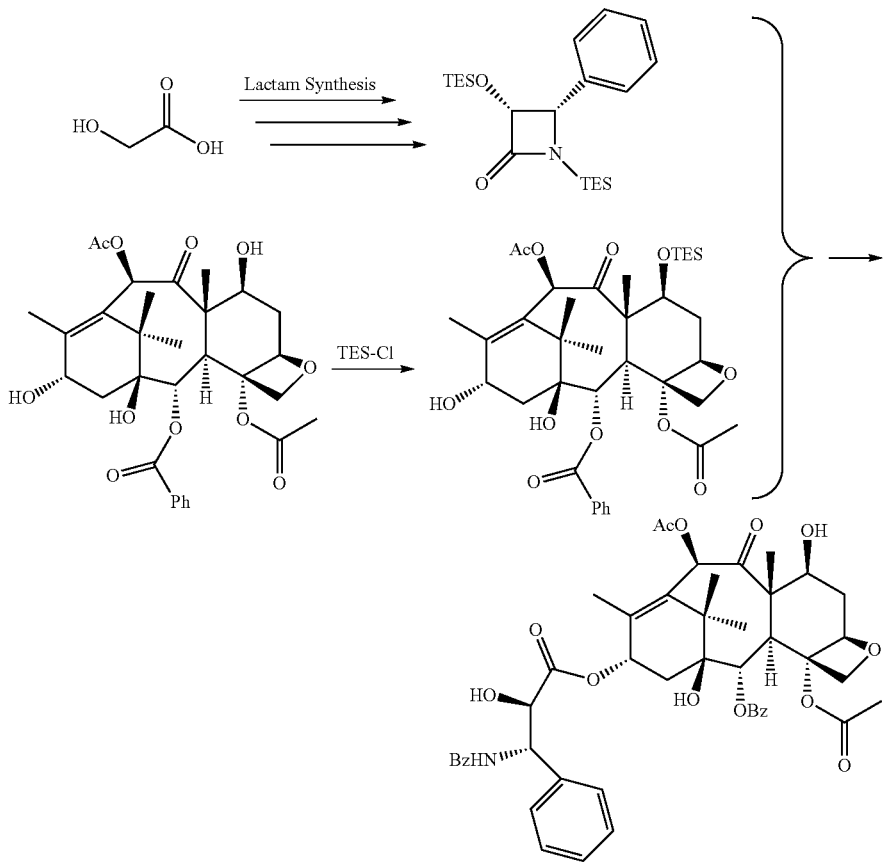

While the simplicity of coupling the necessary phenylisoserine side chain to the diterpene core of the paclitaxel molecule made such semisynthetic methods attractive, the multiple steps and the environmental hazards of the solvents and side products involved make the semisynthetic approach less attractive than the plant cell fermentation methods.

However, while the plant cell fermentation procedures do tend to use less toxic materials, the amount of paclitaxel obtained can be low. For example, in cell cultures, the concentration of paclitaxel ranges from 0.04 to 0.2%, depending on cell lines. Large fermentation vats must be used and the isolation and separation of paclitaxel from the milieu of plant cell lysates must be very efficient to obtain useful amounts of paclitaxel.

SUMMARY

The invention relates to more efficient and non-toxic methods for making paclitaxel where not only the production but also the purification of the paclitaxel product is simplified. In particular, the enzymes and methods described herein can generate aminopropanyl-CoA intermediates, such as (R)-β-phenylalanyl-CoA and (2R,3S)-phenylisoserinyl CoA, that are useful substrates in an enzymatic pathway for the production of paclitaxel and related anti-cancer drugs.

The methods of making paclitaxel, or analogs or derivatives thereof, include preparing an aminopropanoyl-CoA in a reaction catalyzed by a Tyrocidine synthetase A (TycA) to thereby make an intermediate for production of paclitaxel or an analog or derivative thereof. The Tyrocidine synthetase A can have a bacterial amino acid sequence. For example, the Tyrocidine synthetase A can have a *Bacillus brevis* or *Brevibacillus parabrevis* Tyrocidine synthetase A. In some embodiments, the Tyrocidine synthetase A can have an amino acid sequence of a Tyrocidine synthetase A from bacteria deposited with the American Type Culture Collection under deposit number ATCC 8185. In other embodiments, a serine in the Tyrocidine synthetase A can be replaced with a substitute amino acid that does not have a hydroxy in its side chain. For example, the substitute amino acid in the Tyrocidine synthetase A can be an alanine, valine, isovaline, leucine, isoleucine, proline, glycine, arginine, lysine, histidine, tryptophan, phenylalanine, methionine or cysteine. In some embodiments, the Tyrocidine synthetase A has an amino acid sequence comprising a sequence selected from the group consisting of SEQ ID NO:1, SEQ ID NO:3, SEQ ID NO:5, SEQ ID NO:6, and an amino acid sequence with 85% sequence identity to any of SEQ ID NO:1, SEQ ID NO:3, SEQ ID NO:5, or SEQ ID NO:6. The Tyrocidine synthetase A can, for example, be encoded by a nucleic acid sequence comprising a sequence selected from the group consisting of SEQ ID NO:2, SEQ ID NO:4, SEQ ID NO:7, and an nucleic acid sequence with 85% sequence identity to any of SEQ ID NO:2, SEQ ID NO:4 or SEQ ID NO:7.

The reaction can be performed in vitro. For example, the reaction can be performed in a cell-free reaction such as an enzymatic reaction that can proceed in a mixture of the Tyrocidine synthetase A, the substrate, ATP and a divalent cation. The Tyrocidine synthetase A can be immobilized or attached to a solid surface (e.g., a bead, a column matrix, a reaction wall and the like). Alternatively, a substrate for the Tyrocidine synthetase A can be immobilized or attached to a solid surface (e.g., a bead, a column matrix, a reaction wall and the like). Such attachment can facilitate isolation of the products of the reaction and removal of unreacted materials, side products, and other materials that are no longer needed. In some embodiments, the reaction can be performed in a cultured cell. In other embodiments, the reaction can be performed in a cultured cell during a plant cell fermentation process.

A variety of substrates can be employed. For example, the aminopropanoyl-CoA can be prepared from a substrate of the following formula I:

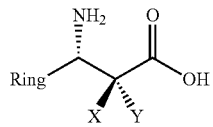

wherein:
X is hydrogen;
Y is hydrogen or OH; and
Ring is an unsubstituted or substituted (C4-C10) aryl, (C4-C9)heteroaryl, (C4-C10)cycloalkyl, or (C4-C9) heterocycloalkyl.

Such a substrate can be immobilized or attached to a solid surface (e.g., a bead, a column matrix, a reaction wall and the like). The aminopropanoyl-CoA prepared by the methods described herein can be a compound of formula II:

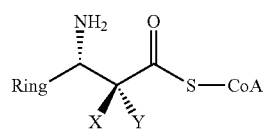

wherein: X, Y and Ring are as described herein. Such an aminopropanoyl-CoA is a useful intermediate for making paclitaxel or paclitaxel analog or derivative. For example, such paclitaxel, paclitaxel analogs or paclitaxel derivatives can have the following structure:

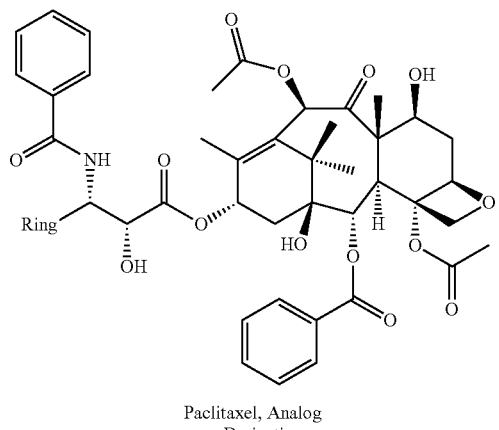

Paclitaxel, Analog or Derivative wherein: Ring is an unsubstituted or substituted (C4-C10) aryl, (C4-C9)heteroaryl, (C4-C10)cycloalkyl, or (C4-C9) heterocycloalkyl. In some embodiments, Ring is a single aryl or heteroaryl ring of about 4-8 carbon atoms, and where the heteroatom is oxygen or nitrogen. The Ring can have a variety of substituents. For example, the Ring can be substituted with 1 or 2 alkyl, amino, hydroxy, cyano, carboxy, nitro, thio, alkoxy, and halogen groups.

In some embodiments, the aminopropanoyl-CoA can be prepared from a substrate with formula III or IV:

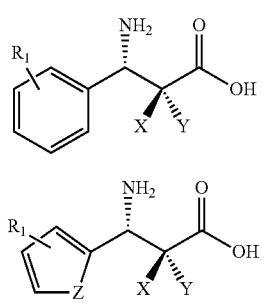

wherein: X is hydrogen; Y is hydrogen or OH; Z is CH, CH$_2$, oxygen (O) or nitrogen (NH or NH$_2$); and R$_1$ is selected from the group consisting of hydrogen, alkyl, amino, hydroxy, cyano, carboxy, nitro, thio, alkoxy, and halogen.

In other embodiments, the aminopropanoyl-CoA can have formula V or VI:

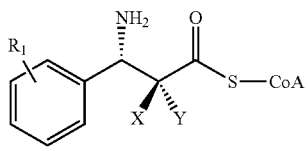

V

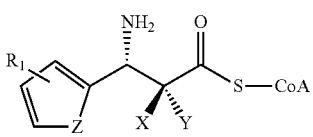

VI wherein:

X is hydrogen;

Y is hydrogen or OH;

Z is CH, $CH_2$, oxygen (O), or nitrogen (NH or $NH_2$); and $R_1$ is selected from the group consisting of hydrogen, alkyl, amino, hydroxy, cyano, carboxy, nitro, thio, alkoxy, and halogen.

The aminopropanoyl-CoA substrates and/or intermediates can be immobilized or attached to a solid surface (e.g., a bead, a column matrix, a reaction wall and the like). Such immobilization or attachment can facilitate reaction to generate paclitaxel (or an analog or derivative thereof), as well as purification of intermediates and final products along the synthetic route.

The method can further include reaction B involving combining the aminopropanoyl-CoA with Baccatin III:

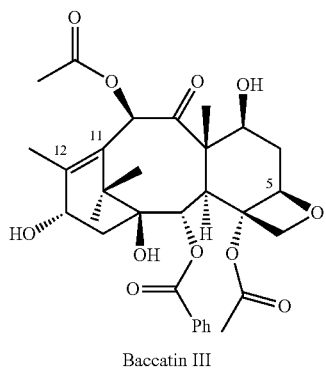

Baccatin III to form N-debenzoyl-2'-deoxypaclitaxel or an analog or derivative thereof. For example, reaction B can be catalyzed by an acyltransferase such as a *Taxus* acyltransferase. In some embodiments, reaction B can be catalyzed by baccatin III O-phenylpropanoyltransferase (BAPT). When performing reaction B, the reaction can, for example, proceed in a mixture of aminopropanyl-CoA, baccatin III O-phenylpropanoyltransferase (BAPT), and Baccatin III. The aminopropanoyl-CoA, baccatin III O-phenylpropanoyltransferase (BAPT), or Baccatin III. can be immobilized or attached to a solid surface (e.g., a bead, a column matrix, a reaction wall and the like). Such immobilization or attachment can facilitate reaction to generate paclitaxel (or an analog or derivative thereof), as well as purification of intermediates and final products along the synthetic route. The N-debenzoyl-2'-deoxypaclitaxel or an analog or derivative thereof can have the following structure:

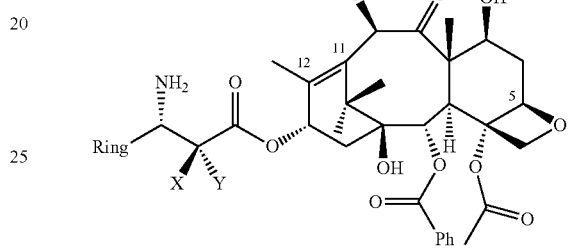

3'-N-Debenzoyltaxol or an analog or derivative thereof wherein:

X is hydrogen;

Y is hydrogen or OH; and

Ring is an unsubstituted or substituted (C4-C10) aryl, (C4-C9)heteroaryl, (C4-C10)cycloalkyl, or (C4-C9) heterocycloalkyl.

Reaction B can also be performed in vitro, for example, in a cell-free reaction such as an enzymatic reaction. In other embodiments, Reaction B can be performed in a cultured cell, or in a plant cell fermentation process, for example, in combination with the reaction for preparing an aminopropanoyl-CoA that can be catalyzed by Tyrocidine synthetase A.

The methods provided herein can further include a reaction A that includes transfer of benzoyl group to a free amine of a propanoid side chain of 3'-N-debenzoyl-paclitaxel or an analog or derivative thereof to form paclitaxel or an analog or derivative thereof. The 3'-N-debenzoyl-paclitaxel (or an analog or derivative thereof) or the paclitaxel (or analog or derivative thereof) can be immobilized or attached to a solid surface (e.g., a bead, a column matrix, a reaction wall and the like). Such immobilization or attachment can facilitate reaction to generate paclitaxel (or an analog or derivative thereof), as well as purification of the paclitaxel (or analog or derivative thereof) product. For example, when the paclitaxel or an analog or derivative thereof is attached or immobilized on a solid surface, the solid surface can be washed to remove reactants, enzymes, side products and the like. Upon cleavage from the solid surface, a purified paclitaxel or an analog or derivative thereof can be obtained.

The paclitaxel or an analog or derivative thereof can have the following structure:

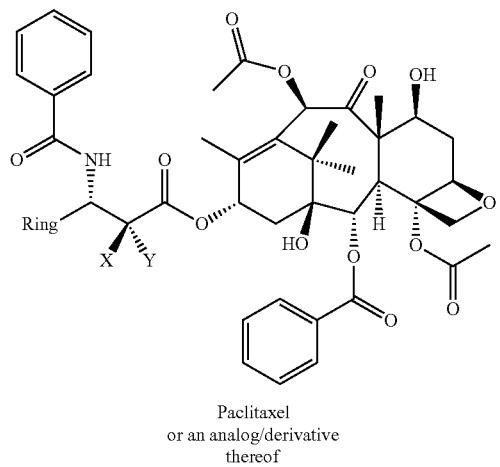

Paclitaxel
or an analog/derivative
thereof wherein: Ring is an unsubstituted or substituted (C4-C10) aryl, (C4-C9)heteroaryl, (C4-C10)cycloalkyl, or (C4-C9) heterocycloalkyl. In some embodiments, the Ring can be a single aryl or heteroaryl ring of about 4-8 carbon atoms, and where the heteroatom is oxygen or nitrogen. For example, the Ring can be substituted with 1 or 2 alkyl, amino, hydroxy, cyano, carboxy, nitro, thio, alkoxy, and halogen groups.

Reaction A can be catalyzed by an acyltransferase, for example, a *Taxus* acyltransferase. In some embodiments, reaction A can be catalyzed by N-debenzoyl-2'-deoxypaclitaxel: N-benzoyltransferase (NDTBT). For example, reaction A can proceed in a mixture of 3'-N-debenzoyl-paclitaxel, a benzoyl-contributing agent and N-debenzoyl-2'-deoxypaclitaxel: N-benzoyltransferase (NDTBT). Such a reaction A can be performed in vitro, for example, reaction A can be performed in a cell-free reaction. In other embodiments, reaction A can be performed in a cultured cell, or in a plant cell fermentation process, for example, in combination with the reaction for preparing an aminopropanoyl-CoA that can be catalyzed by Tyrocidine synthetase A.

The methods provided herein can also include other reaction steps for generating paclitaxel, paclitaxel analogs and paclitaxel derivatives, including those described herein or otherwise available.

DESCRIPTION OF THE FIGURES

FIGS. 2A-F illustrates the MS(/MS) ionization profiles of products isolated after separately incubating TycA or TycA-S563A with (S)-α-phenylalanine, (R)-β-phenylalanine, or (2R,3S)-phenylisoserine under standard assay conditions with CoA. FIG. 2A shows an MS(/MS) ionization profile of pure (S)-α-phenylalanine demonstrating that an [M−H]⁻ consistent with phenylalanyl-CoA (m/z 913) is present in the total ion profile (FIG. 2A1); and the types of fragment ions derived by MS/MS of the corresponding m/z 913 ion (FIG. 2A2). FIG. 2B shows an MS(/MS) ionization profile of pure (R)-β-phenylalanine demonstrating that an [M−H]⁻ consistent with β-phenylalanyl-CoA (m/z 913) in is present in the total ion profile (FIG. 2B-1); and the types of fragment ions derived by MS/MS of the corresponding m/z 913 ion (FIG. 2B-2). FIG. 2C shows an MS(/MS) ionization profile of pure (2R,3S)-phenylisoserine demonstrating that an [M−H]⁻ consistent with phenylisoserinyl-CoA (m/z 929) is present in the total ion profile (FIG. 2C-1); and the types of fragment ions derived by MS/MS of the corresponding m/z 929 ion (FIG. 2C-2). The [M−H]⁻ ion selected for MS/MS analysis from each sample are identified in bold with an asterisk.

FIG. 3A-C shows representative a liquid chromatography multiple reaction monitoring (LC-ESI-MRM) profiles of purified aminophenylpropanoyl-CoA compounds (FIG. 3A1, 3B 1, 3C1), LC-ESI-MS total ion profiles (FIG. 3A2, 3B2, 3C2), and fragment ions (FIG. 3A3, 3B3, 3C3) derived by MS/MS of the corresponding [M−H]⁻ molecular ion of biosynthetic α-phenylalanyl-CoA (FIG. 3A), β-phenylalanyl-CoA (FIG. 3B), and phenylisoserinyl-CoA (FIG. 3C) made in reactions containing TycA or TycA-S563A (100 µg), ATP (1 mM), MgCl₂ (3 mM), CoA (1 mM), and the corresponding aminophenylpropanoate (1 mM).

(FIG. 5A). Control assays contained the same ingredients but without (2S,3R)-phenylisoserine (FIG. 5B) or without ATP (FIG. 5C), or without CoA (FIG. 5D).

FIG. 7A-C illustrates total ion profile of LC-ESI-MS analyses (FIG. 7A1, 7B1, 7C1) and fragment ions derived by MS/MS of the corresponding [M+H]⁺ molecular ion (FIG. 7A2, 7B2, 7C2) of authentic[S—((S)-α-phenylalanyl)-N-(acetyl)]cysteamine (FIG. 7A), [S—((R)-β-phenylalanyl)-N-(acetyl)]cysteamine (FIG. 7B), and [S-(2R,3S)-phenylisoserinyl-N-(acetyl)]cysteamine (FIG. 7C). The [M+H]⁺ ion selected for MS/MS analysis from each sample are designated with asterisk and bold.

Figure 1:
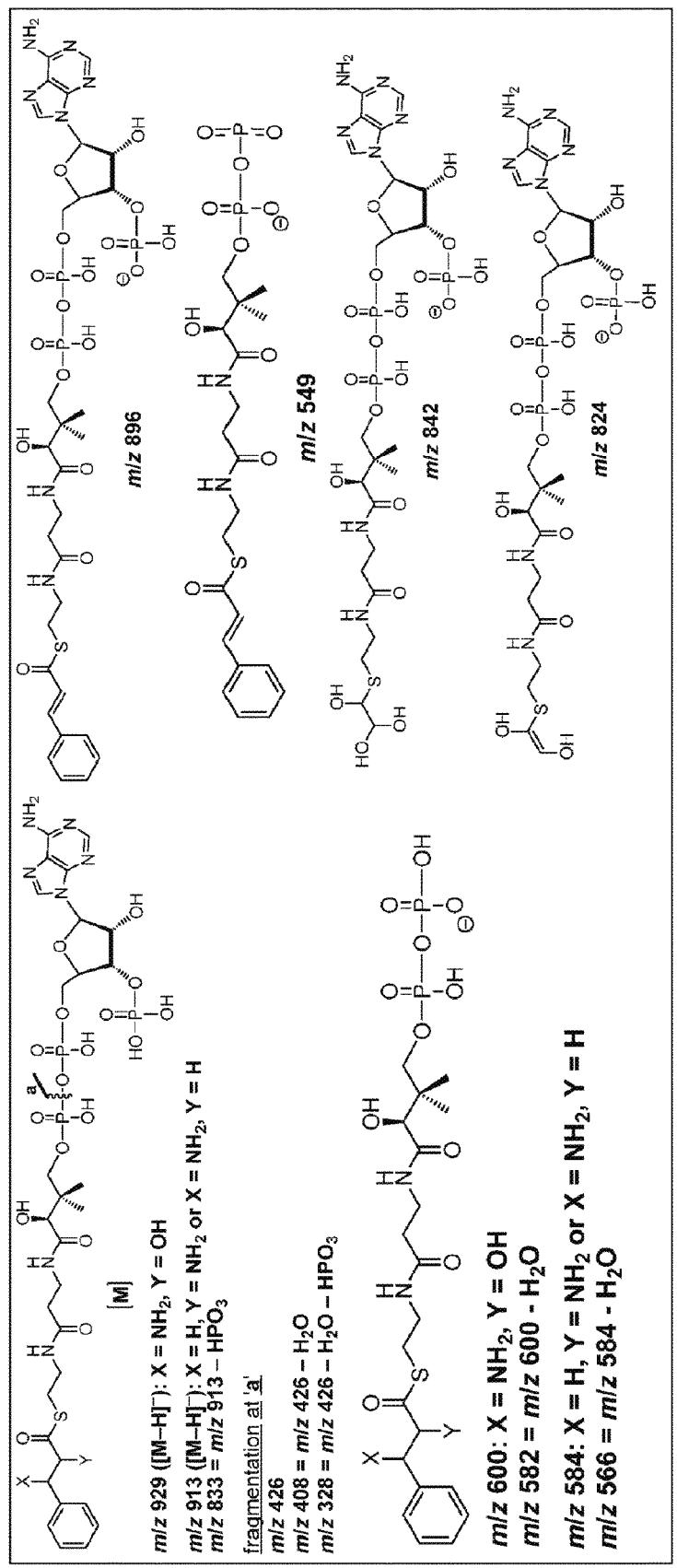
FIG. 1 shows compounds formed during the TycA thioesterification of aminophenylpropanoates and mass to charge (m/z) values for those compounds and fragments thereof.
Figure 4A:
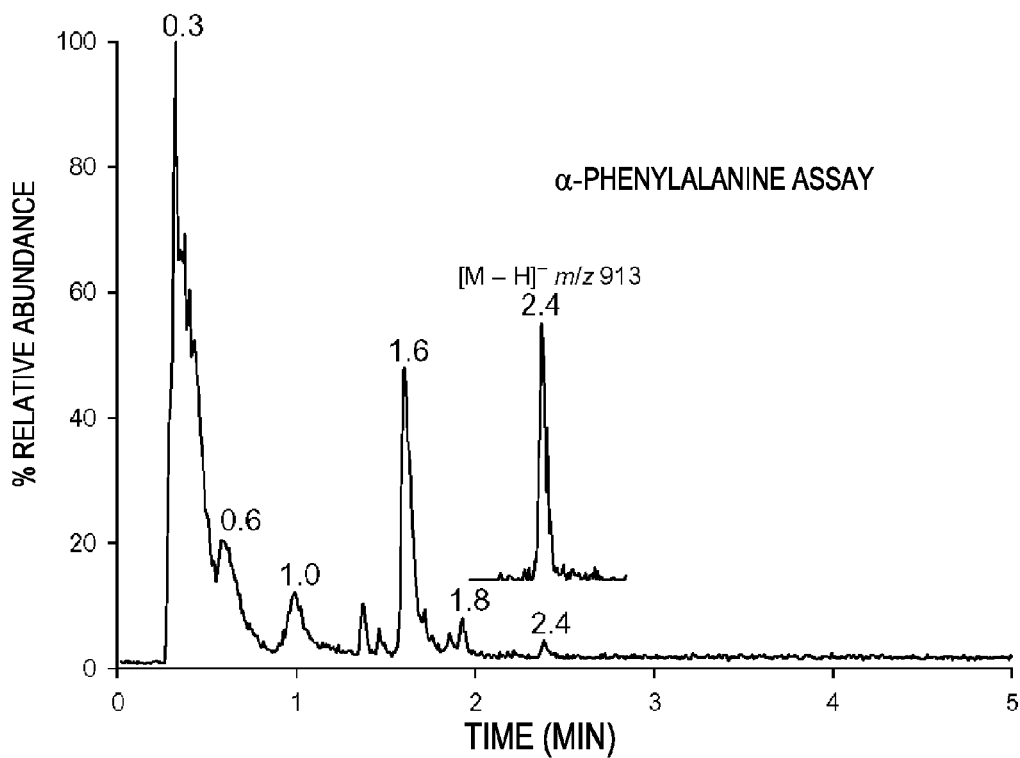
FIG. 4A-F shows a total ion chromatograms obtained by LC-ESI-MS analysis (scan mode: m/z 100 to 1200) of the compounds in assays incubated for 30 min at 31° C. containing TycA (100 µg), ATP (1 mM, 100 nmol in 0.1 mL), CoA (1 mM), and Mg²⁺ (3 mM) as well as 1 mM α-phenylalanine (FIG. 4A), or 1 mM β-phenylalanine (FIG. 4B). Control assays contained the same ingredients for α-phenylalanine without ATP (FIG. 4C) or for β-phenylalanine without ATP (FIG. 4D). Other control assays contained the same ingredients for α-phenylalanine without CoA (FIG. 4E) or for β-phenylalanine without CoA (FIG. 4F).
Figure 4B:
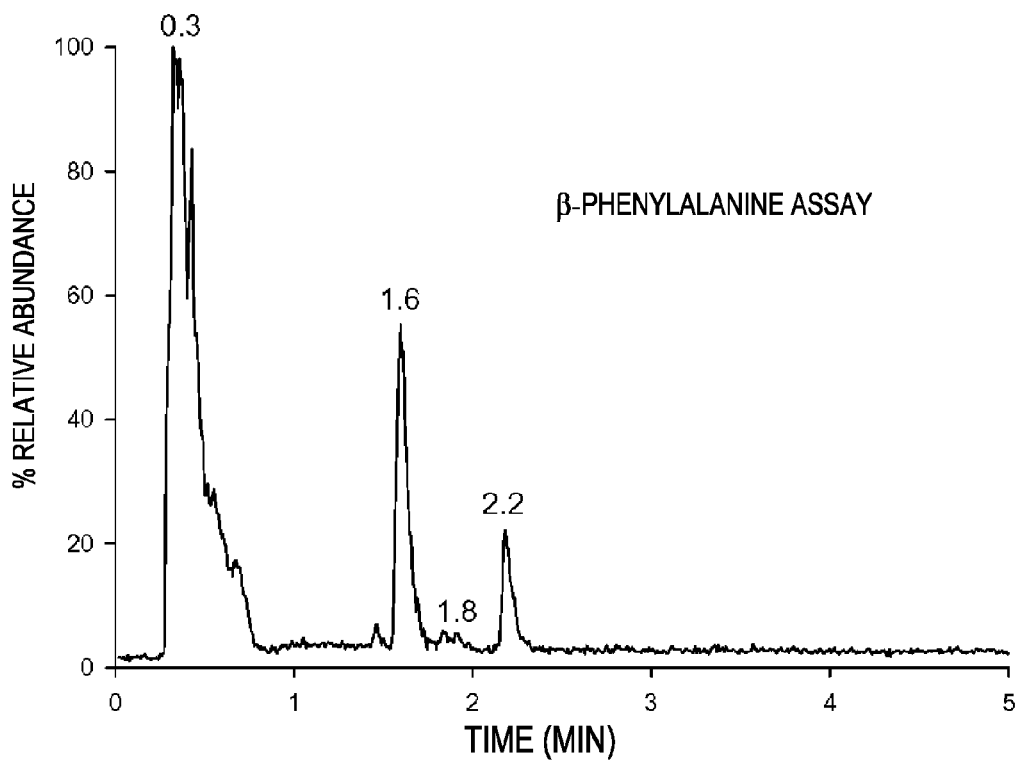
Figure 4C:
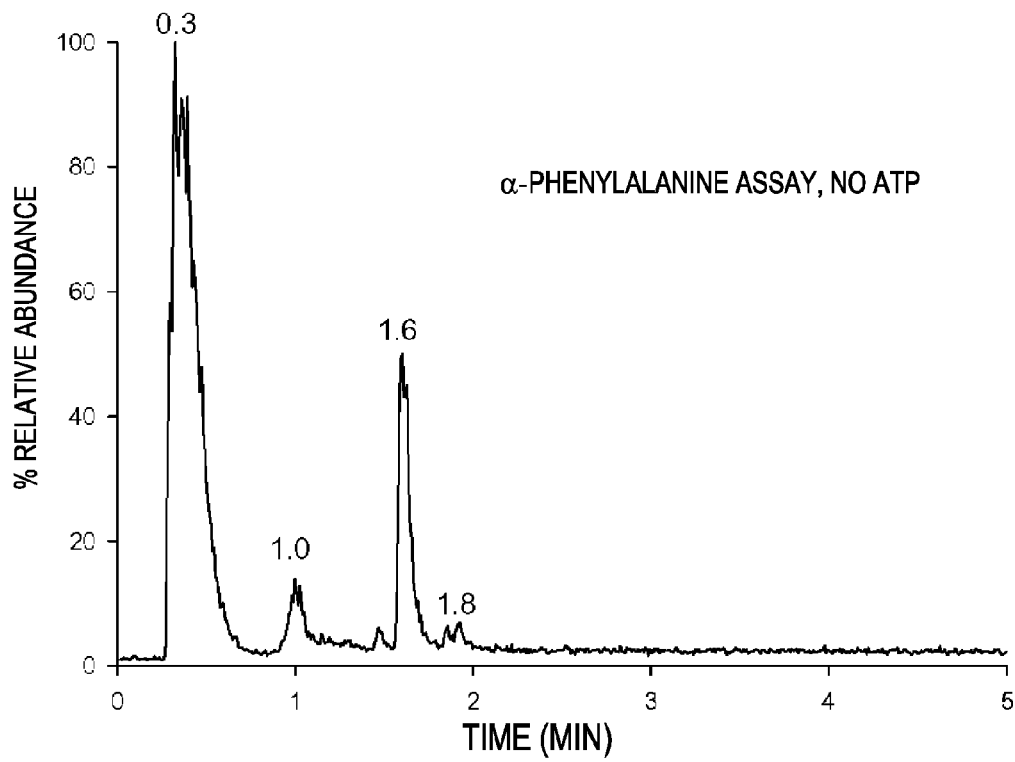
Figure 4D:
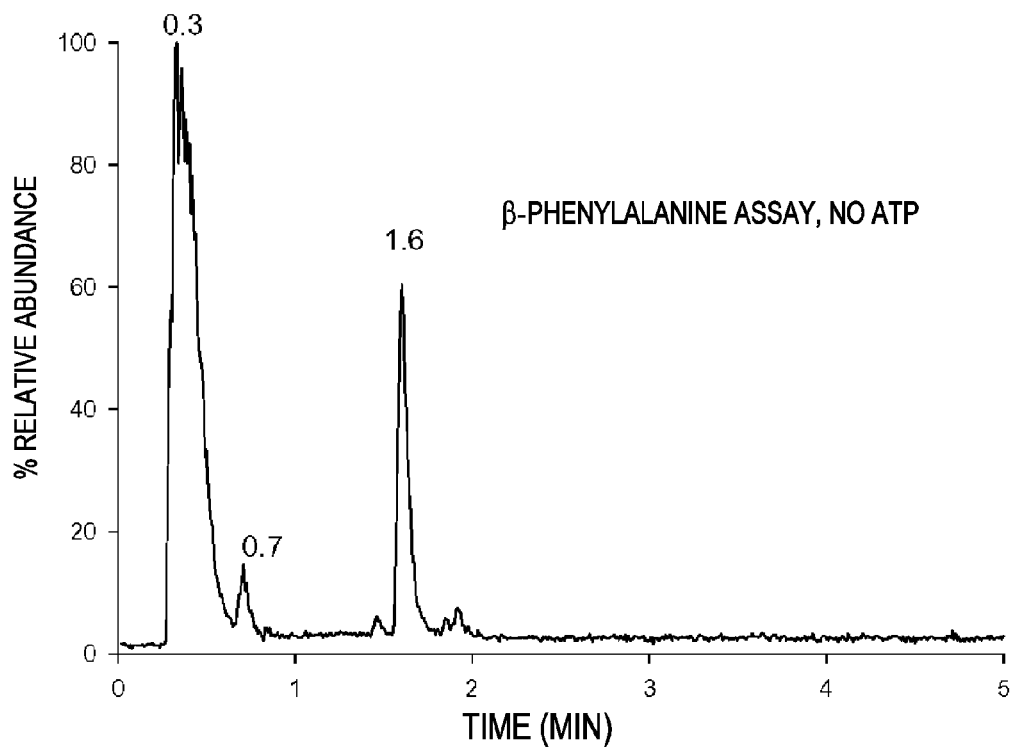
Figure 4E:
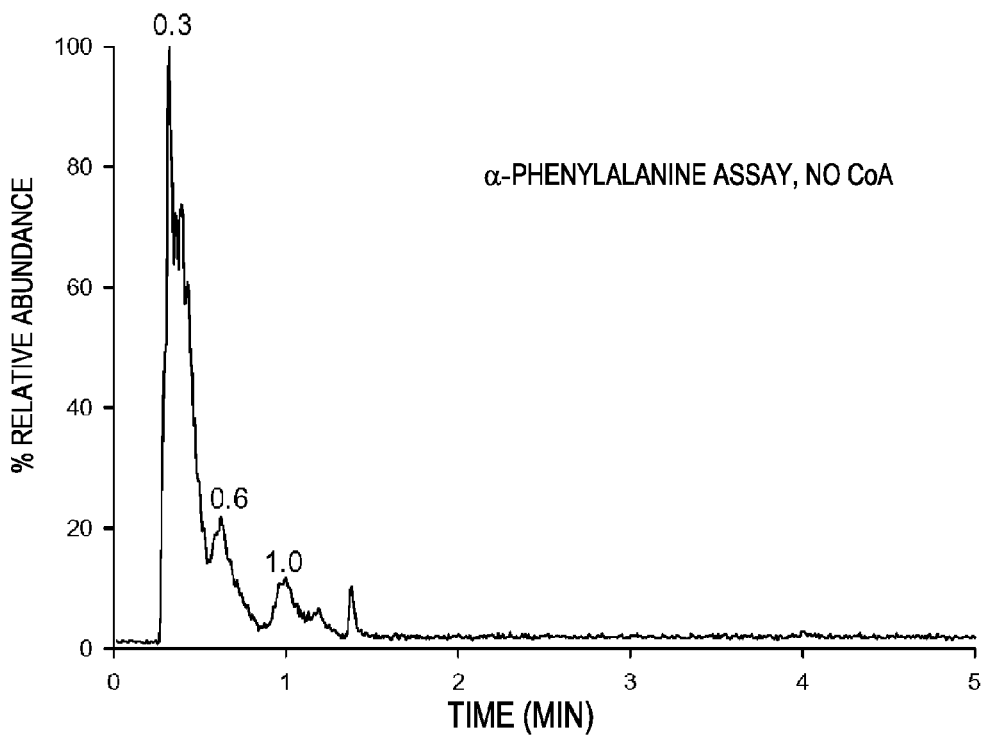
Figure 4F:
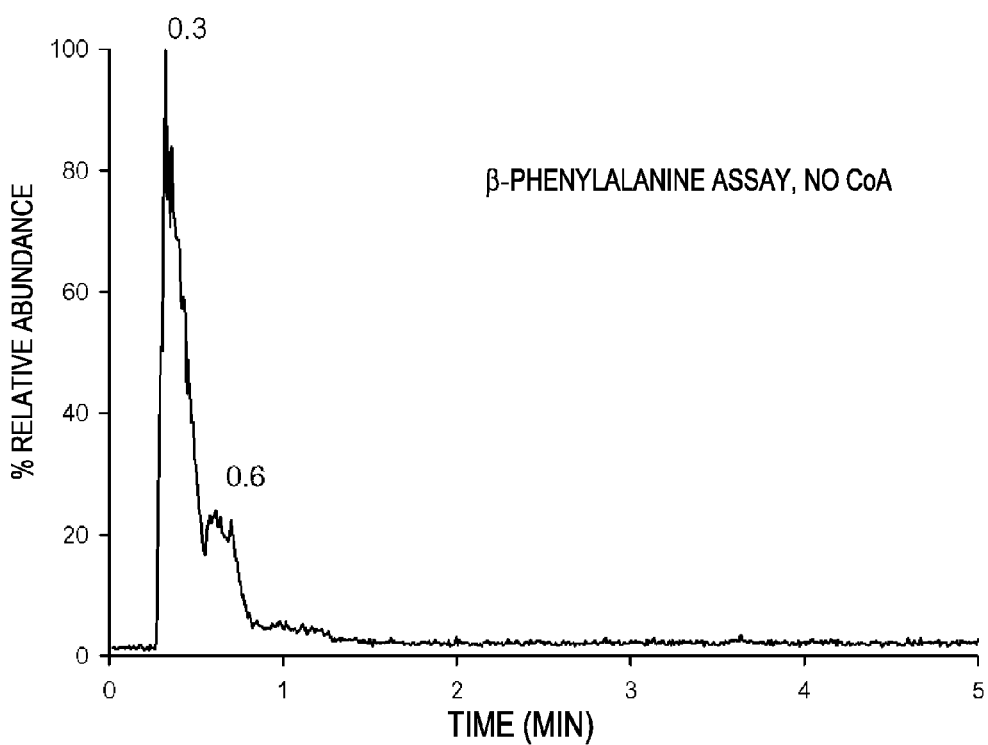
Figure 5A:
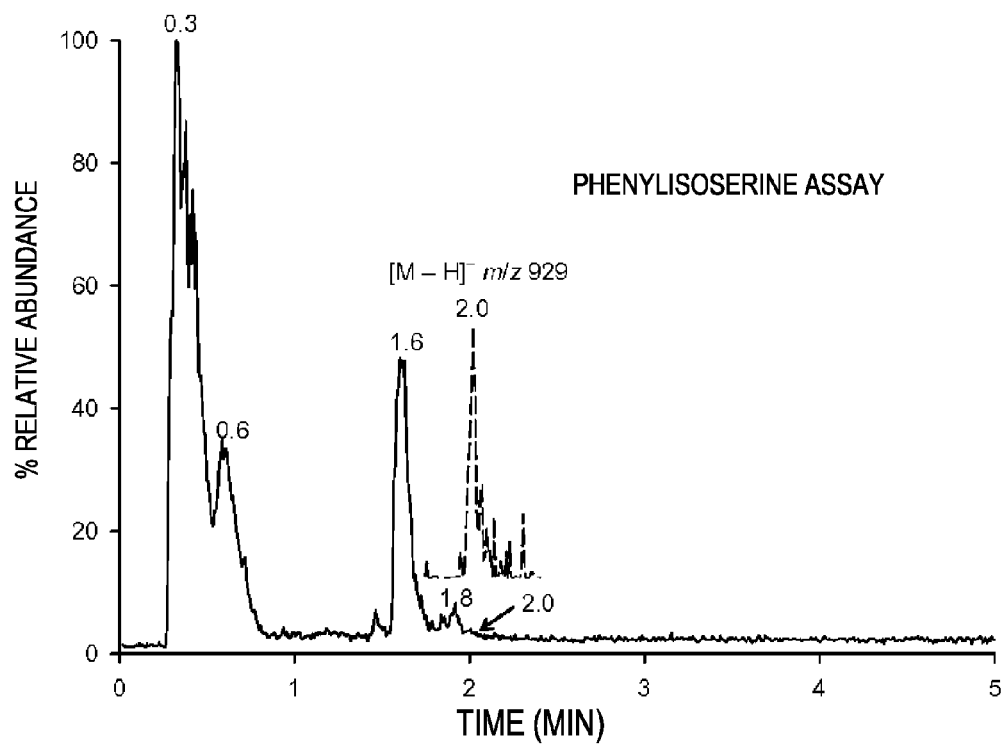
FIG. 5A-D shows total ion chromatograms obtained by LC-ESI-MS analysis (scan mode: m/z 100 to 1200) of the compounds in a (2S,3R)-phenylisoserinyl CoA assay. The assay containing TycA (100 µg), ATP (1 mM, 100 nmol in 0.1 mL), CoA (1 mM), Mg²⁺ (3 mM) as well as 1 mM (2S,3R)-phenylisoserine that was incubated for 30 min at 31° C.
Figure 5B:
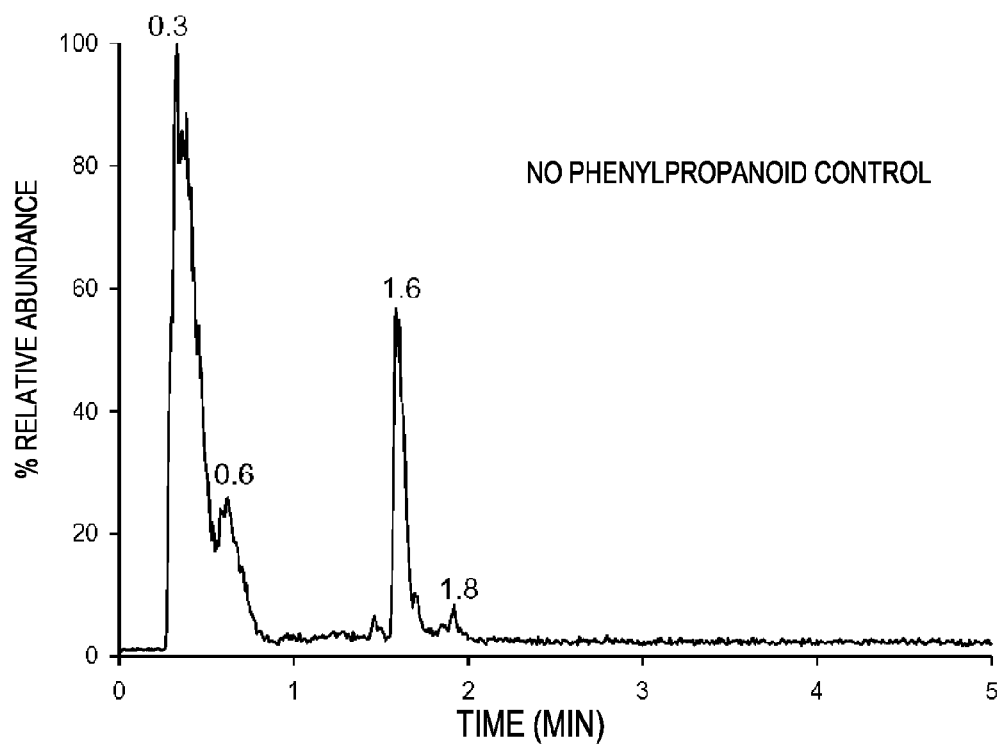
Figure 5C:
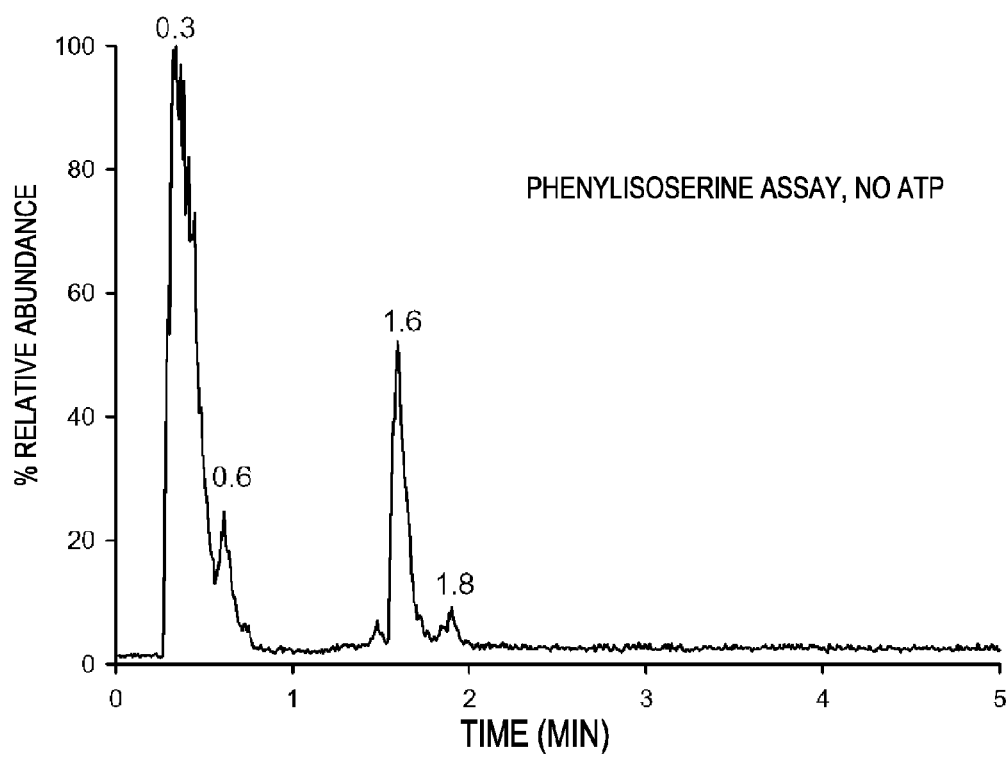
Figure 5D:
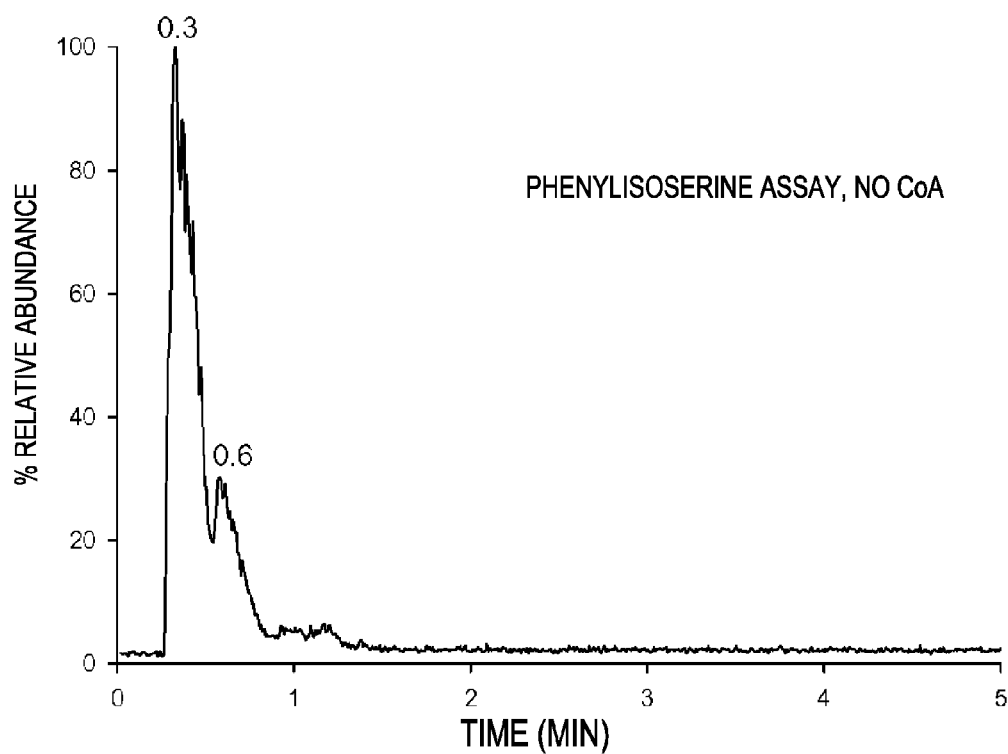

In the following detailed description of example embodiments of the invention, reference is made to the accompanying drawings which form a part hereof, and which is shown by way of illustration only, specific embodiments in which the invention may be practiced. It is to be understood that other embodiments may be utilized and structural changes may be made without departing from the scope of the present invention.

DETAILED DESCRIPTION

Currently, *Taxus* plant cell fermentation (PCF) is used for mass-producing the anti-cancer drug paclitaxel (Taxol®) as well as some related drugs. The structure of paclitaxel is shown below.

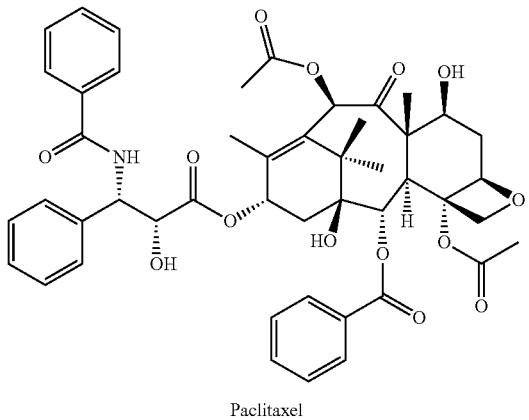

Paclitaxel

Plant cell fermentation has replaced a semisynthetic method that employed 1) a synthetic phenylisoserine (Phelso) precursor (as a β-lactam) that was coupled to the C13-hydroxyl group of baccatin III, 2) compulsory protecting group steps, and 3) voluminous hazardous solvents and toxic reagents for the large-scale production of paclitaxel (Mountford, The Taxol® Story—Development of a Green Synthesis via Plant Cell Fermentation. In Green Chemistry in the Pharmaceutical Industry, P. J. Dunn, A. S. Wells, and M. T. Williams, eds. (Wiley-VCH Verlag GmbH & Co. KGaA), pp. 145-160 (2010)).

Although plant cell fermentation procedures avoid the use of some of the hazardous solvents and toxic reagents used in the semisynthetic methods, the paclitaxel product must still be extracted and purified from the plant cells. Such extraction and purification can still require several steps to separate the paclitaxel from plant molecules with similar chemical and physical properties. Although the organic solvents employed (e.g., isobutyl acetate, isopropanol, dichloromethane, dimethylformamide and others) are generally less toxic than those employed for the semi-synthetic process of making paclitaxel, a cell-free enzymatic process of making paclitaxel would eliminate many impurities and make isolation of paclitaxel even simpler. Larger quantities of paclitaxel could also be produced without the need to grow up large vats of plant cells.

As described herein, important compounds useful in the synthesis of paclitaxel and its analogs can readily be produced by use of a tyrocidine synthetase enzyme.

Synthesis of Paclitaxel and its Analogs and Derivatives

As described herein, Tyrocidine synthetases, such as tyrocidine A, can catalyze the synthesis of aminopropanoyl-CoA compounds via the following reaction:

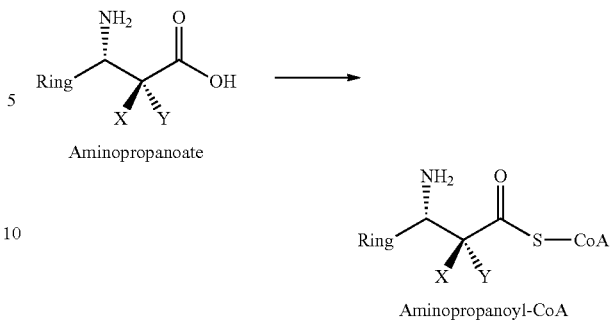

wherein:

X is hydrogen;

Y is hydrogen or OH; and

Ring is an unsubstituted or substituted (C4-C10) aryl, (C4-C9)heteroaryl, (C4-C10)cycloalkyl, or (C4-C9)heterocycloalkyl.

The aminopropanoyl-CoA compound is useful for making paclitaxel as well as paclitaxel analogs and derivatives. For example, the aminopropanoyl-CoA compound can be used to make a paclitaxel compound or a paclitaxel analog or derivative with the following structure:

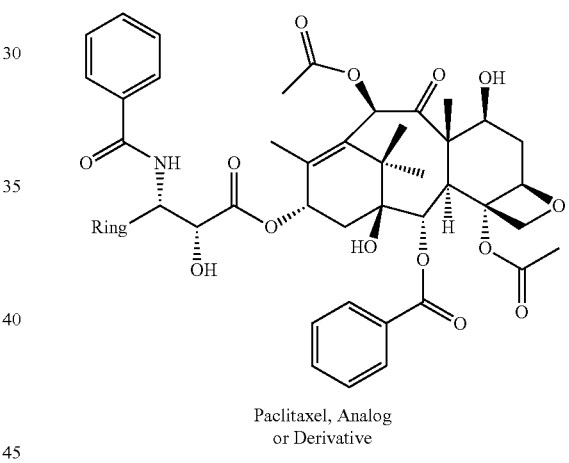

Paclitaxel, Analog or Derivative

The Ring on the aminopropanoyl-CoA compound or on the paclitaxel, or analog or derivative thereof, can be an unsubstituted or substituted (C4-C10)cycloalkyl, (C4-C9) heterocycloalkyl, (C4-C10)cycloaryl, (C4-C9)heterocycloaryl. The Ring can be a single aryl, heteroaryl, cycloalkyl, or heterocycloalkyl ring; or a fused ring system with 1-3 aryl, heteroaryl, cycloalkyl, or heterocycloalkyl rings, where fusion can be visualized as replacement of a bond to a hydrogen atom on one ring with a bond to a carbon atom in another ring. Examples of a suitable Ring group include a 5-6 membered aryl, or a 5-6 membered heteroaryl ring, where the heteroatom can be oxygen, nitrogen or sulfur.

The Ring group can be substituted with 1 or 2 alkyl, amino, hydroxy, cyano, carboxy, nitro, thio, alkoxy, and halogen groups. The alkyl group(s) can be lower alkyl group(s) (e.g., C1-C6 alkyl groups).

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 4, 5, 6, or 7. Cycloalkyl groups can include cycloalkyl rings having at least one double bond between 2 carbons (i.e., cycloalkenyl rings). Thus for example, the Ring can also be a cycloalkenyl group such as a cyclohexenyl, cyclopentenyl, or cyclohexadienyl group. Cycloalkenyl groups can have from 4 to about 8-12 ring members.

Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups. The term "cycloalkenyl" alone or in combination denotes a cyclic alkenyl group.

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Heterocyclyl groups include aromatic and non-aromatic ring compounds containing 3 or more ring members, of which, one or more is a heteroatom such as, but not limited to, N, O, and S. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

In general, the Ring group is preferably a single aryl or heteroaryl ring of about 4-8 carbon atoms, where the heteroatom is oxygen or nitrogen.

The paclitaxel derivatives can be formed by substitution with groups such as succinyl, glutaryl, glutamide and other groups. For example, the paclitaxel analogs and derivatives can include water-soluble paclitaxel derivatives such as those selected from the group consisting of a 2'-succinyl-paclitaxel; 2'-succinyl-paclitaxel triethanolamine; 2'glutaryl-paclitaxel; 2'-glutaryl-paclitaxel triethanolamine salt; 2'-O-ester paclitaxel with N-(dimethylaminoethyl) glutamide; and 2'-O-ester of paclitaxel with N-(dimethylaminoethyl) glutamide hydrochloride salt.

Tyrocidine Synthetase A (TycA)

As described herein, Tyrocidine synthetases can catalyze the formation of aminopropanoyl-CoA compounds useful for synthesizing paclitaxel and its analogs and derivatives. Tyrocidine synthetases are bacterial enzymes that join L-amino acids and D-amino acids together to make cyclic decapeptides. Such decapeptides often have antibiotic activity. For example, the peptide tyrocidine A is made by three *Bacillus brevis* tyrocidine synthetases and has the following sequence:

DPhe-Pro-DPhe-Asn-Gln-Tyr-Val-Orn-Leu.

Tyrocidine peptides with different amino acid sequences are not produced by different enzymes, but instead by the tyrocidine synthetase system that is capable of incorporating different amino acids at different positions. The amino acid sequence of the tyrocidine peptide is determined by the organization of enzymatic modules within a complex of synthetases and not by any RNA template.

Three tyrocidine synthetases TycA, TycB, and TycC are involved in the synthesis of tyrocidine peptides, and each tyrocidine synthetase includes modules and domains of activity. All of the ten modules of TycA, TycB, and TycC tyrocidine synthetic activity are encoded in the tyrocidine operon. Each module contains defined domains that catalyze adenylation, thioesterification and peptide bond formation. While TycA has a single module involved in activation of D-phenylalanine for insertion in a tyrocidine peptide, TycB has three modules and TycC has six modules.

TycA has three domains, the adenylation (A), peptidyl carrier protein (PCP), and epimerization (E) domains. In some embodiments, the TycA may not have the condensation domain that is present in other tyrocidine synthetases. In its natural environment, the adenylation domain employs ATP to activate a specific amino acid, which for TycA is (S)-α-phenylalanine. Such activation uses one molecule of ATP for each activated amino acid and yields an aminoacyl adenylate enzyme complex with diphosphate (also called pyrophosphate) as a side product. The adenylation proceeds as follows where i is TycA, ATP, and $Mg^{2+}$.

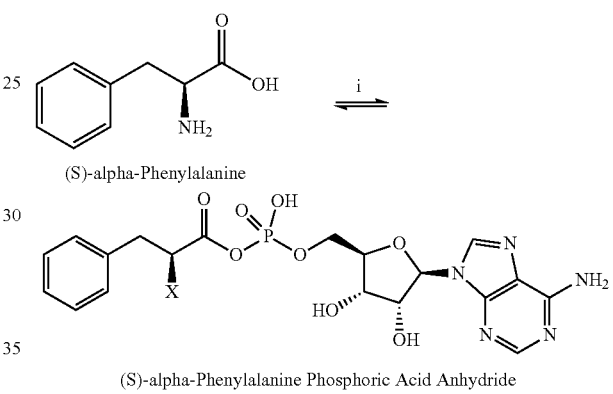

In its natural environment, TycA activates (S)-α-Phenylalanine to an adenylate anhydride and then transfers the amino acyl moiety to a pendent pantetheine of the adjacent thiolation domain (T-domain), which is part of the peptidyl carrier protein.

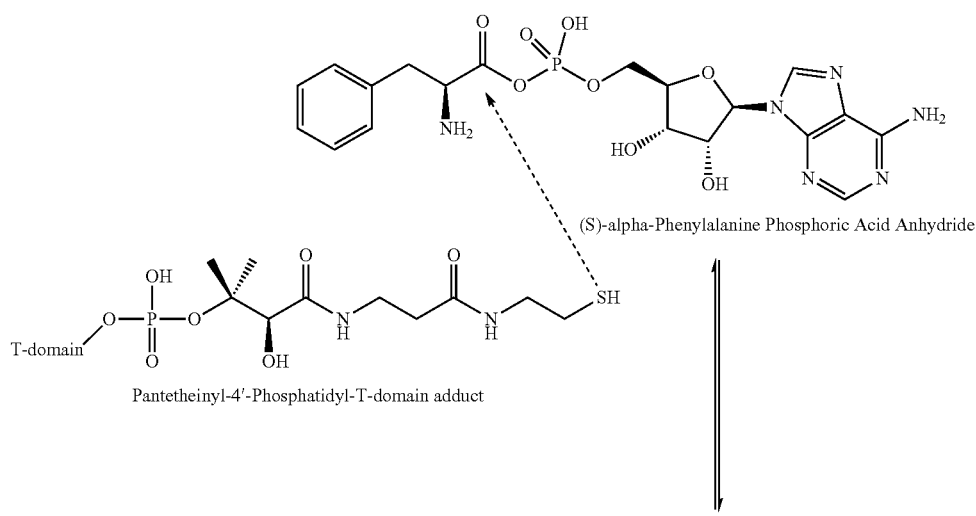

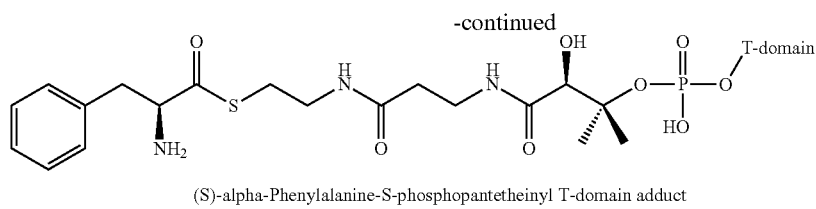

(S)-alpha-Phenylalanine-S-phosphopantetheinyl T-domain adduct

As described herein, the adenylation domain of TycA can surprisingly function as an amino phenylpropropanoyl:CoA ligase, making α-phenylalanyl-CoA, (R)-β-phenylalanyl-CoA, and (2R,3S)-phenylisoserinyl-CoA. The latter two are intermediates useful for making paclitaxel. For example, the reaction can proceed as follows.

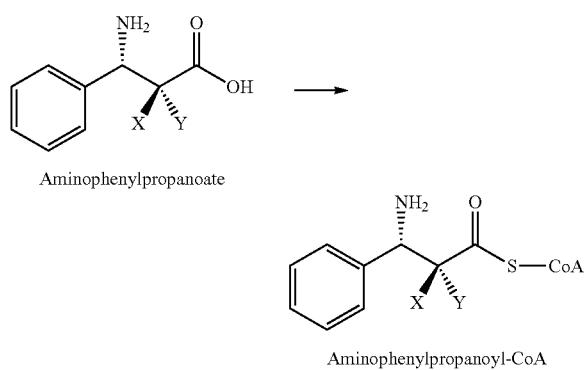

When the aminopropropanoate starting material is (R)-β-Phenylalanine, the X and Y are both hydrogen. However, when the aminopropropanoate starting material is (2R,3S)-Phenylisoserine, X is hydrogen, Y is OH.

As described herein, the conversion of an aminophenyl-propanoate to an aminophenylpropanoyl-CoA is surprisingly mediated by tyrocidine synthetase A (TycA), which functions as a CoA ligase. A variety of TycA ligases can be employed to catalyze such a reaction. For example, one amino acid sequence for wild type TycA with a histidine tail is provided below as SEQ ID NO:1.

```
  1 MVANQANLID NKRELEQHAL VPYAQGKSIH QLFEEQAEAF

41 PDRVAIVFEN RRLSYQELNR KANQLARALL EKGVQTDSIV

81 GVMMEKSIEN VIAILAVLKA GGAYVPIDIE YPRDRIQYIL

121 QDSQTKIVLT QKSVSQLVHD VGYSGEVVVL DEEQLDARET

161 ANLHQPSKPT DLAYVIYTSG TTGKPKGTML EHKGIANLQS

201 FFQNSFGVTE QDRIGLFASM SFDASVWEMF MALLSGASLY

241 ILSKQTIHDF AAFEHYLSEN ELTIITLPPT YLTHLTPERI

281 TSLRIMITAG SASSAPLVNK WKDKLRYINA YGPTETSICA

321 TIWEAPSNQL SVQSVPIGKP IQNTHIYIVN EDLQLLPTGS

361 EGELCIGGVG LARGYWNRPD LTAEKFVDNP FVPGEKMYRT

401 GDLAKWLTDG TIEFLGRIDH QVKIRGHRIE LGEIESVLLA

441 HEHITEAVVI AREDQHAGQY LCAYYISQQE ATPAQLRDYA

481 AQKLPAYMLP SYFVKLDKMP LTPNDKIDRK ALPEPDLTAN

521 QSQAAYHPPR TETESILVSI WQNVLGIEKI GIRDNFYSLG

561 GDSIQAIQVV ARLHSYQLKL ETKDLLNYPT IEQVALFVKS

601 TTRKSDQGII AGNVPLTPIQ KWFFGKNFTN TGHWNQSSVL

641 YRPEGFDPKV IQSVMDKIIE HHDALRMVYQ HENGNVVQHN

681 RGLGGQLYDF FSYNLTAQPD VQQAIEAETQ RLHSSMNLQE

721 GPLVKVALFQ TLHGDHLFLA IHHLVVDGIS WRILFEDLAT

761 GYAQALAGQA ISLPEKTDSF QSWSQWLQEY ANEADLLSEI

801 PYWESLESQA KNVSLPKDYE VTDCKQKSVR NMRIRLHPEE

841 TEQLLKHANQ AYQTEINDLL LAALGLAFAE WSKLAQIVIH

881 LEGHGREDII EQANVARTVG WFTSQYPVLL DLKQTAPLSD

921 YIKLTKENMR KIPRKGIGYD ILKHVTLPEN RGSLSFRVQP

961 EVTFNYLGQF DADMRTELFT RSPYSGGNTL GADGKNNLSP

1001 ESEVYTALNI TGLIEGGELV LTFSYSSEQY REESIQQLSQ

1041 SYQKHLLAII AHCTEKKEVE RTPSDFSVKG LQMEEMDDIF

1081 ELLANTLRGS RS
```

Such a TycA protein can have a histidine tag, for example, on its C-terminus. A nucleic acid sequence for this wild type, histidine-tagged TycA is provided below as SEQ ID NO:2.

```
  1 ATGGTAGCAA ATCAGGCCAA TCTCATCGAC AACAAGCGGG

41 AACTGGAGCA GCATGCGCTA GTTCCATATG CACAGGGCAA

81 GTCGATCCAT CAATTGTTCG AGGAACAAGC AGAGGCTTTT

121 CCAGACCGCG TTGCCATCGT TTTTGAAAAC AGGCGGCTTT

161 CGTATCAGGA GTTGAACAGG AAAGCCAATC AACTGGCAAG

201 AGCCTTGCTC GAAAAAGGGG TGCAAACAGA CAGCATCGTC

241 GGTGTGATGA TGGAGAAGTC CATCGAAAAT GTCATCGCGA

281 TTGCTGGCCGT TCTTAAAGCA GGCGGAGCCT ATGTGCCCAT

321 CGACATCGAA TATCCCCGCG ATCGCATCCA ATATATTTTG

361 CAGGATAGTC AAACGAAAAT CGTGCTTACC CAAAAAGCG

401 TCAGCCAGCT CGTGCATGAC GTCGGGTACA GCGGAGAGGT

441 AGTTGTACTC GACGAAGAAC AGTTGGACGC TCGCGAGACT

481 GCCAATCTGC ACCAGCCCAG CAAGCCTACG GATCTTGCCT

521 ATGTCATTTA CACCTCAGGC ACGACAGGCA AGCCAAAAGG

561 CACCATGCTT GAACATAAAG GCATCGCCAA TTTGCAATCC
```

```
-continued
 601 TTTTTCCAAA ATTCGTTTGG CGTCACCGAG CAAGACAGGA
 641 TCGGGCTTTT TGCCAGCATG TCGTTCGACG CATCCGTTTG
 681 GGAAATGTTC ATGGCTTTGC TGTCTGGCGC CAGCCTGTAC
 721 ATCCTTTCCA AACAGACGAT CCATGATTTC GCTGCATTTG
 761 AACACTATTT GAGTGAAAAT GAATTGACCA TCATCACACT
 801 GCCGCCGACT TATTTGACTC ACCTCACCCC AGAGCGCATC
 841 ACCTCGCTAC GCATCATGAT TACGGCAGGA TCAGCTTCCT
 881 CCGCACCCTT GGTAAACAAA TGGAAAGACA AACTCAGGTA
 921 CATAAATGCA TACGGCCCGA CGGAAACGAG CATTTGCGCG
 961 ACGATCTGGG AAGCCCCGTC CAATCAGCTC TCCGTGCAAT
1001 CGGTTCCGAT CGGCAAACCG ATTCAAAATA CACATATTTA
1041 TATCGTCAAT GAAGACTTGC AGCTACTGCC GACTGGCAGC
1081 GAAGGCGAAT TGTGCATCGG CGGAGTCGGC TTGGCAAGAG
1121 GCTATTGGAA TCGGCCCGAC TTGACCGCAG AAAAATTCGT
1161 AGACAATCCG TTCGTACCAG GCGAAAAAAT GTACCGCACA
1201 GGTGACTTGG CCAAATGGCT GACGGATGGA ACGATCGAGT
1241 TTCTCGGCAA AATCGACCAT CAGGTGAAAA TCAGAGGTCA
1281 TCGCATCGAG CTTGGCGAAA TCGAGTCTGT TTTGTTGGCA
1321 CATGAACACA TCACAGAGGC CGTGGTCATT GCCAGAGAGG
1361 ATCAACACGC GGGACAGTAT TTGTGCGCCT ATTATATTTC
1401 GCAACAAGAA GCAACTCCTG CGCAGCTCAG AGACTACGCC
1441 GCCCAGAAGC TTCCGGCTTA CATGCTGCCA TCTTATTTCG
1481 TCAAGCTGGA CAAAATGCCG CTTACGCCAA ATGACAAGAT
1521 CGACCGCAAA GCGTTGCCCG AGCCTGATCT TACGGCAAAC
1561 CAAAGCCAGG CTGCCTACCA TCCTCCGAGA ACCGAGACAG
1601 AATCGATTCT CGTCTCCATC TGGCAAAACG TTTTGGGAAT
1641 TGAAAAGATC GGGATTCGCG ATAATTTTTA CTCGCTCGGC
1681 GGAGATTCGA TCCAAGCGAT CCAGGTCGTG GCTCGTCTGC
1721 ATTCCTATCA ATTGAAGCTA GAGACGAAAG ACTTGCTGAA
1761 TTACCCGACG ATCGAGCAGG TTGCTCTTTT TGTCAAGAGC
1801 ACGACGAGAA AAAGCGATCA GGGCATCATC GCTGGAAACG
1841 TACCGCTTAC ACCCATTCAG AAGTGGTTTT TCGGGAAAAA
1881 CTTTACGAAT ACAGGCCATT GGAACCAATC GTCTGTGCTC
1921 TATCGCCCGG AAGGCTTTGA TCCTAAAGTC ATCCAAAGTG
1961 TCATGGACAA AATCATCGAA CACCACGACG GCTCCGCAT
2001 GGTCTATCAG CACGAAAACG GAAATGTCGT TCAGCACAAC
2041 CGCGGCTTGG GTGGACAATT ATACGATTTC TTCTCTTATA
2081 ATCTGACCGC GCAACCAGAC GTCCAGCAGG CGATCGAAGC
2121 AGAGACGCAA CGTCTGCACA GCAGCATGAA TTTGCAGGAA
2161 GGACCTCTGG TGAAGGTTGC CTTATTTCAG ACGTTACATG
2201 GCGATCATTT GTTTCTCGCA ATTCATCATT TGGTCGTGGA
2241 TGGCATTTCC TGGCGCATTT TGTTTGAAGA TTTGGCAACC
2281 GGATACGCGC AGGCACTTGC AGGGCAAGCG ATCAGTCTGC
2321 CCGAAAAAAC GGATTCTTTT CAAAGCTGGT CACAATGGTT
2361 GCAAGAATAT GCGAACGAGG CGGATTTGCT GAGCGAGATT
2401 CCGTACTGGG AGAGTCTCGA ATCGCAAGCA AAAAATGTGT
2441 CCCTGCCGAA AGACTATGAA GTGACCGACT GCAAACAAAA
2481 GAGCGTGCGA AACATGCGGA TACGGCTGCA CCCGGAAGAG
2521 ACCGAGCAGT TGTTGAAGCA CGCCAATCAG GCCTATCAAA
2561 CGGAAATCAA CGATCTGTTG TTGGCGGCGC TCGGCTTGGC
2601 TTTTGCGGAG TGGAGCAAGC TTGCGCAAAT CGTCATTCAT
2641 TTGGAGGGGC ACGGGCGCGA GGACATCATC GAACAGGCAA
2681 ACGTGGCCAG AACGGTCGGA TGGTTTACGT CGCAATATCC
2721 GGTATTGCTC GACTTGAAGC AAACCGCTCC CTTGTCCGAC
2761 TATATCAAGC TCACCAAAGA GAATATGCGG AAGATTCCTC
2801 GTAAAGGGAT CGGTTACGAC ATCTTGAAGC ATGTGACACT
2841 TCCAGAAAAT CGCGGTTCCT TATCCTTCCG CGTGCAGCCG
2881 GAAGTGACGT TCAACTACTT GGGACAGTTT GATGCGGACA
2921 TGAACGGA ACTGTTTACC CGCTCACCCT ACAGCGGCGG
2961 CAACACGTTA GGCGCAGATG GCAAAAACAA TCTGAGTCCT
3001 GAGTCAGAGG TGTACACCGC TTTGAATATA ACCGGATTGA
3041 TTGAAGGCGG AGAGCTCGTC CTCACATTCT CTTACAGCTC
3081 GGAGCAGTAT CGGGAAGAGT CCATCCAGCA ATTGAGCCAA
3121 AGTTATCAAA AGCATCTGCT TGCCATCATC GCGCATTGCA
3161 CCGAGAAAAA AGAAGTAGAG CGAACGCCCA GCGATTTCAG
3201 CGTCAAAGGT CTCCAAATGG AAGAAATGGA CGATATCTTC
3241 GAATTGCTTG CAAATACACT GCGCGGATCC AGATCTCATC
3281 ACCATCACCA TCACTAAGCT TAA
```

In some embodiments, the AMP binding domain of the TycA protein resides within amino acid positions from about 54 to about 449, or from about 402 to about 507. The acyl carrier function of the TycA protein can reside within amino acid positions from about 533 to about 599. The phosphopantetheine attachment site can reside within amino acid positions from about 537 to about 598, or at about position 563. The condensation domain can reside within amino acid positions from about 610 to about 913. The non-ribosomal peptide synthase domain can reside within amino acid positions from about 917 to about 1079.

For experiments described herein, this wild-type tycA cDNA encoding the A-, T-, and E-domains was subcloned into a pSU18 vector and heterologously expressed as a His$_6$-fusion in *Escherichia coli* BL21(DE3). However, the *E. coli* BL21 encodes the 4'-Phosphopantetheine transferase enzyme within its genome that can post-translationally couple 4'-phosphopantetheine (Ppant) to certain serine residues of various polypeptides (Jeong, et al., J. Mol. Biol. 394, 644-652 (2009)). Ser563 of TycA was changed to Ala563 (TycA-S563A) to prevent Ppant coupling at Ser563 of the T-domain and thus stall the reaction progress of TycA-S563A at the acyl-adenylate tetrahedral intermediate.

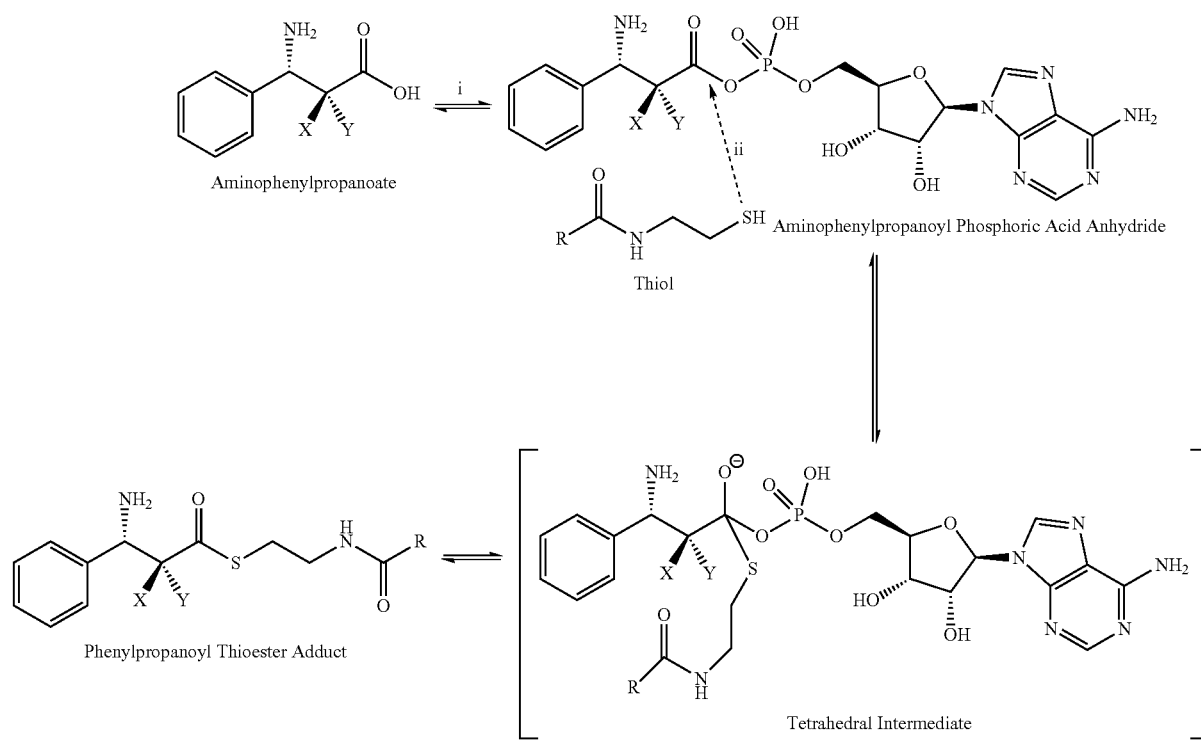

i = TycA, ATP, Mg$^{2+}$
ii = TycA catalyzed nucleophilic thioesterification

The T-domain mutant TycA-S563A has the following amino acid sequence (SEQ ID NO:3).

```
  1 MVANQANLID NKRELEQHAL VPYAQGKSIH QLFEEQAEAF
 41 PDRVAIVFEN RRLSYQELNR KANQLARALL EKGVQTDSIV
 81 GVMMEKSIEN VIAILAVLKA GGAYVPIDIE YPRDRIQYIL
121 QDSQTKIVLT QKSVSQLVHD VGYSGEVVVL DEEQLDARET
161 ANLHQPSKPT DLAYVIYTSG TTGKPKGTML EHKGIANLQS
201 FFQNSFGVTE QDRIGLFASM SFDASVWEMF MALLSGASLY
241 ILSKQTIHDF AAFEHYLSEN ELTIITLPPT YLTHLTPERI
281 TSLRIMITAG SASSAPLVNK WKDKLRYINA YGPTETSICA
321 TIWEAPSNQL SVQSVPIGKP IQNTHIYIVN EDLQLLPTGS
361 EGELCIGGVG LARGYWNRPD LTAEKFVDNP FVPGEKMYRT
401 GDLAKWLTDG TIEFLGRIDH QVKIRGHRIE LGEIESVLLA
441 HEHITEAVVI AREDQHAGQY LCAYYISQQE ATPAQLRDYA
481 AQKLPAYMLP SYFVKLDKMP LTPNDKIDRK ALPEPDLTAN
521 QSQAAYHPPR TETESILVSI WQNVLGIEKI GIRDNFYSLG
561 GDAIQAIQVV ARLHSYQLKL ETKDLLNYPT IEQVALFVKS
601 TTRKSDQGII AGNVPLTPIQ KWFFGKNFTN TGHWNQSSVL
641 YRPEGFDPKV IQSVMDKIIE HHDALRMVYQ HENGNVVQHN
681 RGLGGQLYDF FSYNLTAQPD VQQAIEAETQ RLHSSMNLQE
721 GPLVKVALFQ TLHGDHLFLA IHHLVVDGIS WRILFEDLAT
761 GYAQALAGQA ISLPEKTDSF QSWSQWLQEY ANEADLLSEI
801 PYWESLESQA KNVSLPKDYE VTDCKQKSVR NMRIRLHPEE
841 TEQLLKHANQ AYQTEINDLL LAALGLAFAE WSKLAQIVIH
881 LEGHGREDII EQANVARTVG WFTSQYPVLL DLKQTAPLSD
921 YIKLTKENMR KIPRKGIGYD ILKHVTLPEN RGSLSFRVQP
961 EVTFNYLGQF DADMRTELFT RSPYSGGNTL GADGKNNLSP
1001 ESEVYTALNI TGLIEGGELV LTFSYSSEQY REESIQQLSQ
1041 SYQKHLLAII AHCTEKKEVE RTPSDFSVKG LQMEEMDDIF
1081 ELLANTLRGS RSHHHHHH*
```

The alanine that replaces Ser-563 in the SEQ ID NO. 3 amino acid sequence is highlighted in bold and with underlining.

A nucleotide sequence for the mutant TycA S563A protein (SEQ ID NO:3) is provided below as SEQ ID NO:4.

```
  1 ATGGTAGCAA ATCAGGCCAA TCTCATCGAC AACAAGCGGG
 41 AACTGGAGCA GCATGCGCTA GTTCCATATG CACAGGGCAA
 81 GTCGATCCAT CAATTGTTCG AGGAACAAGC AGAGGCTTTT
121 CCAGACCGCG TTGCCATCGT TTTTGAAAAC AGGCGGCTTT
161 CGTATCAGGA GTTGAACAGG AAAGCCAATC AACTGGCAAG
```

```
201 AGCCTTGCTC GAAAAAGGGG TGCAAACAGA CAGCATCGTC
241 GGTGTGATGA TGGAGAAGTC CATCGAAAAT GTCATCGCGA
281 TTCTGGCCGT TCTTAAAGCA GGCGGAGCCT ATGTGCCCAT
321 CGACATCGAA TATCCCCGCG ATCGCATCCA ATATATTTTG
361 CAGGATAGTC AAACGAAAAT CGTGCTTACC CAAAAAAGCG
401 TCAGCCAGCT CGTGCATGAC GTCGGGTACA GCGGAGAGGT
441 AGTTGTACTC GACGAAGAAC AGTTGGACGC TCGCGAGACT
481 GCCAATCTGC ACCAGCCCAG CAAGCCTACG ATCTTGCCT
521 ATGTCATTTA CACCTCAGGC ACGACAGGCA AGCCAAAAGG
561 CACCATGCTT GAACATAAAG GCATCGCCAA TTTGCAATCC
601 TTTTTCCAAA ATTCGTTTGG CGTCACCGAG CAAGACAGGA
641 TCGGGCTTTT TGCCAGCATG TCGTTCGACG CATCCGTTTG
681 GGAAATGTTC ATGGCTTTGC TGTCTGGCGC CAGCCTGTAC
721 ATCCTTTCCA AACAGACGAT CCATGATTTC GCTGCATTTG
761 AACACTATTT GAGTGAAAAT GAATTGACCA TCATCACACT
801 GCCGCCGACT TATTTGACTC ACCTCACCCC AGAGCGCATC
841 ACCTCGCTAC GCATCATGAT TACGGCAGGA TCAGCTTCCT
881 CCGCACCCTT GGTAAACAAA TGGAAAGACA AACTCAGGTA
921 CATAAATGCA TACGGCCCGA CGGAAACGAG CATTTGCGCG
961 ACGATCTGGG AAGCCCCGTC CAATCAGCTC TCCGTGCAAT
1001 CGGTTCCGAT CGGCAAACCG ATTCAAAATA CACATATTTA
1041 TATCGTCAAT GAAGACTTGC AGCTACTGCC GACTGGCAGC
1081 GAAGGCGAAT TGTGCATCGG CGGAGTCGGC TTGGCAAGAG
1121 GCTATTGGAA TCGGCCCGAC TTGACCGCAG AAAAATTCGT
1161 AGACAATCCG TTCGTACCAG GCGAAAAAAT GTACCGCACA
1201 GGTGACTTGG CCAAATGGCT GACGGATGGA ACGATCGAGT
1241 TTCTCGGCAG AATCGACCAT CAGGTGAAAA TCAGAGGTCA
1281 TCGCATCGAG CTTGGCGAAA TCGAGTCTGT TTTGTTGGCA
1321 CATGAACACA TCACAGAGGC CGTGGTCATT GCCAGAGAGG
1361 ATCAACACGC GGGACAGTAT TTGTGCGCCT ATTATATTTC
1401 GCAACAAGAA GCAACTCCTG CGCAGCTCAG AGACTACGCC
1441 GCCCAGAAGC TTCCGGCTTA CATGCTGCCA TCTTATTTCG
1481 TCAAGCTGGA CAAAATGCCG CTTACGCCAA ATGACAAGAT
1521 CGACCGCAAA GCGTTGCCCG AGCCTGATCT TACGGCAAAC
1561 CAAAGCCAGG CTGCCTACCA TCCTCCGAGA ACCGAGACAG
1601 AATCGATTCT CGTCTCCATC TGGCAAAACG TTTTGGGAAT
1641 TGAAAAGATC GGGATTCGCG ATAATTTTTA CTCGCTCGGC
1681 GGAGATGCGA TCCAAGCGAT CCAGGTCGTG GCTCGTCTGC
1721 ATTCCTATCA ATTGAAGCTA GAGACGAAAG ACTTGCTGAA
1761 TTACCCGACG ATCGAGCAGG TTGCTCTTTT TGTCAAGAGC
1801 ACGACGAGAA AAAGCGATCA GGGCATCATC GCTGGAAACG
1841 TACCGCTTAC ACCCATTCAG AAGTGGTTTT TCGGGAAAAA
1881 CTTTACGAAT ACAGGCCATT GGAACCAATC GTCTGTGCTC
1921 TATCGCCCGG AAGGCTTTGA TCCTAAAGTC ATCCAAAGTG
1961 TCATGGACAA AATCATCGAA CACCACGACG CGCTCCGCAT
2001 GGTCTATCAG CACGAAAACG GAAATGTCGT TCAGCACAAC
2041 CGCGGCTTGG GTGGACAATT ATACGATTTC TTCTCTTATA
2081 ATCTGACCGC GCAACCAGAC GTCCAGCAGG CGATCGAAGC
2121 AGAGACGCAA CGTCTGCACA GCAGCATGAA TTTGCAGGAA
2161 GGACCTCTGG TGAAGGTTGC CTTATTTCAG ACGTTACATG
2201 GCGATCATTT GTTTCTCGCA ATTCATCATT TGGTCGTGGA
2241 TGGCATTTCC TGGCGCATTT TGTTTGAAGA TTTGGCAACC
2281 GGATACGCGC AGGCACTTGC AGGGCAAGCG ATCAGTCTGC
2321 CCGAAAAAAC GGATTCTTTT CAAAGCTGGT CACAATGGTT
2361 GCAAGAATAT GCGAACGAGG CGGATTTGCT GAGCGAGATT
2401 CCGTACTGGG AGAGTCTCGA ATCGCAAGCA AAAAATGTGT
2441 CCCTGCCGAA AGACTATGAA GTGACCGACT GCAAACAAAA
2481 GAGCGTGCGA AACATGCGGA TACGGCTGCA CCCGGAAGAG
2521 ACCGAGCAGT TGTTGAAGCA CGCCAATCAG GCCTATCAAA
2561 CGGAAATCAA CGATCTGTTG TTGGCGGCGC TCGGCTTGGC
2601 TTTTGCGGAG TGGAGCAAGC TTGCGCAAAT CGTCATTCAT
2641 TTGGAGGGGC ACGGGCGCGA GGACATCATC GAACAGGCAA
2681 ACGTGGCCAG AACGGTCGGA TGGTTTACGT CGCAATATCC
2721 GGTATTGCTC GACTTGAAGC AAACCGCTCC CTTGTCCGAC
2761 TATATCAAGC TCACCAAAGA GAATATGCGG AAGATTCCTC
2801 GTAAAGGGAT CGGTTACGAC ATCTTGAAGC ATGTGACACT
2841 TCCAGAAAAT CGCGGTTCCT TATCCTTCCG CGTGCAGCCG
2881 GAAGTGACGT TCAACTACTT GGGACAGTTT GATGCGGACA
2921 TGAGAACGGA ACTGTTTACC CGCTCACCCT ACAGCGGCGG
2961 CAACACGTTA GGCGCAGATG GCAAAAACAA TCTGAGTCCT
3001 GAGTCAGAGG TGTACACCGC TTTGAATATA ACCGGATTGA
3041 TTGAAGGCGG AGAGCTCGTC CTCACATTCT CTTACAGCTC
3081 GGAGCAGTAT CGGGAAGAGT CCATCCAGCA ATTGAGCCAA
3121 AGTTATCAAA AGCATCTGCT TGCCATCATC GCGCATTGCA
3161 CCGAGAAAAA AGAAGTAGAG CGAACGCCCA GCGATTTCAG
3201 CGTCAAAGGT CTCCAAATGG AAGAAATGGA CGATATCTTC
3241 GAATTGCTTG CAAATACACT GCGCGGATCC AGATCTCATC
3281 ACCATCACCA TCACTAAGCT TAA
```

The T-domain mutant TycA-S563A was also subcloned into a pSU18 vector and heterologously expressed as a His6-fusion in *Escherichia coli* BL21(DE3).

Related TycA enzymes can also be employed to catalyze the formation of an aminopropanyl-CoA. At least some amino acid and nucleic acid sequences for proteins related to the SEQ ID NO:1 TycA sequence are available from the National Center for Biotechnology Information (NCBI) database (see, e.g., the website at ncbi.nlm nih.gov). For example, an amino acid sequence for Tyrocidine synthase 1 from *Brevibacillus parabrevis* is available from the NCBI database as accession number P09095.2 (GI:6175106) and is provided below as SEQ ID NO:5.

```
   1 MLANQANLID NKRELEQHAL VPYAQGKSIH QLFEEQAEAF
  61 PDRVAIVFEN RRLSYQELNR KANQLARALL EKGVQTDSIV
  81 GVMMEKSIEN VIAILAVLKA GGAYVPIDIE YPRDRIQYIL
 121 QDSQTKIVLT QKSVSQLVHD VGYSGEVVVL DEEQLDARET
 161 ANLHQPSKPT DLAYVIYTSG TTGKPKGTML EHKGIANLQS
 201 FFQNSFGVTE QDRIGLFASM SFDASVWEMF MALLSGASLY
 241 ILSKQTIHDF AAFEHYLSEN ELTIITLPPT YLTHLTPERI
 281 TSLRIMITAG SASSAPLVNK WKDKLRYINA YGPTETSICA
 321 TIWEAPSNQL SVQSVPIGKP IQNTHIYIVN EDLQLLPTGS
 361 EGELCIGGVG LARGYWNRPD LTAEKFVDNP FVPGEKMYRT
 401 GDLAKWLTDG TIEFLGRIDH QVKIRGHRIE LGEIESVLLA
 441 HEHITEAVVI AREDQHAGQY LCAYYISQQE ATPAQLRDYA
 481 AQKLPAYMLP SYFVKLDKMP LTPNDKIDRK ALPEPDLTAN
 521 QSQAAYHPPR TETESILVSI WQNVLGIEKI GIRDNFYSLG
 561 GDSIQAIQVV ARLHSYQLKL ETKDLLNYPT IEQVALFVKS
 601 TTRKSDQGII AGNVPLTPIQ KWFFGKNFTN TGHWNQSSVL
 641 YRPEGFDPKV IQSVMDKIIE HHDALRMVYQ HENGNVVQHN
 681 RGLGGQLYDF FSYNLTAQPD VQQAIEAETQ RLHSSMNLQE
 721 GPLVKVALFQ TLHGDHLFLA IHHLVVDGIS WRILFEDLAT
 761 GYAQALAGQA ISLPEKTDSF QSWSQWLQEY ANEADLLSEI
 781 PYWESLESQA KNVSLPKDYE VTDCKQKSVR NMRIRLHPEE
 841 TEQLLKHANQ AYQTEINDLL LAALGLAFAE WSKLAQIVIH
 881 LEGHGREDII EQANVARTVG WFTSQYPVLL DLKQTAPLSD
 901 YIKLTKENMR KIPRKGIGYD ILKHVTLPEN RGSLSFRVQP
 961 EVTFNYLGQF DADMRTELFT RSPYSGGNTL GADGKNNLSP
1001 ESEVYTALNI TGLIEGGELV LTFSYSSEQY REESIQQLSQ
1041 SYQKHLLAII AHCTEKKEVE RTPSDFSVKG LQMEEMDDIF
1081 ELLANTLR
```

Another amino acid sequence for a protein related to TycA is available from the NCBI database as accession number CAA31623.1 (GI:39401; also from *Brevibacillus parabrevis*) and is provided below as SEQ ID NO:6.

```
   1 MLANQANLID NKRELEQHAL VPYAQGKSIH QLFEEQAEAF
  41 PDRVAIVFEN RRLSYQELNR KANQLARALL EKGVQTDSIV
  81 GVMMEKSIEN VIAILAVLKA GGAYVPIDIE YPRDRIQYIL
 121 QDSQTKIVLT QKSVSQLVHD VGYSGEVVVL DEEQLDARET
 161 ANLHQPSKPT DLAYVIYTSG TTGKPKGTML EHKGIAICNP
 201 FSKIRLASPS KTGSGFLPAC RSTHPFGKCS WLCCCLAPRVH
 241 PSKQTIHDFA AFEHYLSENE LTIITLPPTY LTHLTPERIT
 281 SLRIMITAGS ASSAPLVNKW KDKLRYINAY GPTETSICAT
 321 IWEAPSNQLS VQSVPIGKPI QNTHIYIVNE DLQLLPTADE
 361 GELCIGGVGL ARGYWNRPDL TAEKFVDNPF VPGEKMYRTG
 401 DLAKWLTDGT IEFLGRIDHQ VKIRGHRIEL GEIESVLLAH
 441 EHITEAVVIA REDQHAGQYL CAYYISQQEA TPAQLRDYAA
 481 QKLPAYMLPS YFVKLDKMPL TPNDKIDRKA LPEPDLTANQ
 521 SQAAYHPPRT ETESILVSIW QNVLGIEKIG IRDNFYSLGG
 561 DSIQAIQVVA RLHSYQLKLE TKDLLNYPTI EQVALFVKST
 601 TRKSDQGIIA GNVPLTPIQK WFFGKNFTNT GHWNQSSVLY
 641 RPEGFDPKVI QSVMDKIIEH HDAVRMVYQH ENGNVVQHNR
 681 GLGGQLYDFF SYNLTAQPDV QQAIEAETQR LHSSMNLQEG
 721 PLVKVALFQT LHGDHFFLAI HHLVVDGISW RILFKIWQPD
 761 TRRHLQGKRS VCPKKRILFK AGHNGCKNNA NEADLLSEIP
 801 YWESLESQAK NVSLPKDYEV TDCKQKSVRN MRIRLHPEET
 841 EQLLKHANQA YQTEINDLLL AALGLAFAEW SKLAKSSFIW
 881 RGTGARTSSN RQTVARTVGW FTSQYPVLLD LKQTAPLSDY
 921 IKLTKENMRK IPRKGIGYDI LKHVTLPENR GSLSFRVQPE
 961 VTFNYLGQFD ADMRTELFTR SPYSGGNTLG ADGKNNLSPE
1001 SEVYTALNIT GLIEGGELVL TFSYSSEQYR EESIQQLSQS
1041 YQKHLLAIIA HCTEKKEVER TPSDFSVKGL QMEEMDDIFE
1081 LLANTLR
```

A nucleic acid sequence for the SEQ ID NO:6 protein is available in the NCBI database as accession number X13237.1 (GI:39400; *Brevibacillus brevis*), and is provided below as SEQ ID NO:7.

```
   1 CTGGTGGATC GCAAAGTACA TGCCAAACTG CTGGTGGATT
  41 TTCCTTGAAC CAAATTTCGC TGGCAGCCAG CATGGTTCAA
  81 ACCTTTTCTC TAAAAAGCTG CGTCACGTCA AAAAGAGGG
 121 GGTAGGAATT GTGCCTTTTT ATCACATGCC TTTTTACGAA
 161 AGTCTGCGGA CTGATCAGGA CAATAGCTGC TGATCCAGAT
 201 AGGCAGCACA CAGGAAAACA GCCTCTCGTT TTTCCGTAGA
 241 AGAAAATTCC TGTTTTCCCA GTATAAAGCA TTATATGGCT
 281 TGTGAACATA TAAAAATTTT AATGTTATGA AATATTTAT
 321 CGTCAAAATA TAGCCGTACG CTTTCCTTTT TTATAGACAA
 361 GTTGAAAAGG AAAAATGTTG CAGCGCCGAA ACGAGCCAAT
 401 CACTGGCTTC ACCAAAGGGA AAAACACGTG TGCCGCTTAT
 441 TGATTACGCA AGCGGGAGCA GGTTTGCCAA GCAAAACTTG
 481 GATTTACGTA AAAGGTTGT AAAAAAACTT GTTGAATTTT
```

-continued

```
 521 TTGCAAAATA TCCCTATTTT TTAATCGACT TCCAATTTTT
 561 CTCTGCTATA ATGAGTTTCA GCGTCAGTAA CCTAGTGCTT
 601 TCAGCCTGTC AGCCGATCGG GGAACTTCCT GTGATTGTTT
 641 TCATGCAAAT CAGTTTTCCT TCGTTCGCAG CGTAAGCAGG
 681 CGTATCCGGC AGCGGAATAC CAGCACCCAT TTTCCGCTAC
 721 AGCATGAGCA AATATGACT TTAGTATGAA GGGAATTTCC
 761 CAGAAACAGG AAATTTTCTT GTTGTTAAAA TTACCCAAAT
 801 GATGGAAAAT GGGAAATTGG AATGGAACGT TGACCTTGCC
 841 TGTCTCTTGT TGGCAACCAT TCGTCACAC TTCATGATAA
 881 GCAGAAGTAA TTCCATTATC GGAGGGGACA TATGTTAGCA
 921 AATCAGGCCA ATCTCATCGA CAACAAGCGG GAACTGGAGC
 961 AGCATGCGCT AGTTCCATAT GCACAGGGCA AGTCGATCCA
1001 TCAATTGTTC GAGGAACAAG CAGAGGCTTT TCCAGACCGC
1041 GTTGCCATCG TTTTTGAAAA CAGGCGGCTT TCGTATCAGG
1081 AGTTGAACAG GAAAGCCAAT CAACTGGCAA GAGCCTTGCT
1121 CGAAAAAGGG GTGCAAACAG ACAGCATCGT CGGTGTGATG
1161 ATGGAGAAGT CCATCGAAAA TGTCATCGCG ATTCTGGCCG
1201 TTCTTAAAGC AGGCGGAGCC TATGTGCCCA TCGACATCGA
1241 ATATCCCCGC GATCGCATCC AATATATTTT GCAGGATAGT
1281 CAAACGAAAA TCGTGCTTAC CCAAAAAAGC GTCAGCCAGC
1321 TCGTGCATGA CGTCGGGTAC AGCGGAGAGG TAGTTGTACT
1361 CGACGAAGAA CAGTTGGACG CTCGCGAGAC TGCCAATCTG
1401 CACCAGCCCA GCAAGCCTAC GGATCTTGCC TATGTCATTT
1441 ACACCTCAGG CACGACAGGC AAGCCAAAAG CACCATGCT
1481 TGAACATAAA GGCATCGCAA TTTGCAATCC TTTTTCCAAA
1521 ATTCGTTTGG CGTCACCGAG CAAGACAGGA TCGGGCTTTT
1561 TGCCAGCATG TCGTTCGACG CATCCGTTTG GGAAATGTTC
1601 ATGGCTTTGC TGTCTGGCGC CACGTGTACA TCCTTCCAAA
1641 CAGACGATCC ATGATTTCGC TGCATTTGAA CACTATTTGA
1681 GTGAAAATGA ATTGACCATC ATCACACTGC CGCCGACTTA
1721 TTTGACTCAC CTCACCCCAG AGCGCATCAC CTCGCTACGC
1761 ATCATGATTA CGGCAGGATC AGCTTCCTCC GCACCCTTGG
1801 TAAACAAATG GAAAGACAAA CTCAGGTACA TAAATGCATA
1841 CGGCCCGACG GAAACGAGCA TTTGCGCGAC GATCTGGGAA
1881 GCCCCGTCCA ATCAGCTCTC CGTGCAATCG GTTCCGATCG
1921 GCAAACCGAT TCAAAATACA CATATTTATA TCGTCAATGA
1961 AGACTTGCAG CTACTGCCGA CTGCGGACGA AGGCGAATTG
2001 TGCATCGGCG GAGTCGGCTT GGCAAGAGGC TATTGGAATC
2041 GGCCCGACTT GACCGCAGAA AAATTCGTAG CAATCCGTT
2081 CGTACCAGGC GAAAAAATGT ACCGCACAGG TGACTTGGCC
2121 AAATGGCTGA CGGATGGAAC GATCGAGTTT CTCGGCAGAA
2161 TCGACCATCA GGTGAAAATC AGAGGTCATC GCATCGAGCT
2201 TGGCGAAATC GAGTCTGTTT TGTTGGCACA TGAACACATC
2241 ACAGAGGCCG TGGTCATTGC CAGAGAGGAT CAACACGCGG
2281 GACAGTATTT GTGCGCCTAT TATATTTCGC AACAAGAAGC
2321 AACTCCTGCG CAGCTCAGAG ACTACGCCGC CCAGAAGCTT
2361 CCGGCTTACA TGCTGCCATC TTATTTCGTC AAGCTGGACA
2401 AAATGCCGCT TACGCCAAAT GACAAGATCG ACCGCAAAGC
2441 GTTGCCCGAG CCTGATCTTA CGGCAAACCA AAGCCAGGCT
2481 GCCTACCATC CTCCGAGAAC CGAGACAGAA TCGATTCTCG
2521 TCTCCATCTG GCAAACGTT TTGGGAATTG AAAAGATCGG
2561 GATTCGCGAT AATTTTTACT CGCTCGGCGG AGATTCGATC
2601 CAAGCGATCC AGGTCGTGGC TCGTCTGCAT TCCTATCAAT
2641 TGAAGCTAGA GACGAAAGAC TTGCTGAATT ACCCGACGAT
2681 CGAGCAGGTT GCTCTTTTTG TCAAGAGCAC GACGAGAAAA
2721 AGCGATCAGG GCATCATCGC TGGAAACGTA CCGCTTACAC
2761 CCATTCAGAA GTGGTTTTTC GGGAAAAACT TTACGAATAC
2801 AGGCCATTGG AACCAATCGT CTGTGCTCTA TCGCCCGGAA
2841 GGCTTTGATC CTAAAGTCAT CCAAAGTGTC ATGGACAAAA
2881 TCATCGAACA CCACGACGCC GTCCGCATGG TCTATCAGCA
2921 CGAAAACGGA AATGTCGTTC AGCACAACCG CGGCTTGGGT
2961 GGACAATTAT ACGATTTCTT CTCTTATAAT CTGACCGCGC
3001 AACCAGACGT CCAGCAGGCG ATCGAAGCAG AGACGCAACG
3041 TCTGCACAGC AGCATGAATT TGCAGGAAGG ACCTCTGGTG
3081 AAGGTTGCCT TATTTCAGAC GTTACATGGC GATCATTTCT
3121 TTCTCGCAAT TCATCATTTG GTCGTGGATG GCATTTCCTG
3161 GCGCATTTTG TTTAAGATTT GGCAACCGGA TACGCGCAGG
3321 CACTTGCAGG GCAAGCGATC AGTCTGCCCG AAAAAACGGA
3241 TTCTTTTCAA AGCTGGTCAC AATGGTTGCA AGAATAATGC
3281 GAACGAGGCG GATTTGCTGA GCGAGATTCC GTACTGGGAG
3321 AGTCTCGAAT CGCAAGCAAA AAATGTGTCC CTGCCGAAAG
3361 ACTATGAAGT GACCGACTGC AAACAAAAGA GCGTGCGAAA
3401 CATGCGGATA CGGCTGCACC CGGAAGAGAC CGAGCAGTTG
3441 TTGAAGCACG CCAATCAGGC CTATCAAACG GAAATCAACG
3481 ATCTGTTGTT GGCGGCGCTC GGCTTGGCTT TTGCGGAGTG
3521 GAGCAAGCTT GCGAAATCGT CATTCATTTG GAGGGGCACG
3561 GGCGCGAGGA CATCATCGAA CAGGCAAACG GTGGCCAGAA
3601 CGGTCGGATG GTTTACGTCG CAATATCCGG TATTGCTCGA
3641 CTTGAAGCAA ACCGCTCCCT TGTCCGACTA TATCAAGCTC
3681 ACCAAAGAGA ATATGCGGAA GATTCCTCGT AAAGGGATCG
3721 GTTACGACAT CTTGAAGCAT GTGACACTTC CAGAAAATCG
```

-continued

```
3761 CGGTTCCTTA TCCTTCCGCG TGCAGCCGGA AGTGACGTTC

3801 AACTACTTGG GACAGTTTGA TGCGGACATG AGAACGGAAC

3841 TGTTTACCCG CTCACCCTAC AGCGGCGGCA ACACGTTAGG

3881 CGCAGATGGC AAAAACAATC TGAGTCCTGA GTCAGAGGTG

3921 TACACCGCTT TGAATATAAC CGGATTGATT GAAGGCGGAG

3961 AGCTCGTCCT CACATTCTCT TACAGCTCGG AGCAGTATCG

4001 GGAAGAGTCC ATCCAGCAAT TGAGCCAAAG TTATCAAAAG

4041 CATCTGCTTG CCATCATCGC GCATTGCACC GAGAAAAAAG

4081 AAGTAGAGCG AACGCCCAGC GATTTCAGCG TCAAAGGTCT

4121 CCAAATGGAA GAAATGGACG ATATCTTCGA ATTGCTTGCA

4161 AATACACTGC GCTAAACAGA TGTTGGCCAC CATTTTCAGG

4201 GGCAACTGCG TGCTTTCATT CCCATTTTTA TACATTTATA

4241 ACAAATAAAG ATATATCCGA GGTGCCGTAA TGAGTGTATT

4281 TAGCAAAGAA CAAGTTCAGG ATATGTATGC GTTGAC
```

The coding region of the TycA related protein is at nucleotide positions from about 912 to about 4175 within the SEQ ID NO:7 sequence.

Related Sequences

As described herein, TycA can catalyze the formation of aminophenylpropanoyl-CoA in a reaction that proceeds as follows.

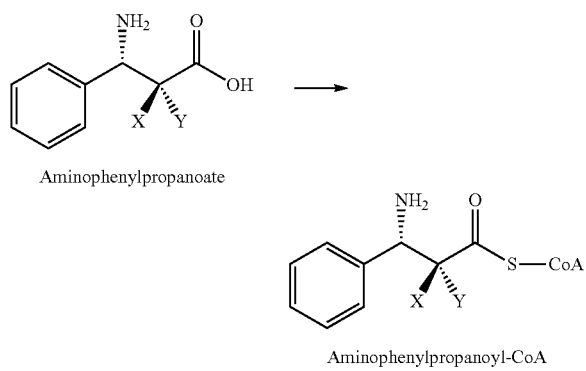

Aminophenylpropanoate

Aminophenylpropanoyl-CoA

In some embodiments, proteins related to TycA can also catalyze formation of aminophenylpropanoyl-CoA. Such related TycA protein can have sequences that share at least about 85% sequence identity with any of the TycA sequences described herein.

Proteins that share at least about 85% sequence identity with any of the TycA sequences described herein can be obtained by identifying nucleic acids with at least 85% sequence identity to the TycA nucleic acids described herein. Such nucleic acids can readily be identified, isolated and used to facilitate production of aminopropanyl-CoA. Such nucleic acids can encode or hybridize to TycA nucleic acids, or fragments thereof.

For example, related nucleic acids can be isolated and identified by mutation of the SEQ ID NO:1, SEQ ID NO:3, SEQ ID NO:5, and/or SEQ ID NO: 6 amino acid sequences and/or by hybridization to DNA and/or RNA isolated from other species using the SEQ ID NO:2, SEQ ID NO:4, and/or SEQ ID NO:7 nucleic acids (or fragments thereof) as probes. Sequences of the TycA proteins (e.g., SEQ ID NO:1, 3, and/or 6) or nucleic acids (e.g., SEQ ID NO:2, SEQ ID NO:4, and/or SEQ ID NO:7) can also be examined and used a basis for designing alternative TycA proteins and nucleic acids.

In some embodiments, the TycA nucleic acids that encode useful TycA activities include any nucleic acid that can selectively hybridize to a nucleic acid with any of the SEQ ID NO:2, 4 and 7 sequences.

The term "selectively hybridize" includes hybridization, under stringent hybridization conditions, of a nucleic acid sequence to a specified nucleic acid target sequence (e.g., SEQ ID NO:2, SEQ ID NO:4, and/or SEQ ID NO:7) to a detectably greater degree (e.g., at least 2-fold over background) than its hybridization to non-target nucleic acid sequences. Such selective hybridization substantially excludes non-target nucleic acids.

Related TycA nucleic acids sequences typically have about at least 40% sequence identity, or at least 50% sequence identity, or at least 60% sequence identity, or at least 70% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with any of SEQ ID NO:2, SEQ ID NO:4, and/or SEQ ID NO:7. In some embodiments, a selectively hybridizing sequence has about at least about 80% or at least about 85% sequence identity or complementarity with any of SEQ ID NO:2, SEQ ID NO:4, and/or SEQ ID NO:7.

Note that if a value of a variable that is necessarily an integer (e.g., the number of nucleotides or amino acids in a nucleic acid or protein), is described as a range, e.g., 80-99% sequence identity what is meant is that the value can be any integer between 80 and 99 inclusive, i.e., 80, 81, 82, 83, 84, 85, 86, 87, 88, 89, 90, 91, 92, 93, 94, 95, 96, 97, 98 or 99, or any range between 80 and 99 inclusive, e.g., 81-99%, 81-98%, 82-99%, etc.

In some embodiments, the nucleic acids used in the methods provided herein can include fragments of TycA nucleic acids. For example, the nucleic acids of the invention include those with about 300 of the same nucleotides as any of the SEQ ID NO:2, 4, 6, 8, 10, 12, 14 and 18 sequences, or about 400 of the same nucleotides as any of the SEQ ID NO: 2, 4, and 7 sequences, or about 500 of the same nucleotides as any of the SEQ ID NO: 2, 4, and 7 sequences, or about 600 of the same nucleotides as any of the SEQ ID NO: 2, 4, and 7 sequences, or about 700 of the same nucleotides as any of the SEQ ID NO: 2, 4, and 7 sequences, or about 800 of the same nucleotides as any of the SEQ ID NO: 2, 4, and 7 sequences, or about 900 of the same nucleotides as any of the SEQ ID NO: 2, 4, and 7 sequences, or about 1000 of the same nucleotides as any of the SEQ ID NO:2, 4, and 7 sequences, or about 1100 of the same nucleotides as any of the SEQ ID NO: 2, 4, and 7 sequences, or about 500-1100 of the same nucleotides as any of the SEQ ID NO: 2, 4, and 7 sequences. The identical nucleotides can be distributed throughout the nucleic acid, and need not be contiguous. For example, the nucleic acid sequence of a TycA nucleic acid can be optimized for expression in a particular plant species by altering selected codons to encode the same amino acid but use nucleotide codons that are more easily 'read' by the transcription/translation machinery of a selected plant species.

In some embodiments, related nucleic acid hybridize to the nucleic acids described herein under "stringent conditions" or "stringent hybridization conditions."

The terms "stringent conditions" or "stringent hybridization conditions" include conditions under which a probe will hybridize to its target sequence to a detectably greater degree than other sequences (e.g., at least 2-fold over background). Stringent conditions are somewhat sequence-dependent and can vary in different circumstances. By controlling the stringency of the hybridization and/or washing conditions, target sequences can be hybridized that have up to 100% complementarity to the probe or inhibitory nucleic acid (homologous probing). Alternatively, stringency conditions can be adjusted to allow some mismatching in sequences so that lower degrees of sequence similarity are detected (heterologous probing).

A probe for identifying and/or isolating a related nucleic acid can be approximately 15-500 nucleotides in length, but can vary greatly in length from about 17 nucleotides to equal to the entire length of the target sequence. In some embodiments, the probe is about 10-50 nucleotides in length, or about 15-50 nucleotides in length, or about 16-45 nucleotides in length, or about 18-25 nucleotides in length.

Typically, stringent conditions will be those where the salt concentration is less than about 1.5 M Na ion (or other salts), typically about 0.01 to 1.0 M Na ion concentration (or other salts), at pH 7.0 to 8.3 and the temperature is at least about 30° C. for shorter probes (e.g., 10 to 50 nucleotides) and at least about 60° C. for longer probes (e.g., greater than 50 nucleotides). Stringent conditions may also be achieved with the addition of destabilizing agents such as formamide or Denhardt's solution. Exemplary low stringency conditions include hybridization with a buffer solution of 30 to 35% formamide, 1M NaCl, 1% SDS (sodium dodecyl sulfate) at 37° C., and a wash in 1×SSC to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically a function of post-hybridization washes, where the factors controlling hybridization include the ionic strength and temperature of the final wash solution.

For DNA-DNA hybrids, the $T_m$ can be approximated from the equation of Meinkoth and Wahl (Anal. Biochem. 138: 267-84 (1984)):

$$T_m=81.5° C.+16.6(\log M)+0.41(\% GC)-0.61(\% \text{formamide})-500/L$$

where M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$ is reduced by about 1° C. for each 1% of mismatching. Thus, the $T_m$, hybridization and/or wash conditions can be adjusted to hybridize to sequences of the desired sequence identity. For example, if sequences with greater than or equal to 90% sequence identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can include hybridization and/or a wash at 1, 2, 3 or 4° C. lower than the thermal melting point ($T_m$). Moderately stringent conditions can include hybridization and/or a wash at 6, 7, 8, 9 or 10° C. lower than the thermal melting point ($T_m$). Low stringency conditions can include hybridization and/or a wash at 11, 12, 13, 14, 15 or 20° C. lower than the thermal melting point ($T_m$). Using the equation, hybridization and wash compositions, and a desired $T_m$, those of ordinary skill can identify and isolate nucleic acids with sequences related to any of the SEQ ID NO:2, 4 and 6 sequences. Similarly, those of ordinary skill can identify and isolate inhibitory nucleic acids with sequences that effectively inhibit the expression of a nucleic acid that includes any of the SEQ ID NO:2, 4 and 6 sequences.

Those of skill in the art also understand how to vary the hybridization and/or wash solutions to isolate desirable nucleic acids. For example, if the desired degree of mismatching results in a $T_m$ of less than 45° C. (aqueous solution) or 32° C. (formamide solution) it is preferred to increase the SSC concentration so that a higher temperature can be used.

An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part 1, chapter 2, "Overview of principles of hybridization and the strategy of nucleic acid probe assays," Elsevier, N.Y. (1993); and in CURRENT PROTOCOLS IN MOLECULAR BIOLOGY, chapter 2, Ausubel, et al., eds, Greene Publishing and Wiley-Interscience, New York (1995).

Unless otherwise stated, in the present application, high stringency is defined as a wash in 0.1×SSC, 0.1% SDS at 65° C. High stringency hybridization can include hybridization in 4×SSC, 5×Denhardt's (5 g Ficoll, 5 g polyvinylpyrrolidone, 5 g bovine serum albumin in 500 ml of water), 0.1 mg/ml boiled salmon sperm DNA, and 25 mM Na phosphate at 65° C., followed by a wash in 0.1×SSC, 0.1% SDS at 65° C.

The following terms are used to describe the sequence relationships between two or more nucleic acids or nucleic acids or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. The reference sequence can be a nucleic acid sequence (e.g., any of the SEQ ID NO:2, 4, and 7 nucleic acid sequences) or an amino acid sequence (e.g., any of the SEQ ID NO:1, 3, 5, and 6 amino acid sequences). A reference sequence may be a subset or the entirety of a specified sequence. For example, a reference sequence may be a segment of a full-length cDNA or of a genomic DNA sequence, or the complete cDNA or complete genomic DNA sequence, or a domain of a polypeptide sequence.

As used herein, "comparison window" refers to a contiguous and specified segment of a nucleic acid or an amino acid sequence, wherein the nucleic acid/amino acid sequence can be compared to a reference sequence and wherein the portion of the nucleic acid/amino acid sequence in the comparison window may comprise additions or deletions (i.e., gaps) compared to the reference sequence (which does not comprise additions or deletions) for optimal alignment of the two sequences. The comparison window can vary for nucleic acid and polypeptide sequences. Generally, for nucleic acids, the comparison window is at least 16 contiguous nucleotides in length, and optionally can be 18, 20, 30, 40, 50, 100 or more nucleotides. For amino acid sequences, the comparison window is at least about 15 amino acids, and can optionally be 20, 30, 40, 50, 100 or more amino acids. Those of skill in the art understand that to avoid a high similarity to a reference sequence due to inclusion of gaps in the nucleic acid or amino acid sequence, a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may permit optimal alignment of compared sequences; by the homology alignment algorithm (GAP) of Needleman and Wunsch, (1970) J. Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG™ programs (Accelrys, Inc., San Diego, Calif.)). The CLUSTAL program is well described by Higgins and Sharp (1988) Gene 73:237-44; Higgins and Sharp, (1989) CABIOS 5:151-3; Corpet, et al., (1988) Nucleic Acids Res. 16:10881-90; Huang, et al., (1992) Computer Applications in the Biosciences 8:155-65 and Pearson, et al., (1994) Meth. Mol. Biol. 24:307-31. An example of a good program to use for optimal global alignment of multiple sequences is PileUp (Feng and Doolittle, (1987) J. Mol. Evol., 25:351-60, which is similar to the method described by Higgins and Sharp, (1989) CABIOS 5:151-53 (and is hereby incorporated by reference). The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., eds., Greene Publishing and Wiley-Interscience, New York (1995).

GAP uses the algorithm of Needleman and Wunsch, (1970) J. Mol. Biol. 48:443-53, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP makes a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or more.

GAP presents one member of the family of best alignments. There may be many members of this family GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) Proc. Natl. Acad. Sci. USA 89:10915).

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar A number of low-complexity filter programs can be employed to reduce such low-complexity alignments. For example, the SEG (Wooten and Federhen, (1993) Comput. Chem. 17:149-63) and XNU (C.sub.1-ayerie and States, (1993) Comput. Chem. 17:191-201) low-complexity filters can be employed alone or in combination.

The terms "substantial identity" indicates that an inhibitory nucleic acid, polypeptide or related nucleic acid comprises a sequence with between 55-100% sequence identity to a reference sequence, with at least 55% sequence identity, or at least 60%, or at least 70%, or at least 80%, or at least 90% or at least 95% sequence identity or any percentage of range between 55-100% sequence identity relative to the reference sequence over a specified comparison window. Optimal alignment may be ascertained or conducted using the homology alignment algorithm of Needleman and Wunsch, supra.

An indication that two polypeptide sequences are substantially identical is that both polypeptides have similar activities. For example, when a polypeptide is related to TycA can catalyze the formation of aminophenylpropanoyl-CoA in a reaction that proceeds as follows.

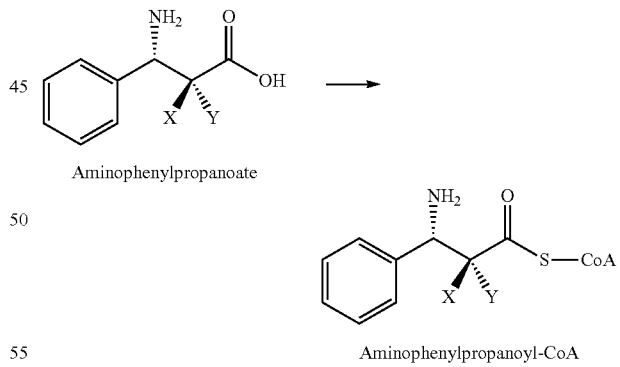

Aminophenylpropanoate

Aminophenylpropanoyl-CoA

In some embodiments, the polypeptide that is substantially identical to a TycA polypeptide with a SEQ ID NO:1, 3, 5 or 6 sequence may not have exactly the same level of activity as the TycA with a SEQ ID NO:1, 3, 5 or 6. Instead, the substantially identical polypeptide may exhibit greater or lesser levels of activity than the TycA with SEQ ID NO:1, 3, 5 or 6, as measured by assays described herein or available in the art. For example, the substantially identical polypeptide may have at least about 40%, or at least about 50%, or at least about 60%, or at least about 70%, or at least about 80%, or at least about 90%, or at least about 95%, or at least about 97%, or at least about 98%, or at least about 100%, or at least about 105%, or at least about 110%, or at least about 120%, or at least about 130%, or at least about 140%, or at least about 150%, or at least about 200% of the activity of the TycA with the SEQ ID NO:1, 3, 5 or 6 sequence, when measured by similar assay procedures.

Alternatively, substantial identity is present when a related polypeptide is immunologically reactive with antibodies raised against the TycA polypeptide (e.g., a polypeptide with SEQ ID NO:1, 3, 5, or 6 sequence). Thus, a polypeptide is substantially identical to a TycA polypeptide, for example, where the two polypeptides differ only by a conservative substitution. In addition, a polypeptide can be substantially identical to a TycA polypeptide when they differ by a non-conservative change if the epitope that the antibody recognizes is substantially identical. In some embodiments, polypeptides that are "substantially similar" share sequences as noted above except that some residue positions, which are not identical, may differ by conservative amino acid changes.

The TycA polypeptides employed in the methods of the present invention may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 N-terminal amino acid residues of a the SEQ ID NO:1, 3, 5 or 7 sequence, or of a sequence related to any of the SEQ ID NO:1, 3, 5, or 7 sequences. In some embodiments, the related TycA polypeptides may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 C-terminal amino acid residues of a the SEQ ID NO:1, 3, 5, or 7 sequence, or of a sequence related to any of the SEQ ID NO:1, 3, 5, or 7 sequences.

Synthesis of Paclitaxel and Analogs and Derivatives Thereof

The enzymes, methods and compounds generated herein can be used to make paclitaxel and it analogs and derivatives.

Taxoid compounds like paclitaxel are synthesized in certain *Taxus* plants through the 2-C-methyl-D-erythritol phosphate (MEP) pathway that generates of the isoprenes. This pathway provides an isoprenoid precursors isopentenyl diphosphate (IPP or IDP) and dimethylallyl diphosphate (DMAPP or DMADP), which can be interconverted by the enzyme isopentenyl diphosphate isomerase (IPPI) in reaction I, shown below.

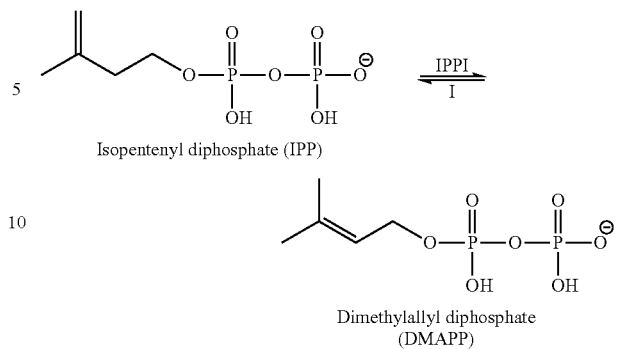

Isopentenyl diphosphate (IPP) and dimethylallyl diphosphate (DMAPP) are combined to make geranylgeranyl diphosphate (GGPP or GGDP) in reaction H by the enzyme geranylgeranyl diphosphate synthetase (GGPPS or GGDPS), as shown below.

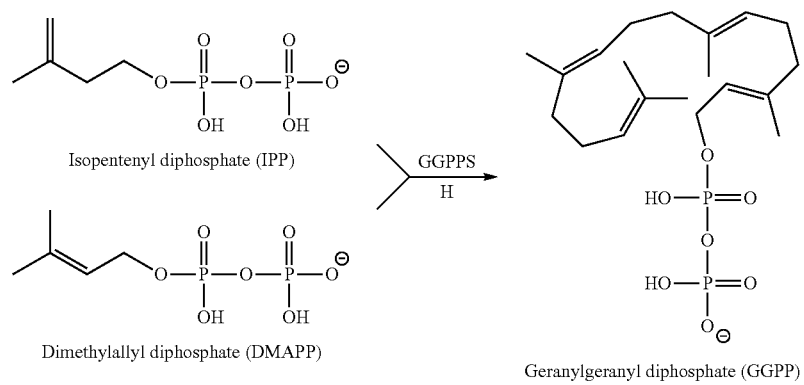

The geranylgeranyl diphosphate can then be cyclized to generate taxa-4(5),11(12)-diene ("taxadiene") by the enzyme taxadiene synthase (TS) in reaction G, shown below.

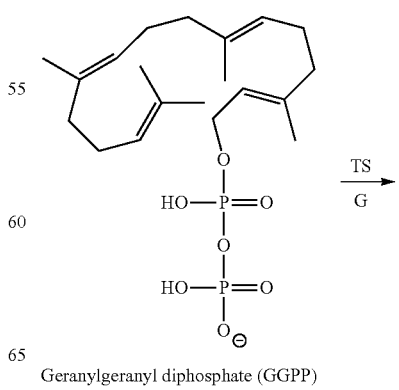

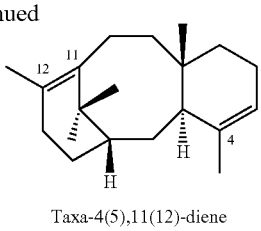

Taxa-4(5),11(12)-diene

The next step in the biosynthesis of paclitaxel and analogs or derivatives thereof involves placement of a hydroxy group at the 5 position of the taxadiene structure, with a tautomeric shift of the double bond at positions 4-5. This hydroxylation reaction (F) can be catalyzed by taxadiene 5-α-hydroxylase (T5H). Reaction F is shown below.

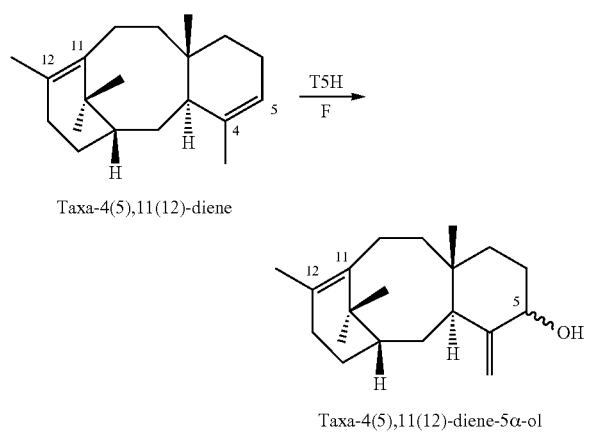

Through additional hydroxylation, acylation and cyclization reactions (E) the taxa-4(5),11(12)-diene-5α-ol is generally converted to a 2-debenzoyltaxane. These reactions (E) can be catalyzed by enzymes such as taxadiene 13-hydroxylase (T13H), taxadienol 5α-O-acetyl-transferase (TAT), taxadiene 10-hydroxylase (T10H).

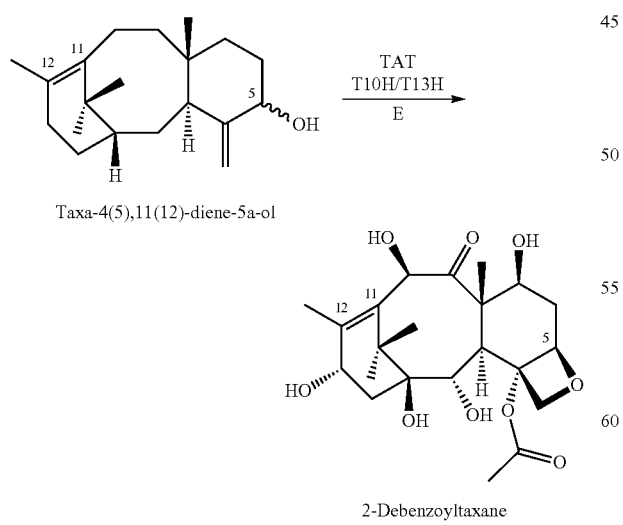

A benzoyl group is then linked to the 2-debenzoyltaxane molecule at position 2 to generate 10-deacetyl baccatin III, in reaction D, as illustrated below. An enzyme such as taxane 2α-O-benzoyltransferase (TBT) can catalyze the reaction.

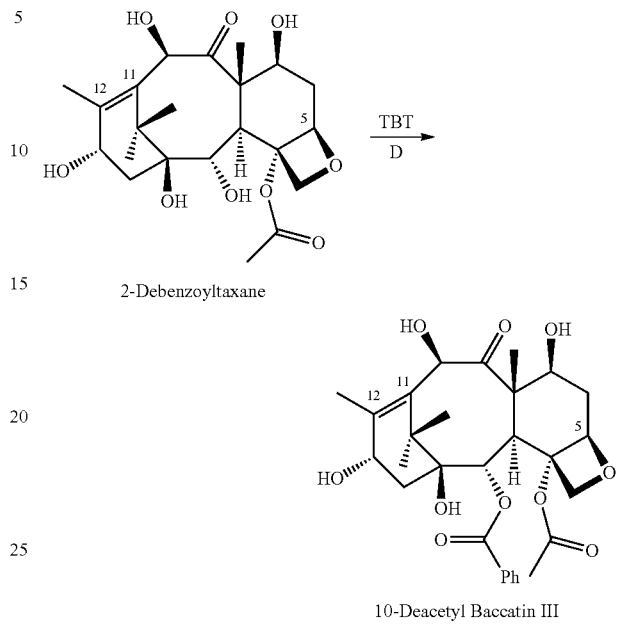

An acetyl group is then added to the molecule at position 10 to generate Baccatin III in reaction C, illustrated below. The enzyme 10-deacetylbaccatin III-10-O-acetyltransferase (DBAT) can catalyze the reaction.

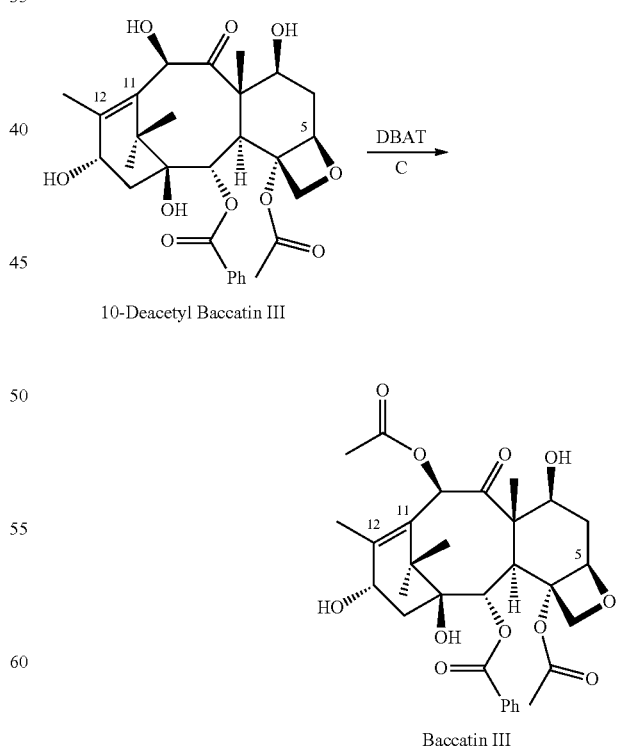

It is at this point that the aminopropanoyl-CoA generated in the following TycA reaction is employed.

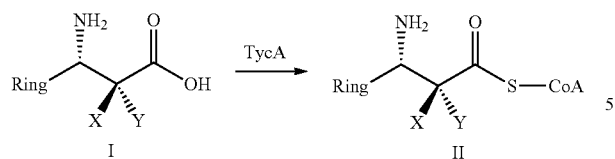

wherein:

X is hydrogen;

Y is hydrogen or OH; and

Ring is a unsubstituted or substituted (C4-C10) aryl, (C4-C9)heteroaryl, (C4-C10)cycloalkyl, or (C4-C9) heterocycloalkyl.

The aminopropanoyl-CoA (II) is reacted with Baccatin III in reaction B to thereby make 3'-N-debenzoyltaxol or an analog thereof. The enzyme can be an acyltransferase, for example, a *Taxus* acyltransferase such as baccatin III O-phenylpropanoyltransferase (BAPT). Reaction B is illustrated below.

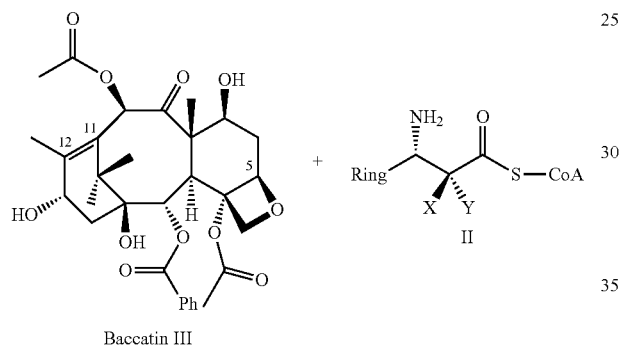

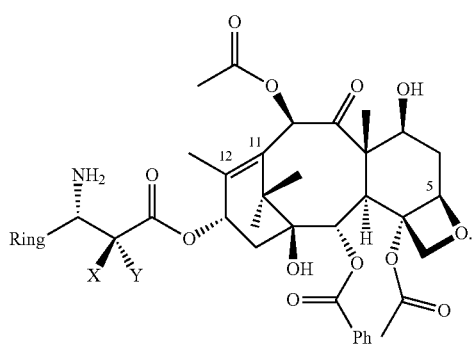

3'-N-Debenzoyltaxol or an analog or derivative thereof

Paclitaxel or an analog or derivative thereof can then be generated from 3'-N-debenzoyltaxol (or an analog or derivative) thereof via reaction A, which adds a benzoyl moiety to the amino group of the aminopropanoyl moiety. The enzyme N-debenzoyl-2'-deoxypaclitaxel: N-benzoyltransferase (NDTBT) can catalyze reaction A, shown below.

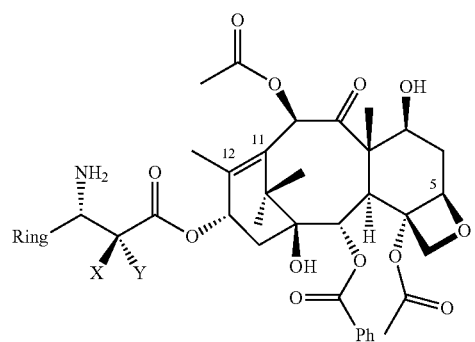

3'-N-Debenzoyltaxol or an analog or derivative thereof

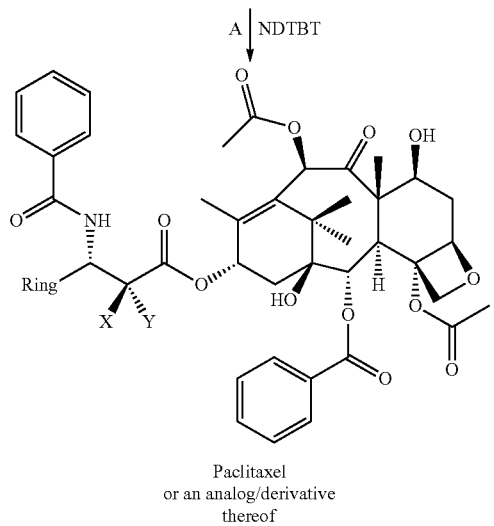

Paclitaxel or an analog/derivative thereof

Thus, paclitaxel and its analogs and derivatives can be made by a substantially enzymatic process. The various reactions and steps in a method of making paclitaxel or an analog or derivative thereof can be performed in a cell-free reaction mixture (e.g., in vitro), or in living cells.

For example, any of the enzymes, substrates, intermediates, products, analogs or derivatives thereof described herein can be immobilized or attached to a solid surface (e.g., a bead, a column matrix, a reaction wall and the like). Such immobilization or attachment can facilitate in vitro reaction to generate paclitaxel (or an analog or derivative thereof), as well as purification of the paclitaxel (or analog or derivative thereof) product. For example, substrates and/or intermediates can be attached or immobilized on a solid surface, so that reactants, side products and enzymes can be removed after each step in the synthetic process. Similarly, when the paclitaxel or an analog or derivative thereof is attached or immobilized to a solid surface, the solid surface can be washed to remove reactants, enzymes, side products and the like to facilitate purification of the desired product. Upon cleavage from the solid surface, a purified paclitaxel or an analog or derivative thereof can be obtained.

When any of the reactions or steps of the process is performed in living cells, such living cells can be cultured cells. Such cultured cells can be grown in a cell fermentation apparatus, for example, to facilitate plant cell fermentation production of paclitaxel or an analog or derivative thereof. Alternatively, such living cells can also be plant cells that are present in a plant, for example, in a plant of a *Taxus* (Yew) species. The living cells can also be transgenic cells, for example, cells recombinantly engineered to express any of the enzymes described herein.

The following non-limiting Examples illustrate aspects of the invention. Some experimental detail relating to the development of the invention is also published as Muchiri & Walker, *Taxol Biosynthesis: Tyrocidine Synthetase A Catalyzes the Production of Phenylisoserinyl CoA and Other Amino Phenylpropanoyl Thioesters*, CHEMISTRY & BIOLOGY (Jun. 22, 2012; published online Jun. 21, 2012), the contents of which are specifically incorporated herein in their entirety.

Example 1: Materials and Methods

This Example illustrates some of the materials and methods that have been used in the development of the invention.
Chemicals.

Bovine serum albumin was obtained from Thermo Scientific (Rockford, Ill.), (S)-α-phenylalanine, N-Boc-(S)-α-phenylalanine, and N-acetylcysteamine were purchased from Sigma Aldrich, N-Boc-(R/S)-β-phenylalanine was obtained from Alfa Aesar, (Ward Hill, Mass.), (R)-β-phenylalanine and N-Boc-(2R,3S)-phenylisoserine were obtained from PepTech Corp. (Burlington, Mass.), (2R,3S)-phenylisoserine was purchased from Bachem (Torrance, Calif.) and CoA was purchased from American Radiolabeled Chemicals Inc. (St. Louis, Mo.). All other reagents were obtained from Sigma-Aldrich and were used without further purification, unless noted otherwise.

Synthesis of [N-Boc-(S—((S)-α-Phenylalanyl)-N-acetyl)]cysteamine (Referred to as (N-Boc)-(S)-α-Phenylalanyl-SNAC) and [N-Boc-(S—(R/S)-β-Phenylalanyl)-N-acetyl)]cysteamine (Referred to as (N-Boc)-(R/S)-β-Phenylalanyl-SNAC)

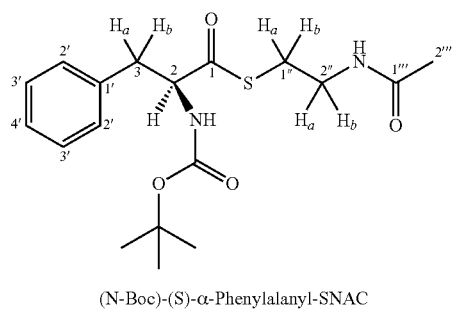

(N-Boc)-(S)-α-Phenylalanyl-SNAC

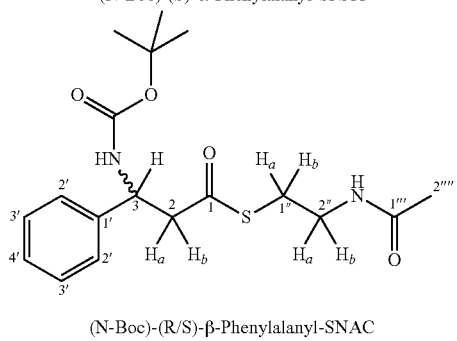

(N-Boc)-(R/S)-β-Phenylalanyl-SNAC

[S—((S)-α-Phenylalanyl)-N-acetyl]cysteamine and S—((R/S)-β-Phenylalanyl)-N-(acetyl)]cysteamine (i.e., (S)-α- and (R/S)-β-phenylalanyl-SNAC) were synthesized using a modification of the procedure reported by (Ehmann, et al. (Chem. Biol. 7, 765-772 (2000)). Generally, to N-Boc-(S)-α- or —(R/S)-β-phenylalanine (530 mg, 2 mmol) dissolved in tetrahydrofuran (15-18 mL) was added N,N'-dicyclohexylcarbodiimide (372 mg, 2 mmol), 1-hydroxybenzotriazole monohydrate (255 mg, 2 mmol), and N,N'-diisopropylethylamine (258, 8 mmol) at 24° C., and the solution was stirred. After 45 min, N-acetylcysteamine (NAC) (238 mg, 2 mmol) was added to the reaction, and the solution was stirred for ~12 h. The contents of the reaction mixture were gravity filtered (42.5 mm filter paper, Whatman, Stockton, N.J.), and the filtrate was concentrated under vacuum. The resultant residue was then dissolved in ethyl acetate (8 mL), and extracted with an equal volume of 10% aqueous $NaHCO_3$. The aqueous layer was separated, and the organic layer was extracted twice more with 10% aqueous $NaHCO_3$. The organic fraction was dried ($Na_2SO_4$), filtered, and the solvent was removed under vacuum. The resultant crude product was purified by silica gel flash chromatography (3-5% gradient of methanol in chloroform). The fractions containing the product, as judged by the thin layer chromatography ($R_f$=0.15 and 0.12 for N-Boc-α-phenylalanyl-SNAC and N-Boc-(R/S)-β-phenylalanyl-SNAC, respectively) were combined separately and concentrated to afford the following products:

N-Boc-α-phenylalanyl-SNAC (552 mg, 75% isolated yield). $^1$H NMR (500 MHz, DMSO-$d_6$) δ: 1.32 (s, 9H, methyl-H of Boc), 1.80 (s, 3H, H-2'''), 2.79 (dd, J=13.7, 10.0 Hz, 1H, $H_b$-3), 2.87 (t, J=6.0 Hz, 2H, $H_a$-1", $H_b$-1"), 3.05 (dd, J=13.9, 5.0 Hz, 1H, $H_a$-3), 3.15 (q, J=6.0, 2H, $H_a$-2", $H_b$-2"), 4.23 (dd, J=7.2, 5.0 Hz, 1H, H-2), 7.20-7.27 (m, 5H, H-2', H-3', H-4'), 7.67 (d, J=8.30 Hz, 1H, OC(O)NH); 8.04 (t, J=5.0 Hz, 1H, C(O)NH). $^{13}$C NMR (125 MHz, DMSO-$d_6$) δ: 202.33 (C-1), 169.91 (C-1'''), 155.97 (C=O of Boc), 138.20 (C-1'), 129.78-127.10 (C-2', C-3', C-4'), 79.34 (tert-C of Boc), 62.97 (C-2), 42.85 (C-3), 38.79 (C-2"), 28.83 (methyl-C of Boc), 24.20 (C-1"), 23.22 (C-2''').

N-Boc-(R/S)-β-phenylalanyl-SNAC (487 mg, 66% isolated yield). $^1$H NMR (500 MHz, DMSO-$d_6$) δ: 1.74 (s, 9H, methyl-H of Boc), 2.07 (s, 3H, $H_a$-2'''), 2.84 (ddd, J=12.0, 6.0, 6.0 Hz, 2H, $H_a$-1", $H_b$-1"), 3.08 (q, J=6.0 Hz, 2H, $H_a$-2", $H_b$-2"), 3.29 (dd, J=15.0, 9.0 Hz, 1H, $H_a$-2), 3.40 (dd, J=15.0, 5.5 Hz, 2H, $H_b$-2), 4.64 (m, 1H, H-3), 7.37-7.51 (m, 5H, H-2'a, H-3'a, H-4'a), 8.02 (t, J=5.5 Hz, 1H, C(O)NH); 8.63 (bs, 1H, OC(O)NH). $^{13}$C NMR (125 MHz, DMSO-$d_6$) δ: 196.49 (C-1) 169.89 (C-1'''), 155.35 (C=O of Boc), 141.0 (C-1'), 128.99-127.04 (C-2', C-3', C-4'), 78.67 (tert-C of Boc), 51.93 (C-3), 50.72 (C-2), 38.86 (C-2"), 28.89 (methyl-C of Boc), 28.68 (C-1"), 23.22 (C-2''').

Synthesis of [(S—((S)-α-Phenylalanyl)-N-acetyl)]cysteamine and [(S—((S)—(R/S)-β-Phenylalanyl)-N-acetyl)]cysteamine

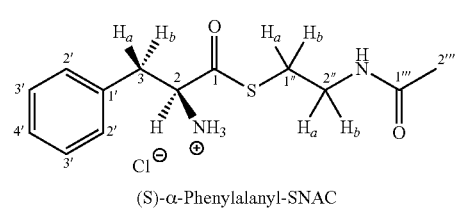

(S)-α-Phenylalanyl-SNAC

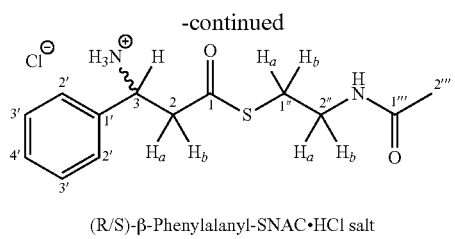

(R/S)-β-Phenylalanyl-SNAC·HCl salt

To remove the Boc groups, N-Boc-(S)-α-phenylalanyl-SNAC and N-Boc-(R/S)-β-phenylalanyl-SNAC were separately dissolved in dichloromethane (4 mL), and trifluoroacetic acid was added dropwise over 4 h at 0° C. The reaction progress was monitored by normal-phase thin layer chromatography (5% methanol in chloroform). Excess trifluoroacetic acid was removed prior to isolating the (S)-α-phenylalanyl-SNAC by concentrating the reaction volume to 2 mL under vacuum, diluting 2-fold in dichloromethane, and then concentrating to 1-2 mL. This dilution/concentration cycle was repeated three times, after which, the solvent was removed completely. To the residue containing (S)-α-phenylalanyl-SNAC was added ethyl acetate and dilute aqueous NaOH at 0° C. to partition the (S)-α-phenylalanyl-SNAC and aqueous soluble contaminants, respectively. The organic layer was decanted and then removed under vacuum. Water (2 mL) was added to the remaining residue to which 1 M HCl (2 mL) was added at 0° C. Ethyl acetate was added (2×2 mL) to extract any remaining t-butanol and SNAC, and the organic layer was decanted. The water fraction was lyophilized to yield (S)-α-phenylalanyl-SNAC as the hydrochloride salt isolated at ~31% yield (90 mg) based on the N-Boc-protected starting material. $^1$H NMR (500 MHz, DMSO-$d_6$) δ: 1.78 (s, 3H, H-2'''), 2.69 (dd, J=13.6, 10.0 Hz, 1H, $H_b$-3), 2.80 (t, J=6.0 Hz, 2H, $H_a$-1'', $H_b$-1''), 2.96 (dd, J=13.6, 5.0 Hz, 1H, $H_a$-3), 3.12 (q, J=6.0 Hz, 2H, $H_a$-2'', $H_b$-2''), 3.62 (dd, J=8.7, 5.00 Hz, 1H, H-2), 7.17-7.29 (m, 5H, H-2', H-3', H-4'), 8.02 (t, J=5.0 Hz, 1H, C(O)NH). $^{13}$C NMR (125 MHz, DMSO-$d_6$) δ: 204.1 (C-1), 168.2 (C-1'''), 136.8 (C-1'), 128.3-125.30 (C-2', C-3', C-4'), 61.74 (C-2), 39.51 (C-3), 37.22 (C-2''), 26.64 (C-1''), 21.53 (C-2'''). The exact mass was determined in the positive ion mode on a Quadrupole Time-of-Flight Tandem Mass Spectrometer: observed m/z=267.1164; calculated m/z=267.1167 for $C_{13}H_{19}N_2O_2S$.

After deprotection of (N-Boc)-(R/S)-β-phenylalanyl-SNAC, excess trifluoroacetic acid was removed prior to isolating the product, as described above, except the residue was dissolved in 1 M HCl (2 mL, at 0° C.) to exchange the trifluoroacetate salt for the hydrochloride salt of the product. The sample was lyophilized to dryness, resulting in the hydrochloride salt of (R/S)-β-phenylalanyl-SNAC (48 mg, ~88.1% yield). $^1$H NMR (500 MHz, DMSO-$d_6$) δ: 1.74 (s, 3H, H-2'''), 2.84 (ddd, J=12.0, 6.0, 6.0 Hz, 2H, $H_a$-1'', $H_b$-1''), 3.08 (q, J=6.0 Hz, 2H, $H_a$-2'', $H_b$-2''), 3.31 (dd, J=15.0, 9.0 Hz, 1H, $H_a$-2), 3.45 (dd, J=15.0, 5.5 Hz, 1H, $H_b$-2), 4.63 (m, 1H, H-3), 7.35-7.60 (m, 5H, 3H, H-2', H-3', H-4'), 8.06 (t, J=5.5 Hz, 1H, H—C(O)NH), 8.73 (bs, 1H, $H_3N^+$). $^{13}$C NMR (125 MHz, DMSO-$d_6$) δ: 204.1 (C-1), 168.2 (C-1'''), 136.8 (C-1'), 128.3-125.30 (C-2', C-3', C-4'), 51.64 (C-3), 48.07 (C-2), 38.57 (C-2''), 28.92 (C-1''), 23.18 (C-2'''). The exact mass was determined in the positive ion mode on a Quadrupole Time-of-Flight Tandem Mass Spectrometer: observed m/z=267.1173; calculated m/z=267.1167 for $C_{13}H_{19}N_2O_2S$.

Synthesis of [(S-((2R,3S)-Phenylisoserinyl-N-acetyl)cysteamine

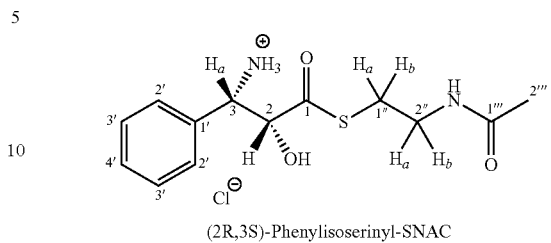

(2R,3S)-Phenylisoserinyl-SNAC

N-Boc-(2S,3R)-Phenylisoserinyl SNAC was synthesized according to the procedure described for the α- and β-phenylalanyl SNAC thioesters, with slight modifications. Briefly, to N-Boc-(2S,3R)-phenylisoserine (100 mg, 0.36 mmol) dissolved in tetrahydrofuran (~6 mL) were added N,N'-dicyclohexylcarbodiimide (74.3 mg, 0.36 mmol), 1-hydroxybenzotriazole monohydrate (48.6 mg, 0.36 mmol), and N,N'-diisopropylethylamine (23.3 mg, 0.72 mmol), and the solution was stirred at 24° C. After 45 min, NAC (85.6 mg, 0.72 mmol) was added to the reaction, and the solution was stirred for ~12 h. The reaction work up and purification were done as described above for the α- and β-amino acid analogs, resulting in residue (~40 mg) containing crude N-Boc-(2S,3R)-phenylisoserinyl, which was deprotected without further purification. To the crude mixture containing N-Boc-(2S,3R)-phenylisoserinyl dissolved in dichloromethane (4 mL) was added (dropwise) trifluoroacetic acid over 3 h at 0° C. The reaction progress was monitored by normal-phase thin layer chromatography (5% methanol in chloroform). The work up was similar to the procedure described for (R/S)-β-phenylalanyl-SNAC resulting in the hydrochloride salt of (2S,3R)-phenylisoserinyl SNAC (20 mg, ~24% isolated yield based on N-Boc-(2S, 3R)-phenylisoserine). $^1$H NMR (500 MHz, DMSO-$d_6$) δ: 1.79 (s, 3H, H-2'''), 2.81 (m, 2H, $H_a$-1'', $H_b$-1''), 3.15 (m, 2H, $H_a$-2'', $H_b$-2''), 4.39 (d, J=5.0 Hz, 1H, H-2), 4.45 (m, 1H, H-3), 7.40-7.47 (m, 5H, H-2', H-3', H-4'), 8.09 (t, J=5.6 Hz, 1H, C(O)NH), 8.52 (brd, J=5.0 Hz 1H, $H_3N^+$). $^{13}$C NMR (125 MHz, DMSO-$d_6$) δ: 202.06 (C-1), 170.14 (C-1'''), 135.25 (C-1'), 129.51-128.77 (C-2', C-3', C-4'), 78.24 (C-3), 57.09 (C-2), 38.38 (C-2''), 28.33 (C-1''), 23.24 (C-2'''). The exact mass was determined in the positive ion mode on a Quadrupole Time-of-Flight Tandem Mass Spectrometer: observed m/z=283.1108; calculated m/z=283.1116 for $C_{13}H_{19}N_2O_3S$.

Expression of Wild-Type TycA cDNA.

A cDNA clone of wild-type tyrocidine synthetase A (tycA) from *Brevibacillus brevis* was obtained as a gift from Florian Hollfelder (University of Cambridge, UK). Cloned tycA cDNA was inserted into a pSU18 vector, and the plasmid was designated pSU18-PheATE-His, encoding expression for a C-terminal $His_6$-epitope. The plasmid was used to transform *Escherichia coli* BL21 (DE3) grown in 2×YT medium (100 mL), containing Bacto Tryptone (1.6 g), Bacto Yeast Extract (1.0 g), NaCl (0.5 g), and chloramphenicol (20 mg·mL$^{-1}$) at 37° C. for 12 h. A 10-mL aliquot of the seed culture was used to inoculate 2×YT medium (5×1 L). The bacteria were grown at 37° C. to $OD_{600}$~0.6, at which time isopropyl-D-thiogalactopyranoside was added to a final concentration of 0.5 mM, and the culture was grown for 4 h at 30° C. The cells were pelleted by centrifugation (30 mM, 4000 g) at 4° C., resuspended in Binding Buffer (20 mM Tris-HCl buffer containing 0.5 M NaCl and 5 mM imidazole at pH 7.8), lysed by sonication (Misonix XL 2020 sonicator, Misonix, Inc. Farmingdale, N.Y.), and then centrifuged at 15,000 g for 0.5 h. The supernatant was decanted and centrifuged at 149,000 g for 2 h to remove cell wall debris and light membranes.

Construction and Expression of the S563A TycA Mutant.

A S563A amino acid mutation was incorporated into the wild-type TycA clone by site-directed mutagenesis. The oligonucleotide primer pair used to incorporate the point mutation (underlined) were as follows: Forward primer S563A—For: 5'-TTA CTC GCT CGG CGG AGA T<u>GCG</u>AT CCA AGC GAT CCA GGT CG-3' (SEQ ID NO:8); Reverse primer S563A-Rev: 5'-CGA CCT GGA TCG CTT GGA T <u>CGC</u>AT CTC CGC CGA GCG AGT AA-3' (SEQ ID NO:9). The correct synthesis of the mutant cDNA was verified by DNA sequencing. The resultant plasmid encoding a C-terminal His-tag (designated pSU18-S563A-PheATE-His) was used to transform $E.\ coli$ BL21(DE3) cells. A 10-mL culture of $E.\ coli$ transformed with the PSU18 vector was grown in 2×YT medium at 37° C. with chloramphenicol (20 mg·mL$^{-1}$) selection for 12 h. The 10-mL inoculum was transferred to a new batch of 2×YT medium (1 L), as described previously for the expression of the wild-type TycA clone. The bacteria were grown at large-scale at 37° C. to $OD_{600}$~0.6, and the cDNA expression was induced by isopropyl-D-thiogalactopyranoside, and the culture was grown for 4 h at 30° C. The cells were pelleted by centrifugation (30 min, 4000 g) at 4° C., resuspended in Binding Buffer, lysed by sonication, and the corresponding soluble protein fraction was clarified by centrifugation as described earlier to remove cell-wall debris and light membranes.

Purification and Characterization of TycA and the TycA-S563A Mutant.

Crude soluble enzyme was separately isolated from bacteria expressing the wild-type tycA or tycA-5563A. Each fraction contained ~15 mg total protein as estimated by the Bradford protein assay (Bradford, M. M. *Anal. Biochem.* 1976, 72, 248-254). These fractions were independently loaded onto a nickel-nitrilotriacetic acid affinity column (Qiagen, Valencia, Calif.) and eluted according to the protocol described by the manufacturer. The column was washed with increasing concentration of imidazole (20-250 mM) in Binding Buffer. SDS-PAGE slabs were loaded with aliquots from each fraction that eluted off the nickel-affinity column and stained with Coomassie Blue. Fractions that contained >95% pure protein corresponding to a molecular weight consistent with that of TycA and TycA-S563A at 123 kDa were combined. The enzymes were eluted in ~50 mM imidazole (100 mL) and were separately loaded into a Centriprep size-selective (100,000 MWCO) centrifugal filtration unit (Millipore, Billerica, Mass.). The protein solutions were concentrated to 1 mL, and the buffer was exchanged with the Assay Buffer (50 mM HEPES containing 100 mM NaCl and 1 mM EDTA at pH 8.0) over several dilution/concentration cycles. The final purity of the enzyme was estimated by SDS-PAGE with Coomassie Blue staining. The final protein concentration was determined by Beer's Law and measuring the absorbance of the protein solution at $A_{280}$ on a NanoDrop ND1000 Spectrophotometer (Thermo Scientific, Wilmington, Del.). The extinction coefficient, $\varepsilon_{280}$, employed was 142685 M$^{-1}$ cm$^{-1}$ (Villiers & Hollfelder, *Chembiochem,* 10: 671-682 (2009)) and the molecular weight of TycA and TycA-S563A were 122675.9 g·mol$^{-1}$ and 122,675.9 g·mol$^{-1}$, respectively, consistent with the theoretical value of 123 kDa. The purified protein was stored at 5 mg/mL at −80° C. The protein sequence of the isolated TycA and TycA-S563A recombinant proteins was confirmed by electrospray ionization tandem mass spectrometry analysis.

Assessing TycA and TycA-S563A as Ligases for Catalysis of α- and β-Amino Phenylpropanoyl-Coenzyme A Thioesters.

Substrates (S)-α-phenylalanine, (R)-β-phenylalanine, and (2R,3S)-phenylisoserine (each at 1 mM) were separately incubated at 31° C. in single stopped-time (1 h) reactions containing 100 mM HEPES (pH 8.0), ATP (1 mM), MgCl$_2$ (3 mM), CoA (1 mM), and TycA or TycA-S563A (100 µg). Various control reactions were carried out in parallel under the same conditions used for assays containing enzyme, where TycA, TycA-S563A, ATP, or CoA was omitted from the assay. The reactions were quenched by acidification to a pH of about 2 (using 10% formic acid in distilled water) and lyophilized to dryness. The resultant samples were separately dissolved in aqueous 0.01 M HCl (100 µL) and analyzed using a Quattro-Premier Electrospray Tandem Mass Spectrometer coupled with Acquity® UPLC system (LC-QP/ESI-MS/MS) fitted with a C18 Ascentis Express column (2.5×50 mm, 2.7 µm) at 30° C. An aliquot (10 µL) of each sample was loaded onto the column and the analytes were eluted with a solvent gradient of 0-15% of acetonitrile (Solvent A) in 0.1% formic acid in distilled water (Solvent B) at a flow rate of 0.2 mL/min. The effluent from the column was directed to the mass spectrometer set to negative ion mode with a scan range of m/z 200-1000 atomic mass units. Authentic phenylalanyl CoA was used as a model to identify the diagnostic ion transition ([M−H]$^-$→m/z 408) of the three acyl CoA products.

Kinetic Analysis of the CoA Ligase Reaction Catalyzed by TycA and TycA-S563A.

After identifying productive substrates for TycA and TycA-S563A in the screen for CoA ligase function, substrates (S)-α-phenylalanine, (R)-β-phenylalanine, and (2R, 3S)-phenylisoserine (each at 1 mM) were separately incubated (at 31° C.) in 100 µL reactions containing 100 mM HEPES (pH 8.0), ATP (1 mM), MgCl$_2$ (3 mM), CoA (1 mM), and TycA or TycA-S563A (50 µg) to establish steady-state conditions with respect to protein concentration and time. Under steady-state conditions, (S)-α-phenylalanine, (R)-β-phenylalanine, and (2R,3S)-phenylisoserine at 5, 10, 20, 40, 80, 160, 250, 500, 1000 and 2000 µM were separately incubated with TycA or TycA-S563A (20 µg) for 30 min. At the end of each reaction, and prior to mass spectrometry analysis, acetyl CoA (1 µM) was added as the internal standard to each sample to correct for variations of the analyte. The products of the enzyme-catalyzed reaction were quantified by a liquid chromatography multiple reaction monitoring (LC-ESI-MRM) mass spectrometry technique (Anderson & Hunter, *Mol. Cell. Proteomics* 5: 573-588 (2006)) on the Quattro-Premier Electro-Spray Mass Spectrometer coupled with Acquity® UPLC system fitted with a C18 Ascentis Express column (2.5×50 mm, 2.7 µm) at 30° C. An aliquot (5 µL) of each sample was loaded onto the column and the analytes were eluted with a solvent gradient of acetonitrile (Solvent A) in 0.05% triethylamine in distilled water (Solvent B). Elution was held at 2.5% Solvent A for 3.17 min, increased to 100% Solvent A over 5 sec with a 2-min hold, and then returned to 2.5% Solvent A over 5 sec with a 50-sec hold. The flow rate employed was 0.4 mL/min. The effluent from the chromatography column was directed to the mass spectrometer where the first quadrupole mass analyzer (in negative ion mode) was set to select for the molecular ion of a biosynthesized acyl CoA product. The selected ion was then directed to a collision gas chamber where the collision energy was optimized to maximize the abundance of a single signature fragment ion (m/z 408, characteristic of acyl CoA thioesters) resolved in the second quadrupole mass analyzer by the MRM method. The peak area under the curve of fragment ion m/z 408 for each biosynthetic phenylpropionyl CoA thioester was converted to concentration by comparing the peak area of the same ion produced by authentic CoA (at 0.05, 0.1, 0.2, 0.4, 0.8, 1.6, 3.2, 6.4, 12.5, 25, 50, 100 µM) using linear regression analysis. The initial velocity ($v_o$) of (S)-α-phenylalanyl-CoA, (R)-β-phenylalanyl-CoA and (2R,3S)-phenylisoserinyl-CoA made in separate assays was plotted against substrate concentration and fit by non-linear regression to the Michaelis-Menten equation ($R^2$ was typically between 0.90 and 0.99) to calculate the Michaelis parameters ($K_M$ and $k_{cat}$).

The $K_M$ values of TycA and TycA-S563A for CoA were assessed by incubating each enzyme separately with (S)-α-phenylalanine (1 mM), $MgCl_2$ (3 mM), ATP (1 mM), and CoA at 0.05, 0.1, 0.2, 0.4, 0.8, 1.6, 3.2, 6.4, 12.8 and 25.6 mM at 31° C. for 20 min. At the end of each reaction and prior to mass spectrometry analysis, acetyl CoA (1 µM) was added as the internal standard to each sample to correct for variations of the analyte. The products of the enzyme-catalyzed reaction were quantified by LC-ESI-MRM, and the monitored fragment ion (m/z 408) derived from the CoA moiety of the thioester analytes in the effluent was quantified identically to the procedure described earlier herein. The initial velocity ($v_o$) production of (S)-α-phenylalanyl CoA made in separate assays was plotted against substrate concentration and fit by non-linear regression to the Michaelis-Menten equation ($R^2$ was typically between 0.92 and 0.98) to calculate the Michaelis constant ($K_M$).

N-Acetylcysteamine, Phenylalanines, and Phenylisoserine Substrates Used to Screen TycA and TycA-S563A for Activity.

Similar experiments were performed using methods described above for the CoA ligase screen, except N-acetylcysteamine (5 mM, 'NAC') was used in place of CoA with the substrates (S)-α-phenylalanine, (R)-β-phenylalanine and (2R,3S)-phenylisoserine in different 0.1 mL assays. In general, the enzyme assays for this study contained 100 mM HEPES (pH 8.0), phenylpropanoate (1 mM), ATP (1 mM), $MgCl_2$ (3 mM), N-acetylcysteamine (5 mM), and TycA or TycA-S563A (100 µg), and were incubated at 31° C. for 1 h. Various control reactions were carried out in parallel under the same conditions used for the enzyme assay, where either TycA, TycA-S563A, ATP, or N-acetylcysteamine was omitted from the assays. The reactions were quenched by acidification to a pH of about 2 (with 6 M HCl) and lyophilized to dryness. The resultant residues were separately dissolved in aqueous 0.01 M HCl (100 µL) and analyzed using a Quadrupole Time-of-Flight Tandem Mass Spectrometer coupled with 2795 HPLC system fitted with a reverse-phase Halo C18 column (5 cm×2.1 mm) (reverse-phase LC-QToF-MS/MS). The mass analyzer was set to positive ion mode, with a scan range of m/z 0-500 atomic mass units. An aliquot (10 µL) of each sample was loaded onto the column (at 30° C.) and the analytes were eluted with a solvent gradient of 0-15% of acetonitrile (Solvent A) in 0.1% formic acid in distilled water (Solvent B) at a flow rate of 0.2 mL/min.

Kinetic Analysis of the N-acetylcysteamine Ligase Reaction Catalyzed by TycA or TycA-S563A.

Substrates (S)-α-phenylalanine, (R)-β-phenylalanine, and (2R,3S)-phenylisoserine (each at 1 mM) were separately incubated with TycA or TycA-S563A (20 µg) in the presence of N-acetylcysteamine (NAC; 1 mM), ATP (1 mM), and $Mg^{2+}$ (3 mM) to establish steady-state conditions with respect to protein concentration and time at 31° C. Under steady-state conditions, either (S)-phenylalanine, (R)-β-phenylalanine, or (2R,3S)-phenylisoserine at 5, 10, 20, 40, 80, 160, 250, 500, 1000 and 2000 µM was separately incubated with TycA or TycA-S563A (20 µg), ATP (1 mM), $Mg^{2+}$ (3 mM), and N-acetylcysteamine (1 mM, 'NAC') in duplicate, single stopped-time (20 mM) 100 µL assays. The reactions were quenched by acidification to a pH of about 2 (10% formic acid in distilled water). (N-Boc)-α-phenylalanyl-SNAC (1 µM) was added as an internal standard when (S)-α-phenylalanine or (2,3)-phenylisoserine was used as the substrate; alternatively, (N-Boc)-β-phenylalanyl-SNAC (1 µM) was added as an internal standard when (R)-β-phenylalanine was used as the substrate (the synthesis is described below). The samples were analyzed on a Quattro-Premier Electro-Spray Mass Spectrometer coupled with Acquity® UPLC system fitted with a C18 Ascentis Express column (2.5×50 mm, 2.7 µm) at 30° C. An aliquot (5 µL) of each sample was loaded onto the column and the analytes were eluted with a solvent gradient of (Solvent A) in 0.05% triethylamine in distilled water (Solvent B) (held at 2.5% Solvent A for 3.17 mM, increased to 100% A over 5 sec with a 2-min hold, and then returned to 2.5% Solvent A over 5 sec with a 50-sec hold) at a flow rate of 0.4 mL/min. In brief, the effluent from the chromatography column was directed to the Quattro Premier ESI mass spectrometer, in MRM scan mode, to quantify the biosynthetic acyl SNAC products. The transition ions derived from the corresponding molecular ions were m/z 120.06, 131.10 and 105.95 for (S)-α-phenylalanyl-SNAC, (R)-β-phenylalanyl-SNAC and (2R,3S)-phenylisoserinyl-SNAC, respectively. A standard curve was used to convert the peak area under the curve of the monitored fragment ion to concentration for each biosynthetic phenylpropionyl SNAC.

Authentic (S)-α-phenylalanyl, (R/S)-β-phenylalanyl- and (2R,3S)-phenylisoserinyl-SNAC were used to construct the standard curves by correlating the peak area under the curve of the monitored ion to concentration of the standard (at 0.16, 0.32, 0.64, 1.3, 2.5, 5, 10, 20, 40, 80, 160 and 320 µM) using linear regression analysis. The initial velocity ($v_o$) production of (S)-α-phenylalanyl, (R/S)-β-phenylalanyl- and (2R,3S)-phenylisoserinyl-SNAC was plotted against substrate concentration and fit by non-linear regression to the Michaelis-Menten equation ($R^2$ was typically 0.99) to calculate the Michaelis parameters ($K_M$ and $k_{cat}$).

The $K_M$ values of TycA and TycA-S563A for N-acetylcysteamine (NAC) was assessed by incubating each enzyme separately with (S)-α-phenylalanine (1 mM), $MgCl_2$ (3 mM), ATP (1 mM), and N-acetylcysteamine at 5, 10, 20, 40, 80, 160, 250, 500, 1000 and 2000 µM at 31° C. for 20 min. The reactions were quenched by acidification to a pH of about 2 (10% formic acid in distilled water), and an internal standard, (N-Boc)-α-phenylalanyl-SNAC (1 µM), was added to each sample to correct for variations of the analyte. The [S-(acyl)-N-(acetyl)]cysteamine (SNAC) thioester products of the enzyme-catalyzed reaction were quantified by a liquid chromatography multiple reaction monitoring (MRM) mass spectrometry technique, and the monitored fragment ion (m/z 120) derived from the SNAC moiety of thioester analyte in the effluent was quantified identically to the procedure described earlier. The initial velocity ($v_o$) production of (R)-α-phenylalanyl-SNAC made in separate assays was plotted against substrate concentration and fit by non-linear regression to the Michaelis-Menten equation ($R^2$ was typically between 0.97 and 0.99) to calculate the Michaelis constant ($K_M$) and $k_{cat}$.

Kinetics of the AMP Ligase Reaction.

Each (S)-α-phenylalanine, (R)-β-phenylalanine, and (2R,3S)-phenylisoserine substrate (at 1 mM) was separately incubated (31° C.) in 100-μL reactions containing 100 mM HEPES (pH 8.0), ATP (1 mM), $MgCl_2$ (3 mM) and TycA or TycA-S563A (20 μg in 0.1-mL assays) to establish steady-state conditions relative to protein concentration and time. Under steady-state conditions, each (S)-α-phenylalanine, (R)-β-phenylalanine, and (2R,3S)-phenylisoserine substrate, at ten concentration intervals from 5 to 1000 μM (in duplicate), was separately incubated with TycA or TycA-S563A for 1 min at 31° C. The reactions were acid-quenched (pH 3 with 10% formic acid), and the biosynthetic products were quantified by LC-ESI-MRM mass spectrometry (Anderson and Hunter, 2006) on the LC-QP/ESI-MS/MS fitted with a C18 Ascentis Express column (2.5×50 mm, 2.7 μm) at 30° C. An aliquot (5 μL) of each sample was loaded onto the column and the analytes were eluted with the CoA-Elution Gradient (see procedures described above). The effluent from the chromatography column was directed to the mass spectrometer where the first quadrupole mass analyzer (in negative ion mode) was set to select for the molecular ion of a biosynthesized (S)-α-phenylalanine-AMP, (R)-β-phenylalanine-AMP, and (2R,3S)-phenylisoserine-AMP. The selected ion was directed to the next quadrupole where the collision energy was optimized to maximize the abundance of a single signature fragment ion (m/z 134, the adenine fragment of the adenosine moiety) in negative ion mode. This ion was resolved in the second quadrupole mass analyzer by MRM of the adenine transition ion fragment (m/z 134). The peak area of ion m/z 134 for each biosynthetic (S)-α-phenylalanine-AMP, (R)-β-phenylalanine-AMP, and (2R,3S)-phenylisoserine-AMP was converted to concentration units using linear regression of a dilution series of authentic adenosine (at six intervals from 0.01 to 20 μM) plotted against the corresponding ion abundance (m/z 134, in negative ion mode). The initial velocity ($v_o$) of (S)-α-phenylalanine-AMP, (R)-β-phenylalanine-AMP, and (2R,3S)-phenylisoserine-AMP production was used to calculate $K_M$ and $k_{cat}$ according to the Michaelis-Menten equation ($R^2$ was typically between 0.95 and 0.99).

Example 2: Enzymatic Synthesis of Paclitaxel Intermediate

This Example illustrates that tyrocidine synthetase A (TycA) is an adenylating domain of a nonribosomal peptide synthetase (NRPS) tyrocidine synthetase that can produce amino phenylalanyl CoA and amino phenylisoserinyl CoA thioesters useful for making the antineoplastic drug paclitaxel and its analogs.

Expression and Purification of the ATE Tridomain of Wild-Type and Mutant tycA.

To test whether the TycA tridomain module is a potential CoA ligase, the wild-type tycA cDNA encoding the A-, T-, and E-domains was subcloned into a pSU18 vector and heterologously expressed as a $His_6$-fusion in *Escherichia coli* BL21(DE3). *E. coli* BL21 encodes the 4'-Phosphopantetheine transferase enzyme within its genome that can post-translationally couple 4'-phosphopantetheine (Ppant) to certain serine residues of various polypeptides (Jeong, et al., J. Mol. Biol. 394, 644-652 (2009)). Therefore, Ser563 of TycA was changed to Ala563 (TycA-S563A) to prevent Ppant coupling at Ser563 of the T-domain and thus stall the reaction progress of TycA-S563A at the acyl-adenylate intermediate. The T-domain mutant TycA-S563A was also subcloned into a pSU18 vector and heterologously expressed as a His6-fusion in *Escherichia coli* BL21(DE3). The isolated soluble enzymes were Ni-affinity purified to about 95% purity based upon SDS-PAGE analysis with Coomassie Blue staining, and the apparent molecular mass (123 kDa) was consistent with the theoretical value. Wild-type TycA and the S563A mutant (TycAS563A) polypeptides were separately expressed, isolated, and purified from a 5 liter bacterial culture, resulting in about 15 mg of each protein. These wild-type TycA and S563A mutant (TycAS563A) polypeptides were used for activity assays.

Assessment of TycA and TycA-S563A Thiol Ligase Activities.

(S)-α-Phenylalanine, (R)-β-phenylalanine, and (2R,3S)-phenylisoserine were separately added to reaction mixtures containing overexpressed TycA or TycA-S563A along with ATP, $MgCl_2$, and CoA or NAC. The product mixtures were screened directly by LC-ESI-mass spectrometry in scan mode. The ion profiles in ESI-MS in negative ion mode (without collision induced ionization) contained a diagnostic, negative molecular ion [M–H]$^-$ consistent with the value calculated for each putative α-phenylalanyl-CoA (m/z 913, eluting at 2.67 min), β-phenylalanyl-CoA (m/z 913, eluting at 2.47 min), as well as (2R,3S)-phenylisoserinyl-CoA (m/z 929, eluting at 2.26 min) (see FIGS. 1-3).

To confirm the structures of the phenylpropanoid CoA thioesters, the molecular ions were further evaluated by MS/MS analysis (collision-induced dissociation of the [M–H]$^-$ ion) in negative ion mode. Collision-induced dissociation of the molecular ions confirmed the identity of each CoA thioester. Control assays lacking (S)-α-Phenylalanine, (R)-β-phenylalanine, (2R,3S)-phenylisoserine, ATP, or CoA from the appropriate enzyme assay mixture did not yield a detectable [M–H]$^-$ ion that matched any of the corresponding (S)-α-Phenylalanine, (R)-β-phenylalanine, and (2R,3S)-phenylisoserine CoAs (FIGS. 4-5). The sample incubated with (S)-α-phenylalanine had an m/z 913 ([M–H]$^-$) ion that was consistent with (S)-α-phenylalanyl CoA and fragment ions at 895 (m/z 913 ion-$H_2O$), 833 (m/z 913 ion-$HPO_3$), 566 (m/z 833 ion-adenosine), 426 (adenosine (monohydrogen 3',5'-diphosphate)), 408 (m/z 426 ion-$H_2O$), and 327 (m/z 426 ion-$H_2O$—$HPO_3$) that were consistent with TycA-mediated production of α-phenylalanyl CoA. The sample incubated with (R)-β-phenylalanine contained an m/z 913 ([M–H]$^-$) ion was consistent with β-phenylalanyl-CoA and that fragmented ions at m/z 426 (adenosine (monohydrogen 3',5'-diphosphate)), and 408 (m/z 426 ion-$H_2O$). After (2R,3S)-phenylisoserine was incubated with the enzymes, the resultant sample contained an m/z 929 ([M–H]$^-$) ion was consistent with (2R,3S)-phenylisoserine-CoA and fragmentation ions m/z 582 (m/z 929 ion-adenosine), 426 (adenosine (monohydrogen 3',5'-diphosphate)), and 408 (m/z 426 ion-$H_2O$). Minor fragments ions m/z 842 and 824 were probably derived from the phenylisoserinyl side chain (bearing a hydroxyl group at C2) attached to an intact CoA, all consistent with phenylisoserinyl CoA. Control assays lacking TycA or TycA-S563A, ATP, or CoA from the appropriate enzyme assay mixture did not yield a detectable [M–H]$^-$ ion consistent with the mass of α-phenylalanyl-CoA, β-phenylalanyl-CoA, nor phenylisoserinyl CoA, as expected for a ATP/$Mg^{2+}$-dependent CoA ligase.

The stereochemistry of the amino phenylpropanoyl side chain was not evaluated and so it is unknown whether the products of the CoA reaction interacted with the E-domain of TycA and its cognate mutant TycA-S563A that could potentially epimerize the stereocenters of the CoA thioester products.

Figure 6:
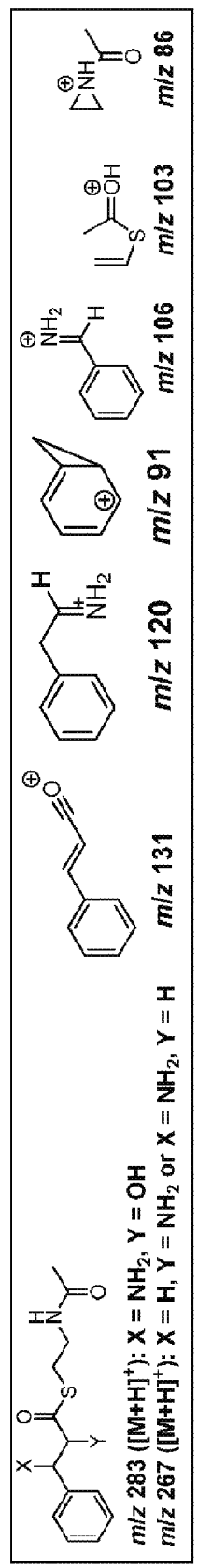
FIG. 6A-C shows representative liquid chromatography multiple reaction monitoring (LC-ESI-MRM) profiles of purified phenylalanyl-N-acetylcysteamine or phenylisoserinyl-N-acetylcysteamine compounds (FIG. 6A1, 6B1, 6C1), LC-ESI-MS analyses of total ion profiles (FIG. 6A2, 6B2, 6B2), and fragment ions derived by MS/MS of the corresponding [M+H]⁺ molecular ion (FIG. 6A3, 6B3, 6C3) of biosynthetic α-phenylalanyl N-acetylcysteamine (FIG. 6A), β-phenylalanyl N-acetylcysteamine (FIG. 6B), and (2S,3R)-phenylisoserinyl N-acetylcysteamine (FIG. 6C) made in reactions containing TycA or TycA-S563A (50 µg), ATP (1 mM), MgCl₂ (3 mM), N-acetylcysteamine (5 mM), and the corresponding aminophenylpropanoate at 1 mM. The [M+H]⁺ ions selected for MS/MS analysis from each sample are identified in bold and with an asterisk.
Figure 8:
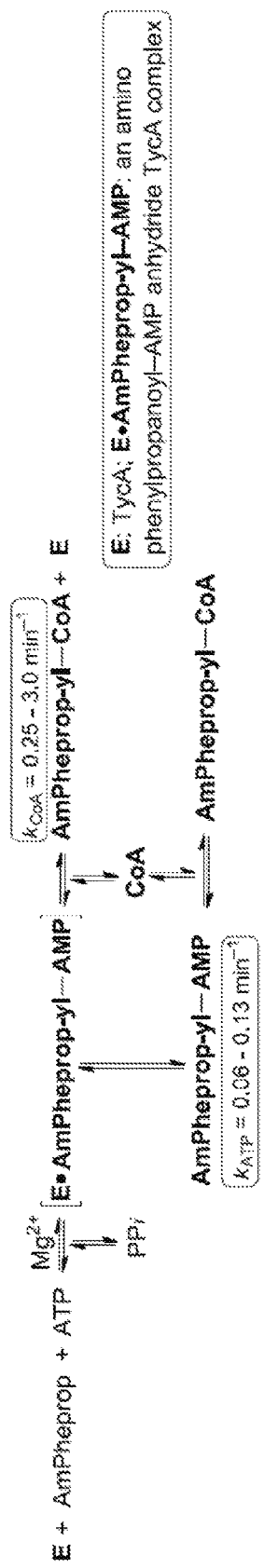
FIG. 8 illustrates the CoA thioesterification reaction catalyzed by TycA.

LC-ESI-MS/MS analysis of the products made in assays incubated with N-acetylcysteamine instead of CoA revealed fragment ions of the [M+H]$^+$ ion that were consistent with S-(α-phenylalanyl)-N-(acetyl)cysteamine or S-(β-phenylalanyl)-N-(acetyl)cysteamine (m/z 267, eluting at 4.49 and 3.01 min, respectively) and S-(phenylisoserinyl)-N-(acetyl)cysteamine (m/z 283, eluting at 2.32 min). The MS data for each biosynthetic S-(acyl)-N-(acetyl)cysteamine matched those of authentic standards (FIG. 6). Control assays that lacked enzyme from the assay mixture, but included the necessary cofactors and substrate did not yield a detectable molecular ion consistent with the identity of a S-(acyl)-N-(acetyl)cysteamine thioester (data not shown).

The data indicate that the following reactions are involved, and that these reactions generate the indicated structures.

from the TycA enzyme (e.g., R can be serine 563 of the TycA T-domain); R can also be adenosyl diphosphate; or R can be a methyl group if the thiol is N-acetylcysteamine.

Kinetic Analyses of TycA and TycA-S563A as Thiol Ligases.

The kinetic parameters of TycA and TycA-S563A were calculated by separately incubating each catalyst with various dilutions of aminophenylpropanoate substrate along with CoA or NAC and cofactors at apparent saturation. The resulting acyl-CoA and acyl-SNAC thioester products were quantified by LC-ESI-MRM (multiple reaction monitoring).

Kinetics with CoA.

The catalytic preference of TycA for (R)-β-Phe was 5- and 10-fold higher than for (S)-α-Phe and (2R,3S)-Phenylisoserine, respectively. The $K_M$ values of TycA (Table 1) suggested a preference for α-Phe and β-Phe with a $C_\alpha$—$NH_2$ or

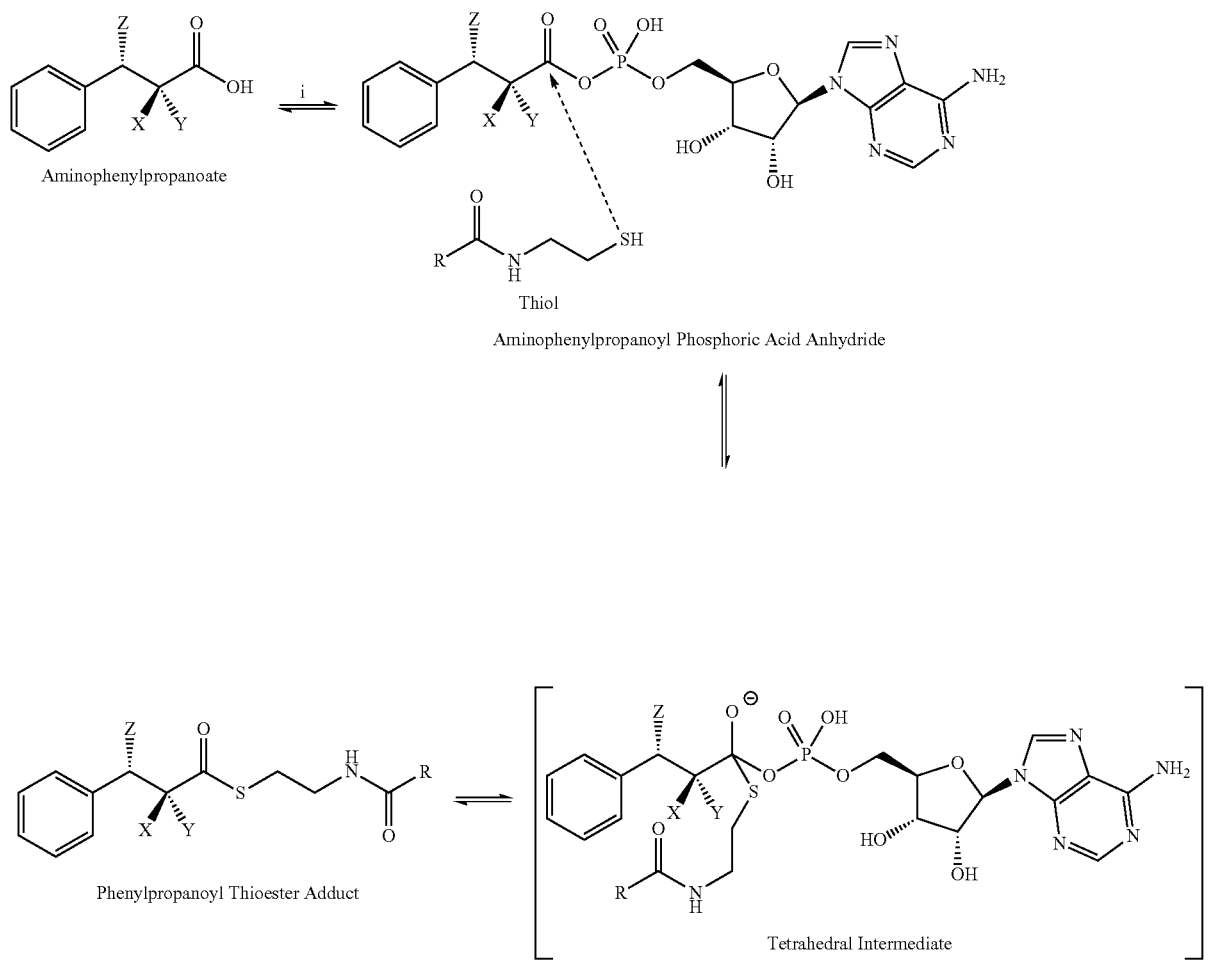

i = TycA, ATP, Mg$^{2+}$
ii = TycA catalyzed nucleophilic thioesterification

The X, Y and Z variables depend upon the aminophenylpropanoate substrate employed. For (S)-α-phenylalanine X is $NH_2$, while Y and Z are both hydrogen. For (R)-β-phenylalanine X and Y are both hydrogen while Z is $NH_2$. For (2R,3S)-phenylisoserine X is hydrogen, Y is OH and Z is $NH_2$. The R substituent on the thiol can be a T-domain $C_\beta$—$NH_2$ group, but not for phenylisoserine with a $C_\alpha$—OH and $C_\beta$—$NH_2$ group. The stereochemistry of the $C_\beta$—$NH_2$ of (2R,3S)-phenylisoserine is oriented identically to the amino group of (R)-β-Phe; thus, the $C_\alpha$—OH was considered responsible for affecting the catalysis either by sterics, electronic effects, or H-bonding interactions.

TABLE 1

Steady-state kinetic analysis of the TycA and TycA-S563A

| Substrate | $K_M$ (μm) | $k_{cat}^{CoA}$ (min$^{-1}$) | $k_{cat}^{CoA}/K_M$ (s$^{-1}$ · M$^{-1}$) | $k_{cat}^{ATP}$ (min$^{-1}$) | $k_{cat}^{ATP}/K_M$ (S$^{-1}$ · M$^{-1}$) |
|---|---|---|---|---|---|
| TycA | | | | | |
| (S)-α-Phe | 41.9 ± 2.0 | 0.25 ± 0.01 | 99.4 ± 6.2 | 0.13 ± 0.01 | 51.7 ± 1.7 |
| (R)-β-Phe | 50.6 ± 7.9 | 1.6 ± 0.3 | 527 ± 129 | 0.10 ± 0.01 | 32.9 ± 0.14 |
| (2R,3S)-PheIso | 89.3 ± 15.0 | 0.25 ± 0.02 | 46.7 ± 8.7 | c | c |
| CoA$^a$ | 1976 ± 175 | 0.75 ± 0.05 | 6.3 ± 0.7 | — | — |
| TycA-S563A | | | | | |
| (S)-α-Phe | 33.9 ± 4.0 | 0.69 ± 0.08 | 339 ± 56 | 0.09 ± 0.01 | 44.2 ± 0.2 |
| (R)-β-Phe | 62.3 ± 1.0 | 3.00 ± 0.04 | 803 ± 17 | 0.06 ± 0.01 | 16.1 ± 1.2 |
| (2R,3S)-PheIso | 191 ± 10 | 0.43 ± 0.01 | 37.5 ± 2.1 | c | c |
| CoA$^a$ | 804 ± 26 | 0.90 ± 0.08 | 18.7 ± 1.8 | — | — |

| Substrate | $K_M$ (μM) | $k_{cat}^{NAC}$ (min$^{-1}$) | $k_{cat}^{NAC}/K_M$ (s$^{-1}$ · M$^{-1}$) |
|---|---|---|---|
| TycA with NAC | | | |
| (S)-α-Phe | 27.0 ± 6.5 | 0.05 ± <0.01 | 30.8 ± 9.7 |
| (R)-β-Phe | 30.4 ± 3.9 | 0.36 ± 0.06 | 197 ± 42 |
| (2R,3S)-PheIso | 132 ± 56 | 0.19 ± 0.01 | 24.0 ± 10.3 |
| NAC$^a$ | 153 ± 22 | 0.09 ± <0.01 | 9.8 ± 1.8 |
| TycA-S563A with NAC | | | |
| (S)-α-Phe | 37.8 ± 1.6 | 0.20 ± 0.002 | 88.1 ± 3.8 |
| (R)-β-Phe | 58.9 ± 6.4 | 0.024 ± 0.001 | 6.8 ± 0.8 |
| (2R,3S)-PheIso | 512 ± 43 | 0.31 ± 0.05 | 10.1 ± 1.8 |
| NAC$^a$ | 268 ± 4 | 0.10 ± <<0.01 | 6.2 ± 0.6 |

Kinetic measurements for CoA or NAC determined with (S)-α-Phe$^a$ as cosubstrate.
All values are expressed as means ± standard deviations of triplicates.
c PheIso-yl AMP was below the limits of detection.
$k_{cat}^{CoA}$, $k_{cat}^{NAC}$ and $k_{cat}^{ATP}$ are turnover in the presence of CoA, NAC, and ATP at apparent saturation, respectively.

The catalytic efficiency of TycA-S563A for (R)-β-Phe was highest and followed a similar trend to that of TycA (Table 1). In general, the catalytic efficiency of TycA did not vary more than 3-fold over that of TycA-S563A, suggesting that the concentration of CoA at 1 mM offset the pantetheinylation reaction with the likely small fraction of TycA holoenzyme, containing the 4'-phosphopantetheine at the T-domain. Thus, CoA likely attacked the aminophenylpropanoyl-AMP anhydride while it remained docked in the A-domain of TycA. At this point, the fraction of AMP anhydride that reacted with CoA, after it was released into the medium, could not be determined. TycA was therefore deemed operationally similar to TycA-S563A at high concentrations of CoA.

The kinetic parameters of the enzymes were also calculated using a dilution series of CoA with 1 mM (S)-α-Phe. The resulting thioester product was quantified by LC-ESI-MRM, as before, and the $k_{cat}/K_M$ of the TycA congeners for CoA were of a similar order of magnitude (Table 1). However, the difference in catalytic preference between each enzyme was largely influenced by the ~2.5-fold higher $K_M$ of TycA, yet similar $k_{cat}$, compared to that of TycA-S563A (Table 1). The lower $K_M$ of TycA-S563A may suggest competitive inhibition between CoA, at low concentration, and a small amount of covalent 4'-phosphopantetheine at the T-domain.

Kinetics of the AMP Ligase Reaction.

The syntheses of authentic aminophenyl-propanoyl-AMPs using a method described by Owczarek, et al. (Biochemistry 47: 301-307 (2008)) for use as quantification standards was low yielding. Therefore, the biosynthetic acyl-AMPs were quantified by LC-ESI-MRM for kinetic analyses. The $k_{cat}^{ATP}/K_M$ value of TycA for the conversion of α-phenylalanine and β-phenylalanine (using ATP at apparent saturation (cf. FIG. 2)) to α-Phe-AMP and β-Phe-AMP were about 2-fold and 15-fold, respectively, which is lower than the values for the conversion of α-Phe and β-Phe to their corresponding authentic aminophenylpropanoyl-CoA thioesters (Table 1). The $k_{cat}^{ATP}/K_M$ value of TycA-S563A for similar conversion of α-phenylalanine and β-phenylalanine to the AMP adducts was about 7-fold and about 46-fold lower, respectively. Phenylisoserinyl-AMP was below the limits of detection in a similar assay. The slower steady-state production rate of the aminophenylpropanoyl-AMP in solution (FIG. 3) did not account for the production rate of the corresponding aminophenylpropanoyl-CoAs. The greater catalytic efficiency for CoA thioester production over aminopropanoyl AMP biosynthesis confirmed that CoA displaced AMP from the aminophenylpropanoyl-AMP in complex with TycA, at steady state, and not from the acyl AMP intermediate in solution to form the thioesters.

Kinetics with NAC.

The $k_{cat}$ and $K_M$ values of TycA or TycA-S563A for N-acetylcysteamine (NAC) were obtained by incubating the thiol separately with each aminophenylpropanoate under standard ligase conditions. The reaction products were identified and quantified by LC-ESI-MRM by comparison to the retention time and fragment transition ions of authentic standards. The efficiency of TycA (with NAC) was highest for (R)-β-Phe, followed by (S)-α-Phe, and then by (2R,3S)-phenylisoserine, similar (but at lower values) to when CoA was used in place of NAC (Table 1). The $K_M$ values of TycA for each aminophenylpropanoate substrate with NAC at apparent saturation was different, but approximately the same order of magnitude as when CoA was used. These data suggest that the smaller NAC thiol did not affect binding of the aminophenylpropanoate to the PheA domain (Table 1). The $k_{cat}/K_M$ of TycA for each aminophenylpropanoate and NAC ranged between 1.5- and 3-fold lower than when CoA was used, suggesting that CoA is more catalytically competent than NAC, as anticipated.

The catalytic efficiency of TycA-S563A (compared with TycA) was lower for (R)-β-Phe and (2R,3S)-Phenylisoserine and NAC cosubstrate, but increased for the natural substrate (S)-α-Phe. These results somewhat contradicted other findings that the catalytic efficiency of TycA-S563A was highest for β-Phe (Table 1). A 15-fold decrease in turnover and an approximate 2-fold increase in $K_M$ caused a ~30-fold lower catalytic efficiency of TycA-S563A compared to that of TycA for (R)-β-Phe (Table 1). This disparity was not seen between the catalytic efficiency of each catalyst for CoA and (R)-β-Phe. Apparently, an as yet unknown interaction between NAC, β-Phe, and/or the catalyst affected the turnover. Interestingly, the $K_M$ of both TycA and TycA-S563A for NAC were lower than for CoA (Table 1), despite CoA being a better mimic of the natural Ppant used in the normal TycA reaction (FIG. 2A). It is unclear whether the smaller NAC has greater reach to the TycA active site than CoA and thus affects the rate of the ligase reaction chemistry.

Comparing the Kinetic Parameters of TycA/TycA-S563A to Other CoA Ligases.

Compared to the $K_M$ values of bacterial CoA Ligases for CoA (100-940 μM) and acyl substrates (10-6000 μM), those of TycA and TycA-S563A for CoA (1976 and 804 μM, respectively) are about the same order of magnitude, while the acyl substrates (34-132 μM) are more variable (Tables 1 and 2).

al., 2009). Likewise, the $k_{cat}/K_M$ of TycA, which already uses aminophenylpropanoate substrates, may potentially be enhanced through mutagenesis by removing the T- and E-domains to resolve the CoA Ligase activity of the A-domain.

SUMMARY

Under CoA ligation assay conditions, TycA (and TycA-S563A) converted three aryl α- and β-amino acids to their CoA and S—N-acetylcysteamine thioesters via adenylate intermediates kinetically similar to CoA ligases involved in secondary metabolism. The S—N-acetylcysteamine thioesters of each amino acid were biosynthesized when N-acetylcysteamine was used as the thiol donor.

Notably, the β-Phenylpropanyl-CoA and phenylisoserinyl-CoA thioesters made as described herein are useful intermediates on the biosynthetic pathway of paclitaxel, and thus, can be used to make paclitaxel and related antineoplastic drugs.

REFERENCES

Altenschmidt, U., Oswald, B., and Fuchs, G. (1991). Purification and characterization of benzoate-coenzyme-A ligase and 2-aminobenzoate-coenzyme-A ligases from a denitrifying *Pseudomonas* sp. J. Bacteriol. 173, 5494-5501.

TABLE 2

| CoA Ligase (CL) | Substrate | $K_M$ (μM) | kcat (min$^{-1}$) | kcat/$K_M$ (s$^{-1}$ · M$^{-1}$) |
|---|---|---|---|---|
| Propionyl-CL | propionate | 20 | 1980 | $1.65 \times 10^6$ |
| | CoA | 215 | 2520 | $1.95 \times 10^5$ |
| Benzoate-CL | benzoate | 11 | 26,000 | $3.94 \times 10^7$ |
| | CoA | 100 | NL$^a$ | NL |
| Phenylacetate-CL | phenylacetate | 6100 | 84 | 230 |
| | CoA | 940 | NL | NL |
| Cinnamate-CL | Cinnamate | 190 | 28.5 | 2500 |
| | CoA | NL | NL | NL |
| 4-Chlorobenzoate-CL | 4-Cl-benzoate | 0.9 | 552 | $1.02 \times 10^7$ |
| | CoA | 310 | 558 | $3.00 \times 10^4$ |

$^a$NL: no listing

CoA ligases active during catabolic pathways in various bacteria convert, for example, propionate (Horswill & Escalante-Semerena, Biochemistry 41: 2379-2387 (2002)), benzoate (Altenschmidt, et al., J. Bacteriol. 173: 5494-5501 (1991)), and 4-chlorobenzoate (Wu, et al., Biochemistry 48: 4115-4125 (2009)) to their corresponding CoA thioesters with superior catalytic efficiency ($1.65 \times 10^6$, $3.94 \times 10^7$, and $1.02 \times 10^7$ s$^{-1}$·M$^{-1}$, respectively) compared to those on secondary metabolic pathways (≤2500 s$^{-1}$·M$^{-1}$), such as for TycA, (used in tyrocidines A-D biosynthesis, described here as a CoA Ligase), phenylacetate CoA Ligase from *Penicillium chrysogenum* (Koetsier, et al., Biochem. J. 417: 467-476 (2009)), penicillin G biosynthesis, and cinnamate CoA Ligase from *Streptomyces coelicolor* (Kaneko, et al., J. Bacteriol. 185, 20-27 (2003)). The role of cinnamoyl CoA is as yet undefined; however, it may play a role in biosynthesis, since *Streptomyces* sp. are known to produce a variety of secondary products (Ohnishi, et al., J. Bacteriol. 190: 4050-4060 (2008)). Notably, a recent report described a mutation of phenylacetate CoA Ligase from *P. chrysogenum* that reduced the $K_M$ for β-Phe from low mM amount to 68 μM in the reaction to make β-Phenylpropanyl CoA (Koetsier, et Anderson, L., and Hunter, C. L. (2006). Quantitative mass spectrometric multiple reaction monitoring assays for major plasma proteins. Mol. Cell. Proteomics 5, 573-588.

Ehmann, D. E., Shaw-Reid, C. A., Losey, H. C., and Walsh, C. T. (2000). The EntF and EntE adenylation domains of *Escherichia coli* enterobactin synthetase: Sequestration and selectivity in acyl-AMP transfers to thiolation domain cosubstrates. Proc. Natl. Acad. Sci. U.S.A. 97, 2509-2514.

Food and Drug Adminstration (2012). Current Drug Shortages, see website at fda.gov/Drugs/DrugSafety/Drug-Shortages/ucm050792.htm Harmrolfs, K., Brunjes, M., Drager, G., Floss, H. G., Sasse, F., Taft, F., and Kirschning, A. (2010). Cyclization of synthetic seco-proansamitocins to ansamitocin macrolactams by Actinosynnema pretiosum as biocatalyst. ChemBioChem 11, 2517-2520.

Horswill, A. R., and Escalante-Semerena, J. C. (2002). Characterization of the propionyl-CoA synthetase (PrpE) enzyme of *Salmonella enterica*: Residue Lys592 is required for propionyl-AMP synthesis. Biochemistry 41, 2379-2387.

Jennewein, S., Wildung, M. R., Chau, M., Walker, K., and Croteau, R. (2004). Random sequencing of an induced *Taxus* cell cDNA library for identification of clones involved in Taxol biosynthesis. Proc. Natl. Acad. Sci. U.S.A. 101, 9149-9154 (and references therein).

Jeong, H., Barbe, V., Lee, C. H., Vallenet, D., Yu, D. S., Choi, S.-H., Couloux, A., Lee, S.-W., Yoon, S. H., Cattolico, L., et al. (2009). Genome sequences of *Escherichia coli* B strains REL606 and BL21(DE3). J. Mol. Biol. 394, 644-652.

Kaneko, M., Ohnishi, Y., and Horinouchi, S. (2003). Cinnamate:coenzyme A ligase from the filamentous bacterium *Streptomyces coelicolor* A3(2). J. Bacteriol. 185, 20-27.

Koetsier, M. J., Jekel, P. A., van den Berg, M. A., Bovenberg, R. A. L., and Janssen, D. B. (2009). Characterization of a phenylacetate-CoA ligase from *Penicillium chrysogenum*. Biochem. J. 417, 467-476.

Lautru, S., and Challis, G. L. (2004). Substrate recognition by nonribosomal peptide synthetase multi-enzymes. Microbiology 150, 1629-1636.

Meier, J. L., and Burkart, M. D. (2011). Proteomic analysis of polyketide and nonribosomal peptide biosynthesis. Curr. Opin. Chem. Biol. 15, 48-56.

Mountford, P. G. (2010). The Taxol® Story—Development of a Green Synthesis via Plant Cell Fermentation. In Green Chemistry in the Pharmaceutical Industry, P. J. Dunn, A. S. Wells, and M. T. Williams, eds. (Wiley-VCH Verlag GmbH & Co. KGaA), pp. 145-160.

Ohnishi, Y., Ishikawa, J., Hara, H., Suzuki, H., Ikenoya, M., Ikeda, H., Yamashita, A., Hattori, M., and Horinouchi, S. (2008). Genome sequence of the streptomycin-producing microorganism *Streptomyces griseus* IFO 13350. J. Bacteriol. 190, 4050-4060.

Owczarek, A., Safro, M., and Wolfson, A. D. (2008). Enzymatic tRNA acylation by acid and a-hydroxy acid analogues of amino acids. Biochemistry 47, 301-307.

Villiers, B. R. M., and Hollfelder, F. (2009). Mapping the limits of substrate specificity of the adenylation domain of TycA. Chembiochem 10, 671-682.

Wu, R., Reger, A. S., Lu, X., Gulick, A. M., and Dunaway-Mariano, D. (2009). The mechanism of domain alternation in the acyl-adenylate forming ligase superfamily member 4-chlorobenzoate: coenzyme A ligase. Biochemistry 48, 4115-4125.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific compositions and methods described herein are representative, exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a compound" or "a catalyst" or "a ligand" includes a plurality of such compounds, catalysts or ligands, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

The following statements describe aspects of the invention.

STATEMENTS DESCRIBING ASPECTS OF THE INVENTION

1. A method of making paclitaxel or an analog thereof, comprising preparing an aminopropanoyl-CoA in a reaction catalyzed by a Tyrocidine synthetase A (TycA) to thereby make paclitaxel or an analog or derivative thereof.
2. The method of statement 1, wherein the aminopropanoyl-CoA is prepared from a substrate of the following formula I:

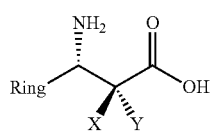

wherein:
X is hydrogen;
Y is hydrogen or OH; and
Ring is a unsubstituted or substituted (C4-C10) aryl, (C4-C9)heteroaryl, (C4-C10)cycloalkyl, or (C4-C9)heterocycloalkyl.

3. The method of statement 1 or 2, wherein the aminopropanoyl-CoA is a compound of formula II:

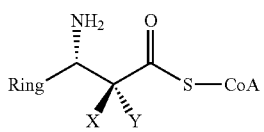

wherein:
X is hydrogen;
Y is hydrogen or OH; and
Ring is a unsubstituted or substituted (C4-C10) aryl, (C4-C9)heteroaryl, (C4-C10)cycloalkyl, or (C4-C9)heterocycloalkyl.

4. The method of any of statements 1-3, wherein the paclitaxel or paclitaxel analog has the following structure:

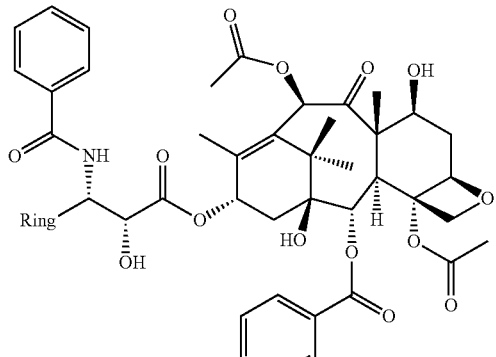

Paclitaxel, Analog or Derivative wherein:
Ring is a unsubstituted or substituted (C4-C10) aryl, (C4-C9)heteroaryl, (C4-C10)cycloalkyl, or (C4-C9)heterocycloalkyl.

5. The method of any of statements 1-4, wherein Ring is a single aryl or heteroaryl ring of about 4-8 carbon atoms, and where the heteroatom is oxygen or nitrogen.

6. The method of any of statements 1-5, wherein the Ring is substituted with 1 or 2 alkyl, amino, hydroxy, cyano, carboxy, nitro, thio, alkoxy, and halogen groups.

7. The method of any of statements 1-6, wherein the aminopropanoyl-CoA is prepared from a substrate of the following formula III or IV:

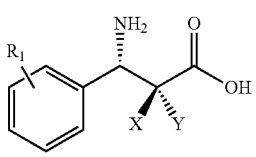

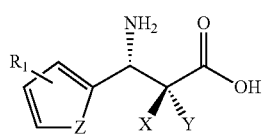

wherein:
X is hydrogen;
Y is hydrogen or OH;
Z is CH, $CH_2$, oxygen (O) or nitrogen (NH or $NH_2$); and
$R_1$ is selected from the group consisting of hydrogen, alkyl, amino, hydroxy, cyano, carboxy, nitro, thio, alkoxy, and halogen.

8. The method of any of statements 1-7, wherein the aminopropanoyl-CoA is of the formula V or VI:

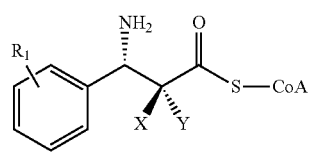

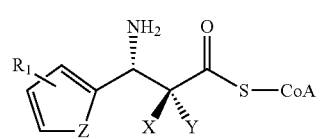

wherein:
X is hydrogen;
Y is hydrogen or OH;
Z is CH, $CH_2$, oxygen (O), or nitrogen (NH or $NH_2$); and
$R_1$ is selected from the group consisting of hydrogen, alkyl, amino, hydroxy, cyano, carboxy, nitro, thio, alkoxy, and halogen.

9. The method of any of statements 1-8, wherein the Tyrocidine synthetase A has a bacterial amino acid sequence.

10. The method of any of statements 1-9, wherein the Tyrocidine synthetase A is a *Bacillus brevis* or *Brevibacillus parabrevis* Tyrocidine synthetase A.

11. The method of any of statements 1-10, wherein the Tyrocidine synthetase A has an amino acid sequence of a Tyrocidine synthetase A from bacteria deposited with the American Type Culture Collection under deposit number ATCC 8185.

12. The method of any of statements 1-11, wherein a serine in the Tyrocidine synthetase A is replaced with a substitute amino acid that does not have a hydroxy in its side chain.

13. The method of any of statements 1-12, wherein a serine at about position 563 in the Tyrocidine synthetase A is replaced with a substitute amino acid that does not have a hydroxy in its side chain.

14. The method of statements 12 or 13, wherein the substitute amino acid in the Tyrocidine synthetase A is an alanine, valine, isovaline, leucine, isoleucine, proline, glycine, arginine, lysine, histidine, tryptophan, phenylalanine, methionine or cysteine.
15. The method of any of statements 1-14, wherein the Tyrocidine synthetase A has an amino acid sequence comprising a sequence selected from the group consisting of SEQ ID NO:1, SEQ ID NO:3, SEQ ID NO:5, SEQ ID NO:6, and an amino acid sequence with 85% sequence identity to any of SEQ ID NO:1, SEQ ID NO:3, SEQ ID NO:5, or SEQ ID NO:6.
16. The method of any of statements 1-15, wherein the Tyrocidine synthetase A is encoded by a nucleic acid sequence comprising a sequence selected from the group consisting of SEQ ID NO:2, SEQ ID NO:4, SEQ ID NO:7, and an nucleic acid sequence with 85% sequence identity to any of SEQ ID NO:2, SEQ ID NO:4 or SEQ ID NO:7.
17. The method of any of statements 1-16, wherein the reaction comprises a mixture of the Tyrocidine synthetase A, the substrate, ATP and a divalent cation.
18. The method of any of statements 1-17, which is performed in vitro.
19. The method of any of statements 1-18, which is performed in a cell-free reaction.
20. The method of any of statements 1-17, which occurs in a cultured cell.
21. The method of any of statements 1-17, which occurs in a cultured cell during a plant cell fermentation process.
22. The method of any of statements 1-21, wherein the method further comprises reaction B comprising combining the aminopropanoyl-CoA with Baccatin III:

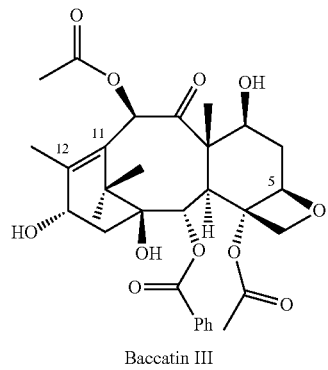

Baccatin III to form N-debenzoyl-2'-deoxypaclitaxel or an analog or derivative thereof.
23. The method of statement 22, wherein the reaction B is catalyzed by an acyltransferase.
24. The method of statement 22 or 23, wherein the reaction B is catalyzed by a *Taxus* acyltransferase.
25. The method of any of statements 22-43, wherein the reaction B is catalyzed by baccatin III O-phenylpropanoyltransferase (BAPT).
26. The method of any of statements 22-25, wherein the reaction B comprises a mixture of aminopropanyl-CoA, baccatin III O-phenylpropanoyltransferase (BAPT), and Baccatin III.
27. The method of any of statements 22-26, wherein the N-debenzoyl-2'-deoxypaclitaxel or an analog or derivative thereof has the following structure:

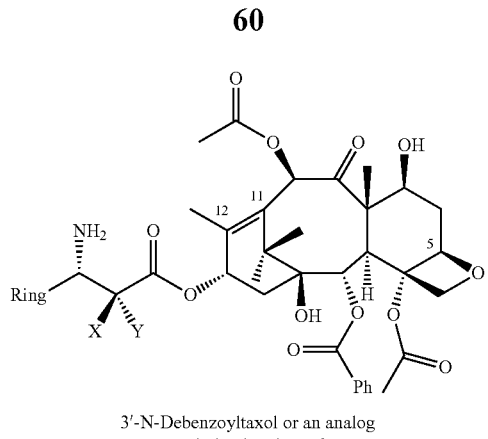

3'-N-Debenzoyltaxol or an analog
or derivative thereof wherein:
X is hydrogen;
Y is hydrogen or OH; and
Ring is a unsubstituted or substituted (C4-C10) aryl, (C4-C9)heteroaryl, (C4-C10)cycloalkyl, or (C4-C9)heterocycloalkyl.
28. The method of any of statements 22-27, which is performed in vitro.
29. The method of any of statements 22-28, which is performed in a cell-free reaction.
30. The method of any of statements 22-27, which is performed in a cultured cell.
31. The method of any of statements 22-27, which is performed in a cultured cell during a plant cell fermentation process.
32. The method of any of statements 1-31, wherein the method further comprises a reaction A comprising transfer of benzoyl group to a free amine of a propanoid side chain of 3'-N-debenzoyl-paclitaxel or an analog or derivative thereof to form paclitaxel or an analog or derivative thereof.
33. The method of statement 32, wherein the paclitaxel or an analog or derivative thereof has the following structure:

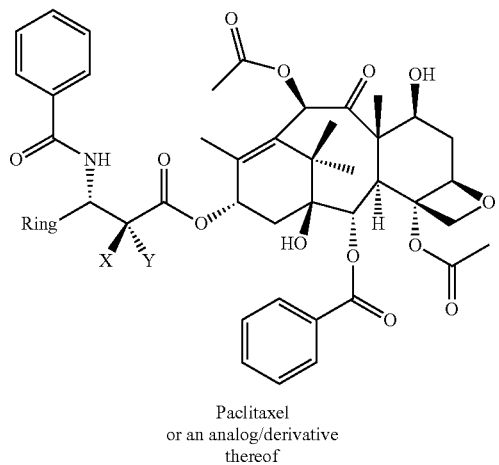

Paclitaxel
or an analog/derivative
thereof wherein:
Ring is a unsubstituted or substituted (C4-C10) aryl, (C4-C9)heteroaryl, (C4-C10)cycloalkyl, or (C4-C9)heterocycloalkyl.

34. The method of statement 33, wherein Ring is a single aryl or heteroaryl ring of about 4-8 carbon atoms, and where the heteroatom is oxygen or nitrogen.
35. The method of statement 33 or 34, wherein the Ring is substituted with 1 or 2 alkyl, amino, hydroxy, cyano, carboxy, nitro, thio, alkoxy, and halogen groups.
36. The method of any of statements 32-35, wherein the reaction A is catalyzed by an acyltransferase.
37. The method of any of statements 32-36, wherein the reaction A is catalyzed by a *Taxus* acyltransferase.
38. The method of any of statements 32-37, wherein the reaction A is catalyzed by N-debenzoyl-2'-deoxypaclitaxel: N-benzoyltransferase (NDTBT).
39. The method of any of statements 32-38, wherein the reaction A comprises a mixture of 3'-N-debenzoyl-paclitaxel, a benzoyl-contributing agent and N-debenzoyl-2'-deoxypaclitaxel: N-benzoyltransferase (NDTBT).
40. The method of any of statements 32-39, which is performed in vitro.
41. The method of any of statements 32-40, which is performed in a cell-free reaction.
42. The method of any of statements 31-39, which is performed in a cultured cell.
43. The method of any of statements 31-39, which is performed in a cultured cell during a plant cell fermentation process.
44. The method of any of any of statements 1-43, wherein the method further comprises a reaction C comprising acyl transfer of an acetyl group to 10-deacetyl Baccatin III to generate Baccatin III:

[Structure of 10-Deacetyl Baccatin III]

→ C

[Structure of Baccatin III]

45. The method of statement 44, wherein reaction C is catalyzed by an acetyl transferase.
46. The method of statement 44 or 45, wherein reaction C is catalyzed by 10-deacetylbacctin III acetyltransferase.
47. The method of any of statements 44-46, which is performed in vitro.

48. The method of any of statements 44-47, which is performed in a cell-free reaction.
49. The method of any of statements 44-46, which is performed in a cultured cell.
50. The method of any of statements 44-46, which is performed in a cultured cell during a plant cell fermentation process.
51. The method of any of statements 1-50, wherein the method further comprises a reaction D comprising transfer of a benzoyl group to 2-debenzoyltaxane to generate 10-deacetyl Baccatin III.
52. The method of statement 51, wherein reaction D proceeds as follows:

[Structure of 2-Debenzoyltaxane]

→ D

[Structure of 10-Deacetyl Baccatin III]

53. The method of statement 51 or 52, wherein reaction D is catalyzed by taxane 2a-O-benzoyltransferase.
54. The method of any of statements 51-53, which is performed in vitro.
55. The method of any of statements 51-54, which is performed in a cell-free reaction.
56. The method of any of statements 51-53, which is performed in a cultured cell.
57. The method of any of statements 51-53, which is performed in a cultured cell during a plant cell fermentation process.
58. The method of any of statements 1-57, wherein the method further comprises a reaction E comprising acylation and hydroxylation of taxa-4(5),11(12)-diene-5a-ol to generate 2-debenzoyltaxane.
59. The method of statement 58, wherein reaction E proceeds as follows:

[Structure of Taxa-4(5),11(12)-diene-5a-ol] → E

-continued

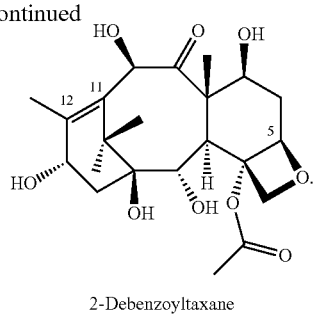

2-Debenzoyltaxane

60. The method of statement 58 or 59, wherein reaction E is catalyzed by an enzyme selected from the group consisting of taxadiene 13-hydroxylase (T13H), taxadienol 5α-O-acetyl transferase (TAT), taxadiene 10-hydroxylase (T10H), or a combination thereof.
61. The method of any of statements 58-60, which is performed in vitro.
62. The method of any of statements 58-61, which is performed in a cell-free reaction.
63. The method of any of statements 58-60, which is performed in a cultured cell.
64. The method of any of statements 58-60, which is performed in a cultured cell during a plant cell fermentation process.
65. The method of any of statements 1-64, wherein the method further comprises a reaction F comprising hydroxylation of taxa-4(5),11(12)-diene to generate taxa-4(5),11(12)-diene-5α-ol.
66. The method of statement 65, wherein reaction F proceeds as follows:

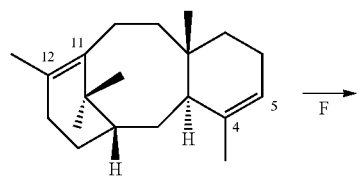

Taxa-4(5),11(12)-diene

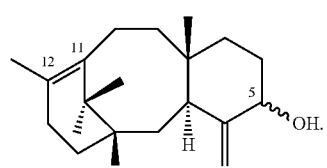

Taxa-4(5),11(12)-diene-5α-ol

67. The method of statement 65 or 66, wherein reaction F is catalyzed by taxadiene 5α-hydroxylase.
68. The method of any of statements 65-67, which is performed in vitro.
69. The method of any of statements 65-68, which is performed in a cell-free reaction.
70. The method of any of statements 65-67, which is performed in a cultured cell.

71. The method of any of statements 65-67, which is performed in a cultured cell during a plant cell fermentation process.
72. The method of any of statements 1-71, wherein the method further comprises a reaction G comprising ring closure of geranylgeranyl diphosphate.
73. The method of statement 72, wherein reaction G generates taxa-4(5),11(12)-diene.
74. The method of statement 72 or 73, wherein reaction G proceeds as follows:

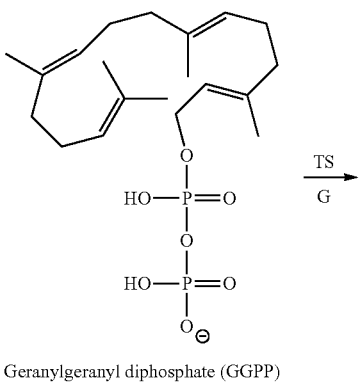

Geranylgeranyl diphosphate (GGPP)

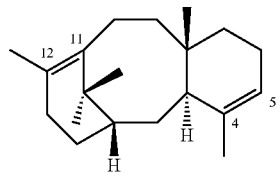

Taxa-4(5),11(12)-diene

75. The method of any of statements 72-73, wherein reaction G is catalyzed by taxadiene synthase.
76. The method of any of statements 72-75, which is performed in vitro.
77. The method of any of statements 72-76, which is performed in a cell-free reaction.
78. The method of any of statements 72-75, which is performed in a cultured cell.
79. The method of any of statements 71-75, which is performed in a cultured cell during a plant cell fermentation process.
80. The method of any of statements 1-79, wherein the method further comprises a reaction H comprising condensation of geranylgeranyl diphosphate and dimethylallyl diphosphate.
81. The method of statement 80, wherein the condensation generates taxa-4(5),11(12)-diene.
82. The method of statement 80 or 81, wherein reaction H proceeds as follows:

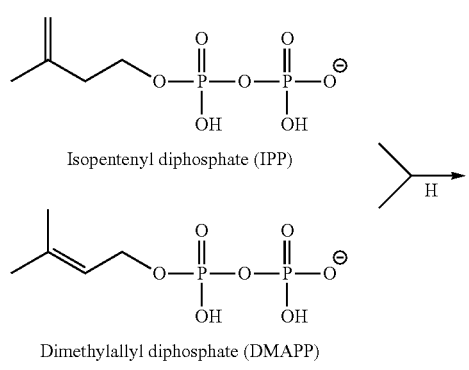

Isopentenyl diphosphate (IPP)

Dimethylallyl diphosphate (DMAPP)

Geranylgeranyl diphosphate (GGPP)

83. The method of any of statements 80-82, wherein reaction H is catalyzed by geranylgeranyl diphosphate synthetase.
84. The method of any of statements 80-83, which is performed in vitro.
85. The method of any of statements 80-84, which is performed in a cell-free reaction.
86. The method of any of statements 80-83, which is performed in a cultured cell.
87. The method of any of statements 80-83, which is performed in a cultured cell during a plant cell fermentation process.

The following claims describe aspects of the invention.

What is claimed:

1. A method of making paclitaxel or a derivative thereof, comprising contacting an aminopropanoate with a Tyrocidine synthetase A (TycA) to produce an aminopropanoyl-CoA and producing said paclitaxel or a derivative thereof from said aminopropanoyl-CoA.

2. The method of claim 1, comprising reacting a substrate represented by formula I with a Tyrocidine synthetase A (TycA) to produce an aminopropanoyl-CoA of formula II:

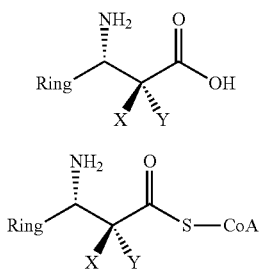

wherein:
X is hydrogen;
Y is hydrogen or OH; and
Ring is an unsubstituted or substituted aryl, heteroaryl, (C4-C10)cycloalkyl, or (C4-C9)heterocycloalkyl.

3. The method of claim 2 further comprising mixing said aminopropanoyl-CoA of formula II with Baccatin III of the formula:

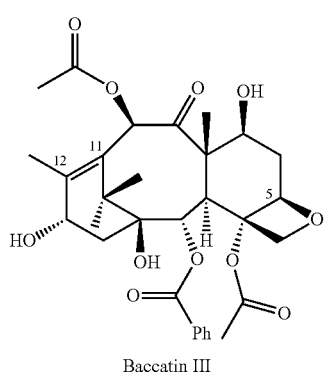

Baccatin III to form a mixture; and
reacting said mixture with a Baccatin III O-phenylpropanoyltransferase (BAPT) to produce N-debenzoyl-2'-deoxypaclitaxel of the formula:

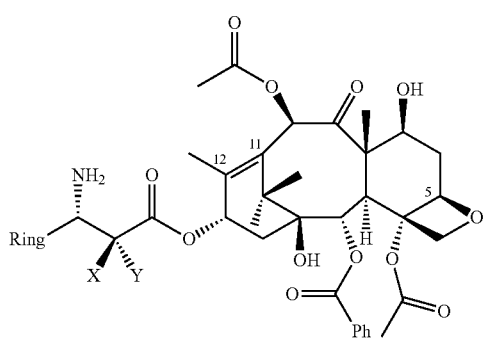

wherein:
X is hydrogen;
Y is hydrogen or OH; and
Ring is an unsubstituted or substituted aryl, heteroaryl, (C4-C10)cycloalkyl, or (C4-C9)heterocycloalkyl.

4. The method of claim 2, wherein said substrate of formula I comprises a structure represented by formula III or IV:

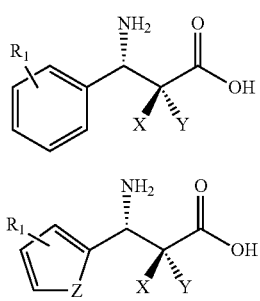

wherein:
X is hydrogen;
Y is hydrogen or OH;
Z is CH, CH$_2$, oxygen (O) or nitrogen (NH or NH$_2$); and
R$_1$ is selected from the group consisting of hydrogen, alkyl, amino, hydroxyl, cyano, carboxy, nitro, thio, alkoxy, and halogen.

5. The method of claim 2, wherein said aminopropanoyl-CoA of formula II comprises a structure of formula V or VI:

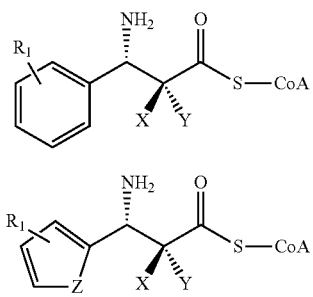

wherein:
X is hydrogen;
Y is hydrogen or OH;
Z is CH, CH$_2$, oxygen (O), or nitrogen (NH or NH$_2$); and R$_1$ is selected from the group consisting of hydrogen, alkyl, amino, hydroxy, cyano, carboxy, nitro, thio, alkoxy, and halogen.

6. The method of claim 1, wherein said Tyrocidine synthetase A is selected from the group consisting of:
a. a polypeptide comprising the amino acid sequence of SEQ ID NO: 1, SEQ ID NO: 3; SEQ ID NO: 5, or SEQ ID NO: 6;
b. a polypeptide comprising the amino acid sequence of SEQ ID NO: 1 with the exception of a substitution of a serine at an amino acid position corresponding to position 563 of the amino acid sequence of SEQ ID NO: 1, wherein said substitution does not have a hydroxy in its side chain;
c. a polypeptide comprising the amino acid sequence of SEQ ID NO: 1 with the exception of a substitution of a serine at an amino acid position corresponding to position 563 of the amino acid sequence of SEQ ID NO: 1, wherein said substitution is an alanine, valine, isovaline, leucine, isoleucine, proline, glycine, arginine, lysine, histidine, tryptophan, phenylalanine, methionine or cysteine;
d. a polypeptide comprising an amino acid sequence that shares at least 95% sequence identity to the amino acid sequence of SEQ ID NO: 1, SEQ ID NO: 3, SEQ ID NO: 5, or SEQ ID NO: 6;
e. a polypeptide encoded by the nucleotide sequence of SEQ ID NO: 2, SEQ ID NO: 4, or SEQ ID NO: 7;
f. a polypeptide encoded by the nucleotide sequence that shares at least 95% sequence identity to the nucleotide sequence of SEQ ID NO: 2, SEQ ID NO: 4, or SEQ ID NO: 7; and
g. a combination thereof.

7. The method of claim 2, wherein said reacting of said substrate of formula I comprises a mixture of said Tyrocidine synthetase A, said substrate of formula I, ATP and a divalent cation.

8. The method of claim 1, wherein said method is performed in vitro, in a cell-free reaction, in a cultured cell, or in a cultured cell during a plant cell fermentation process.

9. The method of claim 3, wherein the method further comprises reacting said N-debenzoyl-2'-deoxypaclitaxel with N-debenzoyl-2'-deoxypaclitaxel: N-benzoyltransferase (NDTBT) to produce a paclitaxel of the formula:

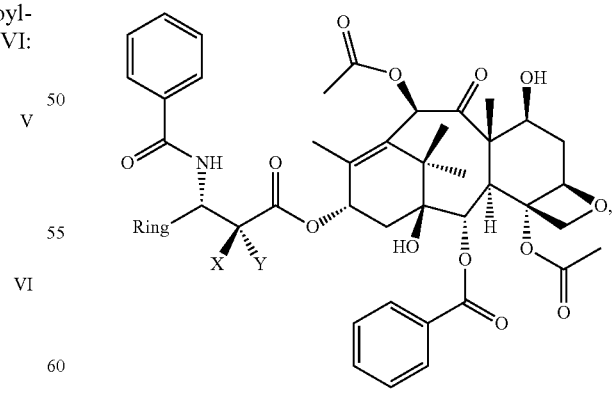

wherein:
X is hydrogen;
Y is hydrogen or OH; and
Ring is an unsubstituted or substituted aryl, heteroaryl, (C4-C10)cycloalkyl, or (C4-C9)heterocycloalkyl.

10. The method of claim 9, wherein said method is performed in vitro, in a cell-free reaction, in a cultured cell, or in a cultured cell during a plant cell fermentation process.

11. The method of claim 3, wherein said method further comprises reacting a 10-deacetyl Baccatin III of the formula:

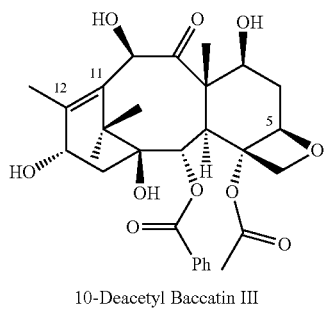

10-Deacetyl Baccatin III with a 10-deacetylbaccitin III acetyltransferase (DBAT) to produce said Baccatin III.

12. The method of claim 11, wherein said method is performed in vitro, in a cell-free reaction, in a cultured cell, or in a cultured cell during a plant cell fermentation process.

13. The method of claim 11, wherein said method further comprises reacting a 2-debenzoyltaxane of the formula:

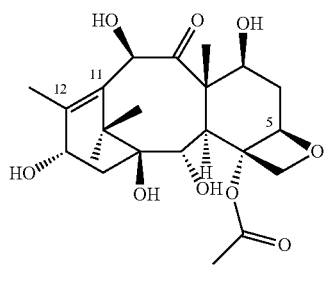

2-Debenzoyltaxane with a taxane 2α-O-benzoyltransferase (TBT) to produce said 10-deacetyl Baccatin III.

14. The method of claim 13, wherein said method is performed in vitro, in a cell-free reaction, in a cultured cell, or in a cultured cell during a plant cell fermentation process.

15. The method of claim 13, wherein said method further comprises reacting a taxa-4(5),11(12)-diene-5α-ol of the formula:

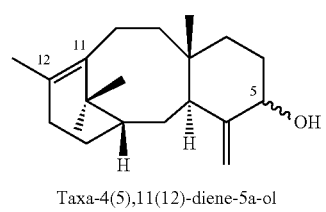

Taxa-4(5),11(12)-diene-5a-ol with a taxadienol 5α-O-acetyl-transferase (TAT) to produce said 2-debenzoyltaxane.

16. The method of claim 15, wherein said method is performed in vitro, in a cell-free reaction, in a cultured cell, or in a cultured cell during a plant cell fermentation process.

17. The method of claim 15, wherein said method further comprises reacting a taxa-4(5),11(12)-diene of the formula:

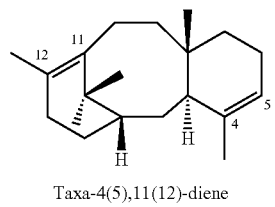

Taxa-4(5),11(12)-diene with a taxadiene 5α-hydroxylase to produce said taxa-4(5),11(12)-diene-5α-ol.

18. The method of claim 17, wherein said method is performed in vitro, in a cell-free reaction, in a cultured cell, or in a cultured cell during a plant cell fermentation process.

19. The method of claim 17, wherein said method further comprises reacting a geranylgeranyl diphosphate of the formula:

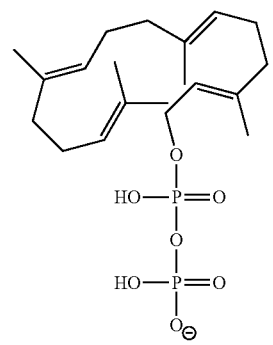

Geranylgeranyl diphosphate (GGPP)

with a taxadiene synthase to produce said taxa-4(5),11(12)-diene.

20. The method of claim 19, wherein said method is performed in vitro, in a cell-free reaction, in a cultured cell, or in a cultured cell during a plant cell fermentation process.

21. The method of claim 19, wherein method further comprises reacting an isopentenyl diphosphate of the formula:

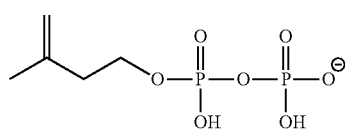

Isopentenyl diphosphate (IPP)

and dimethylallyl diphosphate of the formula:

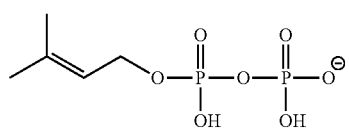

Dimethylallyl diphosphate (DMAPP)

with a geranylgeranyl diphosphate synthetase to produce said geranylgeranyl diphosphate.

22. The method of claim 21, wherein said method is performed in vitro, in a cell-free reaction, in a cultured cell, or in a cultured cell during a plant cell fermentation process.

23. The method of claim 2 further comprising mixing said aminopropanoyl-CoA of formula II with 10-deacetyl Baccatin III of the formula:

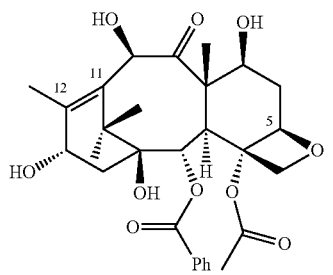

10-Deacetyl Baccatin III to form a mixture; and reacting said mixture with a Baccatin III O-phenylpropanoyltransferase (BAPT).

* * * * *